US009844513B2

(12) United States Patent
Coulter

(10) Patent No.: US 9,844,513 B2
(45) Date of Patent: Dec. 19, 2017

(54) ORAL PHARMACEUTICAL COMPOSITION

(75) Inventor: Ivan Coulter, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 847 days.

(21) Appl. No.: 13/441,780

(22) Filed: Apr. 6, 2012

(65) Prior Publication Data
US 2012/0258167 A1    Oct. 11, 2012

Related U.S. Application Data

(63) Continuation of application No. 12/594,542, filed as application No. PCT/IE2008/000040 on Apr. 4, 2008, now Pat. No. 9,114,071.

(60) Provisional application No. 61/006,498, filed on Jan. 16, 2008, provisional application No. 60/907,490, filed on Apr. 4, 2007.

(51) Int. Cl.
A61K 9/50    (2006.01)
A61K 31/439  (2006.01)
A61K 38/28   (2006.01)
A61K 39/00   (2006.01)
A61K 31/635  (2006.01)
A61K 45/06   (2006.01)
A61K 31/436  (2006.01)
A61K 38/13   (2006.01)
A61K 9/00    (2006.01)

(52) U.S. Cl.
CPC .......... A61K 9/5073 (2013.01); A61K 9/0053 (2013.01); A61K 9/50 (2013.01); A61K 9/5015 (2013.01); A61K 9/5026 (2013.01); A61K 9/5042 (2013.01); A61K 9/5047 (2013.01); A61K 9/5057 (2013.01); A61K 9/5089 (2013.01); A61K 31/436 (2013.01); A61K 31/439 (2013.01); A61K 31/635 (2013.01); A61K 38/13 (2013.01); A61K 38/28 (2013.01); A61K 39/0005 (2013.01); A61K 45/06 (2013.01); A61K 2039/55583 (2013.01)

(58) Field of Classification Search
CPC .... A61K 9/5073; A61K 31/439; A61K 38/28; A61K 39/0005; A61K 9/5042; A61K 9/5089; A61K 31/635; A61K 45/06; A61K 9/0053; A61K 9/50; A61K 38/13; A61K 9/5047; A61K 9/5026; A61K 31/436; A61K 9/05
See application file for complete search history.

(56) References Cited

U.S. PATENT DOCUMENTS

| 3,971,852 A | 7/1976 | Brenner et al. |
| 4,279,632 A | 7/1981 | Frosch et al. |
| 4,379,454 A | 4/1983 | Campbell et al. |
| 4,388,307 A | 6/1983 | Cavanak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,401,502 A | 3/1995 | Wunderlich et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,498,439 A | 3/1996 | Bonner |
| 5,500,224 A | 3/1996 | Vranckx et al. |
| 5,510,118 A | 4/1996 | Bosch et al. |

(Continued)

FOREIGN PATENT DOCUMENTS

| AU | 1977031116 | 12/1976 |
| AU | 627220 B2 | 8/1992 |

(Continued)

OTHER PUBLICATIONS

Severin et al. (Therapy with Budesonide in Patients with Refractory Sprue, Digestion 2006; 73:60-68).*
Of M. Rodriguez et al. ( Acta Technologiae et Legis Medicamenti, vol. XI, N. 1,2000, Colonic budesonide delivery from ph-dependent microcapsules containing lipidic cores, 45-52.*
Al-Meshal et al., "Oral administration of liposomes containing cyclosporine: a pharmacokinetic study," *International Journal of Pharmaceutics* 168:163-168, 1998.
Anderberg et al., "Sodium Caprate Elicits Dilatations in Human Intestinal Tight Junctions and Enhances Drug Absorption by the Paracellular Route," *Pharmaceutical Research* 10(6):857-864, 1993.

(Continued)

*Primary Examiner* — Snigdha Maewall
(74) *Attorney, Agent, or Firm* — Klarquist Sparkman, LLP

(57) ABSTRACT

The present application provides a method for treating or preventing Celiac disease. In one embodiment the method comprises administering to a patient in need thereof a composition comprising minicapsules, wherein the minicapsules comprise a steroid in a liquid, semi-solid or solid core, the minicapsules having release profiles to release the steroid in an active form at one or more sites along the gastrointestinal tract, the one or more sites comprising the proximal small intestine beginning at the duodenum and ending at the ileum. In a related embodiment the method comprises administering budesonide to a patient in need thereof in a pre-solubilized drug delivery format.

32 Claims, 19 Drawing Sheets

(56) References Cited

U.S. PATENT DOCUMENTS

| | | |
|---|---|---|
| 5,589,455 A | 12/1996 | Woo |
| 5,645,856 A | 7/1997 | Lacy et al. |
| 5,650,232 A | 7/1997 | Glenn et al. |
| 5,665,386 A | 9/1997 | Benet et al. |
| 5,795,590 A | 8/1998 | Kiefer et al. |
| 5,827,531 A | 10/1998 | Morrison et al. |
| 5,843,347 A | 12/1998 | Nguyen et al. |
| 5,851,275 A | 12/1998 | Amidon et al. |
| 5,871,774 A | 2/1999 | Lemelson |
| 5,882,680 A | 3/1999 | Suzuki et al. |
| 5,914,132 A | 6/1999 | Kelm et al. |
| 6,022,562 A | 2/2000 | Autant et al. |
| 6,113,936 A | 9/2000 | Takebayashi et al. |
| 6,121,234 A | 9/2000 | Benet et al. |
| 6,146,663 A | 11/2000 | Bissery et al. |
| 6,166,044 A * | 12/2000 | Sandborn et al. ............ 514/343 |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,569,463 B2 | 5/2003 | Patel et al. |
| 6,585,997 B2 | 7/2003 | Moro et al. |
| 6,761,903 B2 | 7/2004 | Chen et al. |
| 6,923,988 B2 | 8/2005 | Patel et al. |
| 6,972,132 B1 | 12/2005 | Kudo et al. |
| 7,267,813 B2 | 9/2007 | Watanabe et al. |
| 7,374,779 B2 | 5/2008 | Chen et al. |
| 8,663,692 B1 | 3/2014 | Muller et al. |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 7/2002 | Darder |
| 2003/0045516 A1 | 3/2003 | Luly et al. |
| 2003/0055028 A1 | 3/2003 | Stergiopoulos et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1* | 9/2003 | Patel et al. .................... 424/465 |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2004/0230183 A1 | 11/2004 | Breegi et al. |
| 2005/0037077 A1 | 2/2005 | Legrand et al. |
| 2005/0095288 A1 | 5/2005 | Honea |
| 2005/0249807 A1 | 11/2005 | Brown et al. |
| 2006/0018965 A1* | 1/2006 | Moodley et al. ............ 424/470 |
| 2006/0034937 A1 | 2/2006 | Patel |
| 2006/0135441 A1 | 6/2006 | Khodadoust et al. |
| 2006/0222701 A1 | 10/2006 | Kulkarni et al. |
| 2007/0154554 A1 | 7/2007 | Burgermeister et al. |
| 2007/0292523 A1 | 12/2007 | Moodley et al. |
| 2008/0020018 A1 | 1/2008 | Moodley et al. |
| 2008/0107694 A1 | 5/2008 | Trogden et al. |
| 2008/0113031 A1 | 5/2008 | Moodley et al. |
| 2008/0311201 A1 | 12/2008 | Der-Yang et al. |
| 2008/0318912 A1 | 12/2008 | Fox et al. |
| 2010/0136105 A1 | 6/2010 | Chen et al. |
| 2010/0203120 A1 | 8/2010 | Coulter |
| 2010/0297221 A1 | 11/2010 | Coulter |

FOREIGN PATENT DOCUMENTS

| | | |
|---|---|---|
| CA | 2170748 | 8/1994 |
| CA | 2376261 | 6/2000 |
| CN | 1557283 | 12/2004 |
| DE | 19848849 | 10/1998 |
| EP | 0396425 | 11/1990 |
| EP | 0525731 | 2/1993 |
| EP | 0550067 | 7/1993 |
| EP | 0621775 | 11/1994 |
| EP | 0778083 | 6/1997 |
| EP | 0922451 | 6/1999 |
| EP | 0813876 | 3/2002 |
| JP | A-58 013508 | 1/1983 |
| JP | A-58 077810 | 5/1983 |
| JP | 59-088420 | 5/1984 |
| JP | A-61 151119 | 7/1986 |
| JP | 64-000015 | 1/1989 |
| JP | 7247215 A | 9/1995 |
| JP | 2000-247911 | 9/2000 |
| JP | 2000-302654 | 10/2000 |
| WO | WO 90/06775 | 6/1990 |
| WO | WO 93/00063 | 1/1993 |
| WO | WO 96/36322 | 11/1996 |
| WO | WO 97/02017 | 1/1997 |
| WO | WO 97/25980 | 7/1997 |
| WO | WO 98/18610 | 5/1998 |
| WO | WO 98/50018 | 11/1998 |
| WO | WO 99/06024 | 2/1999 |
| WO | WO 99/13914 | 3/1999 |
| WO | WO 00/33862 | 6/2000 |
| WO | WO 00/69420 | 11/2000 |
| WO | WO 01/08666 | 2/2001 |
| WO | WO 01/37808 | 5/2001 |
| WO | WO 01/51008 | 7/2001 |
| WO | WO 01/80831 | 11/2001 |
| WO | WO 03/018134 | 3/2003 |
| WO | WO 03/020243 | 3/2003 |
| WO | WO 03/030878 | 4/2003 |
| WO | WO 03/056938 | 7/2003 |
| WO | WO 03/068196 | 8/2003 |
| WO | WO 2004/022220 | 3/2004 |
| WO | WO 2004/052339 | 6/2004 |
| WO | WO 2004/064997 | 8/2004 |
| WO | WO 2005/020993 | 3/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/002365 | 1/2006 |
| WO | WO 2006/026592 | 3/2006 |
| WO | WO 2006/110802 | 10/2006 |
| WO | WO 2007/012478 | 2/2007 |
| WO | WO 2007/014445 | 2/2007 |
| WO | WO 2007/018943 | 2/2007 |
| WO | WO 2007/095092 | 8/2007 |

OTHER PUBLICATIONS

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J. Pharm. Pharmaceut. Sci.* 6(1):33/66/2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Gao et al., "Physiochemical characterization and evaluation of a microemulsion system for oral delivery of cyclosporin A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Kim et al., "Once-a-Day Oral Dosing Regimen of Cyclosporin A: Combined Therapy of Cyclosporin A Premicroemulsion Concen-

(56) References Cited

OTHER PUBLICATIONS trates and Enteric Coated Solid-State Premicroemulsion Concentrates," *Pharmaceutical Research* 18(4):454-459, 2001.

Lawrence, "Novel topical therapies for distal colitis," *World Journal of Gastrointestinal Pharmacology and Therapeutics* 1(5):87-93, Oct. 6, 2010.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

McGinity et al., Aqueous Polymeric Coatings for Pharmaceuticals Dosage Forms, *Marcel Dekker, Inc.*, 1997.

Milojevic et al., "Amylose as a coating for drug delivery to the colon: Preparation and in vitro evaluation using 5-aminosalicylic acid pellets," *Journal of Controlled Release* 38:75-84, 1996.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Ribeiro et al., "Microencapsulation of lipophilic drugs in chitosan-coated alginate microspheres," *International Journal of Pharmaceutics* 187:115-123, 1999.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Non-Final Office Action issued in U.S. Appl. No. 11/236,549 dated Oct. 6, 2010.

Final Office Action issued in U.S. Appl. No. 11/236,549 dated Apr. 1, 2011.

Non-Final Office Action issued in U.S. Appl. No. 11/236,549 dated Jul. 15, 2011.

Final Office Action issued in U.S. Appl. No. 11/236,549 dated Mar. 15, 2012.

Non-Final Office Action issued in U.S. Appl. No. 11/663,836 dated Feb. 23, 2011.

Non-Final Office Action issued in U.S. Appl. No. 11/663,834 dated May 13, 2009.

Non-Final Office Action issued in U.S. Appl. No. 11/663,834 dated Mar. 3, 2010.

Final Office Action issued in U.S. Appl. No. 11/663,834 dated Jun. 17, 2011.

Non-Final Office Action issued in U.S. Appl. No. 11/663,832 dated Aug. 3, 2009.

Final Office Action issued in U.S. Appl. No. 11/663,832 dated Jun. 9, 2010.

Non-Final Office Action issued in U.S. Appl. No. 11/663,832 dated Jul. 8, 2011.

Final Office Action issued in U.S. Appl. No. 11/663,832 dated Jun. 6, 2012.

Non-Final Office Action issued in U.S. Appl. No. 12/594,534 dated Mar. 30, 2012.

Final Office Action issued in U.S. Appl. No. 12/594,534 dated Aug. 27, 2012.

Non-Final Office Action issued in U.S. Appl. No. 12/594,553 dated Apr. 23, 2012.

Final Office Action issued in U.S. Appl. No. 12/594,553 dated Sep. 10, 2012.

Rodriguez et al., "Colonic budesonide delivery from ph-dependent microcapsules containing lipidic cores," *Acta Technologiae et Legis Medicamenti* XI(1):45-52, 2000.

Madene et al., "Flavour encapsulation and controlled release—a review," *International Journal of Food Science and Technology* 41:1-21, 2006.

Non-Final Office Action from co-pending U.S. Appl. No. 12/594,542 dated Oct. 5, 2012.

Final Office Action from co-pending U.S. Appl. No. 12/594,553 dated Sep. 10, 2012.

Non-Final Office Action from co-pending U.S. Appl. No. 13/321,149 dated Nov. 9, 2012.

Non-Final Office Action from co-pending U.S. Appl. No. 13/441,780 dated Nov. 28, 2012.

Brooker et al., "Long-Acting Steroid Injection after Endoscopic Dilation of Anastomotic Crohn's Strictures May Improve the Outcome: A Retrospective Case Series," *Endoscopy* 35(4):333-337, 2003.

Klausner et al., "Expandable gastroretentive dosage forms," *Journal of Controlled Release* 90:143-162, 2003.

Lee et al. "Preliminary experience with endoscopic intralesional steroid injection therapy for refractory upper gastrointestinal strictures," *Gastrointestinal Endoscopy*, 41(6): 598-601, 1995.

DeGuzman et al. "Endoscopic treatment of benign extra-esophageal gastrointestinal tract strictures via combined pneumatic dilation and interlesional steroid injection," *Stomach and Duodenum*, 43(4): 349, 1996.

Pochron et al. "A Prospective Randomized Controlled Trial of Endoscopic Steroid Injection Therapy for Recurrent Esophageal Peptic Strictures," *Gastrointestinal Endoscopy*, 59(5): 112, 2004.

Rutgeerts et al., "A comparison of Budesonide with Prednisolone for Active Crohn's Disease," *The New England Journal of Medicine*, 331(13): 842-845, 1994.

Akhlaghi et al., "Distribution of Cyclosporin in Organ Transplant Recipient,"*Clin. Pharmacokinet.*, 41(9): 615-637, 2002.

Asghar et al., "Multiparticulate Formulation Approach to Colon Specific Drug Delivery: Current Perspectives,"*J. Pharmaceut. Sci.*, 9(3): 327-338, Nov. 16, 2006.

Cannon et al., "Chapter 11: Emulsions, Microemulsions, and Lipid-Based Drug Delivery Systems for Drug Solubilization and Delivery—Part II: Oral Applications,"*Water-Insoluble Drug Formulation: Second Edition*, CRC Press, pp. 227-254, 2008.

Dhara et al., "Stability of Sodium Dodecyl Sulfate Micelles in the Presence of a Range of Water-Soluble Polymers: A Pressure-Jump Study,"*J. Phys. Chem.*, vol. 105, pp. 7133-7138, 2001.

Feagan et al., "Low-Dose Cyclosporine for the treatment of Crohn's disease,"*The New England Journal of Medicine*, 330(26): 1846-1851, Jun. 30, 1994.

French et al., "Evaluation of the Physicochemical Properties and Dissolution Characteristics of Mesalamine: Relevance to Controlled Intestinal Drug Delivery,"*Pharmaceutical Research*, 10(9): 1285-1286, Feb. 10, 1993.

Gibson, "Lipid-Based Excipients for Oral Drug Delivery,"*Oral Lipid-Based Formulations: Enhancing the Bioavailability of Poorly Water-Soluble Drugs: Drugs and the Pharmaceutical Sciences*, vol. 170, pp. 33-61, 2007.

Greener et al., "Interaction of Anionic Surfactants with Gelatin: Viscosity Effects,"*Macromolecules*, vol. 20, pp. 2490-2498, 1987.

Holmberg et al., *Surfactants and Polymers in Aqueous Solution: Second Edition*, 547 pages, 2002.

Homar et al., "Influence of polymers on the bioavailability of microencapsulated celecoxib,"*Journal of Microencapsulation*, 24(7): 621-633, Nov. 2007.

Keck, "Cyclosporine Nanosuspensions: Optimised Size Characterization & Oral Formulations,"*Dissertation submitted to Freien Universitat*, Berlin, 2006.

Liu et al., "Chapter 12: Micellization and Drug Solubility Enhancement,"*Water-Insoluble Drug Formulation: Second Edition*, CRC Press, pp. 255-272, 2008.

McGinity et al., "Enteric Film Coating of Soft Gelatin Capsules,"*Drug Delivery Tech.*, 3(6): 7 pages, Sep. 6, 2003.

Muller et al., "Competitive Adsorption of Gelatin and Sodium Dodecylbenzenesulfonate at Hydrophobic Surfaces,"*Langmuir*, vol. 14, pp. 3107-3114, Mar. 17, 1998.

Office Action issued by Japan Patent Office for Japanese Patent Application No. 2006-507572 on Sep. 24, 2014, 16 pages.

(56) References Cited

OTHER PUBLICATIONS

Qiu et al., *Developing solid Oral Dosage forms: Pharmaceutical Theory & Practice, Academic Press*, p. 445, 2009.
Reich, "Chapter 11: Formulation and physical properties of soft capsules,"*Pharmaceutical Capsules: Second Edition*, ed. Podczeck and Jones, pp. 201-212, 2004.
Tang et al., "Coating Multiparticulates for Sustained Release,"*Am. J. Drug Deliv.*, 3(1): 17-28, 2005.
van Deventer, "Small therapeutic molecules for the treatment of inflammatory bowel disease,"*Gut*, 50(3): 47-53, 2002.
Wesley et al., "Structure of Polymer Surfactant Complexes Formed by Poly(2-(dimethylamino)ethyl methacrylate) and Sodium Dodecyl Sulfate,"*Langmuir*, vol. 18, pp. 5704-5707, Apr. 30, 2002.

\* cited by examiner

ORAL PHARMACEUTICAL COMPOSITION

CROSS REFERENCE TO RELATED APPLICATIONS

This is a continuation of U.S. patent application Ser. No. 12/594,542, filed May 26, 2010 now U.S. Pat. No. 9,114,071, which is the U.S. National Stage of International Application No. PCT/IE2008/000040, filed Apr. 4, 2008, which was published in English under PCT Article 21(2), which in turn claims the benefit of U.S. Provisional Application No. 61/006,498, filed Jan. 16, 2008, and U.S. Provisional Application No. 60/907,490, filed Apr. 4, 2007, all of which are incorporated herein in their entirety.

The present invention relates to multiple minicapsule or minisphere modified release compositions.

INTRODUCTION

A fundamental principle that underlies pharmaco-therapeutic intervention is the need for a drug molecule to interact with its specific receptor. Addressing this need, pharmaceutical formulation technology has developed methods to enhance the solubility of drugs and to maintain solubilised drug molecules as single molecular entities.

The contents and medium in the gastro-intestinal tract (GIT) is primarily aqueous in nature. The solubility of drugs in the GIT is dependent on their physicochemical properties and is affected by the pH, bile salts, bacteria, water content, amongst other factors. Generally, depending on the local pH, water-soluble or hydrophilic drugs are readily soluble throughout the GIT whereas poorly water-soluble hydrophobic or lipophilic drugs are insoluble or have limited solubility in the GIT.

Various technologies have been developed to address enhancing the solubility of hydrophobic and lipophilic drugs. Further technologies have been developed to enhance or maintain the solubility of pH sensitive drugs to prevent precipitation in acid, neutral or basic environments.

Utilising traditional oral drug delivery technologies, colonic delivery has proven difficult, in particular for small molecule drugs with limited water solubility. This difficulty stems from the preference of hydrophobic or lipophilic drugs to aggregate in an aqueous environment. There, therefore, exists a need for a technology which will enable solubility equalisation of hydrophilic, hydrophobic or lipophilic drugs when released from an orally administered format regardless of where along the GIT the drug is released, including in the colon.

Controlled release formulations have been suited mainly to water-soluble drugs that conform with conventional pill or pellet forms and when released from such formats are readily soluble in the aqueous GIT environment. However, conventional forms have not facilitated hydrophobic or lipophilic drugs that are optimally formulated as non-powders, such as those that are formulated as various lipid-based or other solubility enhancing excipient-based liquid, semi-solid or solid formats. A technology to enable any compound to be released into any region of the GIT in a soluble form is desirable.

Lipid-based formulations have been developed to enhance the solubility of non-water soluble compounds and invariably take an oil, emulsion, a suspension, a waxy form, a colloid, liposome, or other non-powder or solid form. Additionally, lipid-based formulations have been utilized to enhance the permeability of compounds, including hydrophilic compounds, which do not pass readily from the intestine into the bloodstream. Such lipid based formulations have been administered to subjects as large soft-gel capsules. As large soft-gel capsules are soft and pliable and have a seam, they are unsuited to further processing, including coating with controlled release polymers. Even if such formats could be uniformly and effectively coated, once the controlled release coating is breached, the entire contents of the capsule would be released in a bolus-like effect. Without coating, the drug is released into the stomach in a quantity that may be above the therapeutic index and thus result in long term toxic side effects. The development of a controlled release technology to overcome the issues associated with the limiting large soft-gel capsule form is therefore desirable.

Another issue associated with many drugs relates to the fact that they are absorbed with different efficiencies as they pass from the small intestine through to the colon. In some instances, a poorly water-soluble drug formulated either in a lipid-based non-powder or an enhanced solubility powder form demonstrates absorption in the small intestine but not in the colon. In some instances, apart from enhancing solubility some lipid based formulations, such as various emulsion-based formulations also enhance intestinal absorption, of both water-soluble and poorly water-soluble drugs, through enhancing interaction with bile salts and other endogenous emulsifiers to form drug micelles which are more readily absorbed, mainly in the upper small intestine.

In general, pH-dependent systems for targeting a pharmaceutical active release to a specific location in the intestine can be unreliable for a number of reasons. For example, premature release and associated systemic absorption of the parent compound may result from a proximal intestinal pH at or above the critical triggering pH. Alternatively, incomplete or minimal release may result from the occurrence of the critical pH at a site distal of the affected area. Nugent et al, Gut 48, pages 571-577 (2001), reviews the potential problems of the pH-dependent distal gut delivery approach, pointing out that the existence of inter-subject variations in intestinal pH.

U.S. Pat. No. 5,716,648 describes an oral composition that relies on a pH-dependent soluble coating, but also includes a pH-regulating alkaline material to attempt to compensate for patients with "subnormal intestinal pH." Other approaches include those described in U.S. Pat. No. 5,866,619, which is generally directed to a non-pH-dependent colonic drug-delivery system involving a saccharide-containing polymer, which is enzymatically degraded by the colon. Another example is provided by U.S. Pat. No. 6,506,407, which generally describes a colon-specific drug-releasing system that combines a pH-dependent outer coating with the inclusion of a saccharide substrate, which upon enzymatic breakdown by enterobacteria produces an organic acid that subsequently dissolves an acid-soluble inner coating.

Still other examples are described in U.S. Application No. 2002/0098235, which describes the use of multiple pH-dependent coatings to reduce the impact of coating fractures. U.S. Application No. 2001/0055616 describes a pellet formulation for treating intestinal tract conditions, which utilizes a pH-dependent enteric coating to target release from a non-gel-forming drug-containing polymeric matrix core. U.S. Application 2001/0036473 describes a pH-dependent coating on a hydroxypropylmethylcellulose capsule for enteric and colonic delivery. U.S. Application No. 2001/0026807 describes various coatings, including pH-dependent materials, redox-sensitive materials, and materials subject to breakdown by bacteria, on a starch capsule to achieve colonic delivery.

The various strategies for targeting orally administered drugs to the colon include covalent linkage of a drug with a carrier, including those that enhance stability as well as perhaps increase hydrophilicity; coating with pH-sensitive polymers; formulation of timed released systems, exploitation of carriers that are degraded specifically by colonic bacteria; bioadhesive systems; and osmotic controlled drug delivery systems. Various prodrugs (sulfasalazine, ipsalazine, balsalazine and olsalazine) have been developed that are aimed to deliver 5-amino salicylic acid (5-ASA) for localized chemotherapy of inflammatory bowel disease (IBD). Microbially degradable polymers especially azo crosslinked polymers have been investigated for use in targeting of drugs to colon. Certain plant polysaccharides such as amylose, inulin, pectin and guar gum remains unaffected in the presence of gastrointestinal enzymes and pave the way for the formulation of colon targeted drug delivery systems. Additionally, combinations of plant polysaccharides with crustacean extract, including chitosan or derivatives thereof, are proving of interest for the development of colonic delivery systems.

The concept of using pH as a trigger to release a drug in the colon is based on the pH conditions that vary continuously down the gastrointestinal tract. Time-dependent drug delivery systems have been developed that are based on the principle to prevent release of drug until 3-4 h after leaving the stomach. Redox sensitive polymers and bioadhesive systems have also been exploited to deliver the drugs into the colon.

The pH-dependent systems exploit the generally accepted view that pH of the human GIT increases progressively from the stomach (pH 1-2 which increases to 4 during digestion), small intestine (pH 6-7) at the site of digestion and it increases to 7-8 in the distal ileum. The coating of pH-sensitive polymers to the tablets, capsules or pellets provide delayed release and protect the active drug from gastric fluid. The polymers used for colon targeting, however, should be able to withstand the lower pH values of the stomach and of the proximal part of the small intestine and also be able to disintegrate at the neutral of slightly alkaline pH of the terminal ileum and preferably at the ileocecal junction.

Lorenzo-Lamosa et al. (Design of microencapsulated chitosan microspheres for colonic drug delivery. J Control Rel, 52: 109-118, 1998) prepared and demonstrated the efficacy of a system, which combines specific biodegradability and pH dependent release behaviour. The system consists of chitosan microcores entrapped within acrylic microspheres containing diclofenac sodium as model drug. The drug was efficiently entrapped within the chitosan microcores using spray drying and then microencapsulated into Eudragit™ L-100 and Eudragit™ S-100 using an oil-in-oil solvent evaporation method. Release of the drug from chitosan multireservoir system was adjusted by changing the chitosan molecular weight or the type of chitosan salt. Furthermore, by coating the chitosan microcores with Eudragit™, perfect pH-dependent release profiles were attained. Similarly, melt extrusion of a drug with various Eudragit polymers in the presence or absence of chitosan, gelling agents or the like has the potential to enable colon-specific release.

Polysaccharides, the polymer of monosaccharides retains their integrity because they are resistant to the digestive action of gastrointestinal enzymes. The matrices of polysaccharides are assumed to remain intact in the physiological environment of stomach and small intestine but once they reach in the colon, they are acted upon by the bacterial polysaccharidases and results in the degradation of the matrices. This family of natural polymers has an appeal to the area of drug delivery as it is comprised of polymers with a large number of derivatizable groups, a wide range of molecular weights, varying chemical compositions, and for the most part, a low toxicity and biodegradability, yet a high stability. The most favourable property of these materials is that they are already approved as pharmaceutical excipients. A large number of polysaccharides such as amylose, guar gum, pectin, chitosan, inulin, cyclodextrins, chondroitin sulphate, dextrans and locust bean gum as well as modifications thereof have been investigated for their use in colon targeted drug delivery systems. The most important fact in the development of polysaccharide derivatives for colon targeted drug delivery is the selection of a suitable biodegradable polysaccharide. As these polysaccharides are usually soluble in water, they must be made water insoluble by crosslinking or hydrophobic derivatisation.

Guar gum is hydrophilic in nature and swells in cold water forming viscous colloidal dispersions or sols. This gelling property retards release of the drug from the dosage form as well as it is susceptible to degradation in the colonic environment. Homogenized and diluted feces from human source were incubated with the guar gum to investigate the degradation of polysaccharide by intestinal microflora. It produced a rapid decrease in viscosity and fall in pH while no such results were observed when it was incubated with autoclaved fecal homogenates. Guar gum was crosslinked with increasing amounts of trisodium trimetaphosphate to reduce its swelling properties for use as a vehicle in oral delivery formulations. As a result of the crosslinking procedure guar gum lost its non-ionic nature and became negatively charged. This was demonstrated by methylene blue adsorption studies and swelling studies in sodium chloride solutions with increasing concentrations in which the hydrogels' network collapsed (Gliko-Kabir, I., Yagen, B., Penhasi, A. and Rubinstein, A., Phosphated crosslinked guar for colon-specific drug delivery. I. Preparation and physicochemical characterization. J Control Rel, 63: 121-127, 2000). Crosslinked guar gum products were analysed to check the efficacy as colon-specific drug carrier and it was found that the product which was crosslinked with 0.1 molar equivalent of trisodium trimetaphosphate was able to prevent the release of 80% of its hydrocortisone load for at least 6 h in PBS (pH 6.4). When a mixture of α-galactosidase and β-mannanase was added to the buffer solution, an enhanced release was observed. In vivo degradation studies in the rat caecum showed that despite the chemical modification of guar gum, it retained its enzyme-degrading properties in a crosslinker concentration dependent manner. A novel tablet formulation for oral administration using guar gum as the carrier and indomethacin as a model drug has been investigated for colon targeted drug delivery using in vitro methods. Drug release studies under conditions simulating the gastrointestinal transit have shown that guar gum protects the drug from being released completely in the physiological environment of stomach and small intestine. Studies in pH 6.8 PBS containing rat caecal contents have demonstrated the susceptibility of guar gum to the colonic bacterial enzyme action with consequent drug release (Rama Prasad, Y. V., Krishnaiah, Y. S. R. and Satyanarayana, S., In vitro evaluation of guar gum as a carrier for colon-specific drug delivery. J Control Rel, 51: 281-287, 1998).

Colon-specific drug delivery may be possible by the application of dried amylose films to pharmaceutical formulations. Amylose, one of the major fractions of starch, possesses the ability to form films through gelation, when prepared under appropriate conditions. The microstructure of the film is potentially resistant to the action of pancreatic α-amylase but is digested by amylases of the colonic microflora. However, under simulated gastrointestinal conditions, coatings made solely of amylose will become porous and allow drug release. Incorporation of insoluble polymers into the amylose film, to control amylose swelling, provides a solution to this problem. A range of cellulose and acrylate based copolymers were assessed, of which a commercially available ethylcellulose (Ethocel) was found to control the swelling most effectively. The in vitro dissolution of various coated pellets under simulated gastric and small intestinal conditions, using commercially available pepsin and pancreatin was determined and demonstrated the resistance of the amylose-Ethocel coat (1:4) to such conditions over a period of 12 h (Milojevic, S., Newton, J. M., Cummings, J. H., Gibson, G. R., Botham, R. L., Ring, S. C., Stockham, M. and Allwood, M. C., Amylose as a coating for drug delivery the colon: Preparation and in vitro evaluation using 5-aminosalicylic acid pellets. J Control Rel, 38: 75-84, 1996).

Chitosan is a high molecular weight polycationic polysaccharide derived from naturally occurring chitin by alkaline deacetylation. Chitosan has favourable biological properties such as nontoxicity, biocompatibility and biodegradability. Similar to other polysaccharides it also undergoes degradation by the action of colonic microflora and hence poses its candidature for colon targeted drug delivery. Tozaki et al. (Tozaki, H., Odoriba, T., Okada, N., Fujita, T., Terabe, A., Suzuki, T., Okabe, S., Murnishi, S. and Yamamoto, A., Chitosan capsules for colon-specific drug delivery: enhanced localization of 5-aminosalicylic acid in the large intestine accelerates healing of TNBS-induced colitis in rats. J Control Rel, 82, 51-61, 2002) developed colon-specific insulin delivery with chitosan capsules. In vitro drug release experiments from chitosan capsules containing 5(6)-carboxyfluorescein (CF) were carried out by rotating basket method with slight modifications. The intestinal absorption of insulin was evaluated by measuring the plasma insulin levels and its hypoglycaemic effects after oral administration of the chitosan capsules containing insulin and additives. Little release of CF from the capsules was observed in an artificial gastric juice (pH 1), or in an artificial intestinal juice (pH 7). However, the release of CF was markedly increased in the presence of rat caecal contents. This group further evaluated colon-specific insulin delivery using chitosan capsules. It was found that these were stable in the stomach and small intestine but degraded by microorganism in rat caecal contents upon entering into the colon proving their utility as carriers for colon targeted drug delivery of peptide and non-peptide drugs.

Pectin, a predominately linear polymer of mainly α-(1→4)-linked D-polygalacturonic acid residues, has been widely investigated as a colon-specific drug delivery entity. It can be broken down by pectinase enzymes produced by anaerobic bacteria of the colon and can control drug release by this principle (Atyabi et al, Carbohyd. Polymers, 2005, 61, 39-51). As pectin is water soluble, efficient colonic delivery requires that the solubility is controlled. Liu et al. (Liu et al, Biomaterials 2003, 24, 3333-3343) demonstrated promising drug delivery potential when pectin was combined with water-insoluble polymers. Previously, Wakerly et al. (Wakerly et al., Pharm. Res., 1996, 13 (8), 1210-1212) identified that a combination of ethylcellulose and pectin could provide protection of a drug in the upper GI tract while allowing enzymatic breakdown and drug release in the colon. Wei et al. (Wei et al., PDA Journal of Pharmaceutical Science and Technology, Vol 61, No. 2, March-April 2007, 121-130) demonstrated that colon-specific controlled release of the water-soluble anticancer agent, 5-fluorouracil, was possible when incorporated into pellets that were coated with various proportions of pectin and ethycellulose (Surlease®).

Redox potential is an expression of the total metabolic and bacterial activity in the colon and it is believed to be insensitive to dietary changes. The mean redox potential in proximal small bowel is −67±90 my, in the distal small bowel is −196±97 my and in the colon is −145±72 my. Thus, microflora-induced changes in the redox potential can be used as a highly selective mechanism for targeting to the colon. Bragger et al. (Investigations into the azo reducing activity of a common colonic microorganism. *Int J Pharm*, 157: 61-71, 1997) carried out investigations into the azo reducing activity, which could enlighten some factors affecting the bacterial reduction (cleavage) of azo compounds. A common colonic bacterium, *Bacteroides fragilis* was used as test organism and the reduction of azo dyes amaranth, Orange II, tartrazine and a model azo compound, 4,4'-dihydroxyazobenzene were studied. It was found that the azo compounds were reduced at different rates and the rate of reduction could be correlated with the redox potential of the azo compounds. Disulphide compounds can also undergo degradation due to the influence of redox potential in the colon. Noncrosslinked redox-sensitive polymers containing an azo and/or a disulfide linkage in the backbone have been synthesised (Schacht, E. and Wilding, I. R., Process for the preparation of azo- and/or disulfide-containing polymers. Patent: WO 9111175).

Controlled Release Polymers—Membrane-Controlled Dosage Forms

The GI residence time of the dosage forms is another important parameter for pH-dependent colon targeted drug delivery systems which is influenced by many physiological and other factors; nevertheless, there are some generally accepted GI residence values for various parts of the GIT. Most commonly used pH-dependent coating polymers are methacrylic acid copolymers, commonly known as Eudragit™ (Registered trademark of Evonik AG, Darmstadt, Germany). EUDRAGIT™ polymers (available from Evonik) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers that are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

Eudragit™ L100 and S100 are copolymers of methacrylic acid and methyl methacrylate. The ratio of carboxyl to ester groups is approximately 1:1 in Eudragit™ L100 and 1:2 in Eudragit™ S100. The polymers form salts and dissolve above pH 5.5 and disperse in water to form latex and thus avoid the use of organic solvents in the coating process. Eudragit™ L30D-55 is a ready to use aqueous dispersion of Eudragit™ L100-55. The water solubility of the Eudragit™ S depends on the ratio of free carboxyl groups to the ester groups. The critical factor that influences the performance of these polymers is the pH value at which dissolution occurs. Polymers with ionizable phthalic acid groups dissolve much faster and at a lower pH than those with acrylic or methacrylic acid groups. The presence of plasticizer and the nature of the salt in the dissolution medium also influence the dissolution rate of Eudragit™. In addition, the permeability of the film formed may depend on the type of solvent used to dissolve Eudragit™ (Dressman, J. B., Amidon, C., Reppas, C. and Shah, V. P., Dissolution testing as a prognostic tool for oral drug absorption: Immediate release dosage forms, Pharm Res, 15: 11-22, 1998.).

Variable combinations of the commercially available acrylic-, methacrylic-, ethylcellulose-based polymers (such as, but not limited to the Eudragit™ and Surelease® range), as well as other polymers with natural polysaccharides, including, but not limited to amylose, pectin and guar gum have the potential to customise how, where and when drugs are released from the underlying or embedded solid, semi-solid or liquid forms. There is a need for formulations which will enable the development of various combinations of controlled release polymers with solid, semi-solid or liquid drug formulations.

STATEMENTS OF INVENTION

The invention provides an oral composition comprising minicapsules wherein the minicapsules comprise one or more therapeutic or prophylactic substances in a liquid, semi-solid, or solid core, the minicapsules having release profiles to release the substance in an active form at one or more sites along the gastrointestinal tract. The term active pharmaceutical as used below refers to any suitable therapeutically and/or prophylactically active substance. The invention provides an oral pharmaceutical composition comprising minicapsules wherein the minicapsules comprise one or more active pharmaceutical compound in a liquid, semi-solid or solid core minicapsule format, the minicapsules having release profiles to release the active compound at one or more sites along the gastrointestinal tract where absorption is maximized or therapeutic efficacy is maximized. Importantly, the invention ensures that the molecule, regardless of its inherent physicochemical property, when released from the minicapsule is in a soluble form or is readily soluble in the aqueous GIT environment.

The active pharmaceutical compound(s) may be a small molecule, protein, peptide, nucleic acid, carbohydrate, live organism, component derived from an organism, or any derivative thereof.

The minicapsule may have one layer and may be solid throughout. Alternatively, the minicapsule may have two layers comprising a solid outer shell layer encapsulating a liquid, semi-solid or solid core. For example, the minicapsule may have three layers comprising a solid outer shell layer; a solid, semi-solid or liquid middle buffer layer; and a liquid, semi-solid or liquid core.

The minicapsules may be modified to enable modified release of the active(s). For example, a modified release coating may be applied to the outer shell layer of the minicapsule. Alternatively, an outer shell layer of the minicapsule may be modified to achieve modified release. In other formats, the minicapsule core or entirety may control the rate of active compound release. For example a buffer layer of the minicapsule may be modified to achieve modified release. Alternatively, the liquid, semi-liquid or solid core of the minicapsule may be modified to achieve modified release. For example, polymeric materials may be used achieve modified release such as polymeric materials that are sensitive to one or more of pH, time, thickness, erosion, and bacterial breakdown.

The minicapsule may comprise of one layer containing one or more active pharmaceutical agent and that layer controls the release of the active pharmaceutical agent(s).

The active pharmaceutical agent may be in micronised or nanonised particles. The active pharmaceutical agent(s) may be in soluble form. Alternatively, the active pharmaceutical agent(s) may be in crystalline form or the active pharmaceutical agent(s) may be in amorphous form.

The active pharmaceutical agent(s) may be released along the gastrointestinal tract in a form that maximises systemic absorption. For example, the active pharmaceutical agent(s) may be released along the gastrointestinal tract in a form that maximises lymphatic absorption. Alternatively, the active pharmaceutical agent(s) may be released along the gastrointestinal tract in a form that maximises blood brain barrier absorption. Alternatively, the active pharmaceutical agent(s) may be released along the gastrointestinal tract in a form that maximises pre-systemic absorption. Alternatively, the active pharmaceutical agent(s) may be released along the gastrointestinal tract in a form that maximises local gastrointestinal activity. Alternatively, the active pharmaceutical agent(s) may be released along the gastrointestinal tract in a form that maximises gastrointestinal lumen activity. Alternatively, the active pharmaceutical agent(s) may be released along the gastrointestinal tract in a form that maximises chronotherapy. In all cases, the active pharmaceutical agent(s) is released in such that is in soluble when released or is readily soluble in the local GIT environment.

The active pharmaceutical agent(s) may be retained in the gastric region for prolonged periods.

A pharmaceutical active may be in two or more formats, a solid minicapsule form soluble in the small intestine or is pre-solubilised for release in the colon and/or ileum.

A composition in accordance with the invention may have more than one active pharmaceutical agent which is released at one or more region of the gastrointestinal tract. For example, one active may be in a solid minicapsule form soluble in the small intestine while the other active may be pre-solubilised for release in the colon and/or ileum.

The active pharmaceutical agent(s) may be in a solubility enhanced format which, when released in the colon, is readily absorbed.

The active pharmaceutical agent(s) may be a small molecule.

The active pharmaceutical agent(s) may be a conjugated small molecule or derivative thereof to enhance permeability, increase lipophilicity, and/or increase hydrophilicity or the like.

The active pharmaceutical agent(s) may be a biopharmaceutical such as a peptide, protein, nucleic acid, carbohydrate, conjugates or derivatives thereof to enhance permeability, increase lipophilicity, increase stability, reduce immunogenicity and/or increase hydrophilicity or the like.

The composition may contain a protectant such as a proteolytic enzyme inhibitor.

The composition may contain an adhesive entity such as a muco- or bio-adhesive.

The composition may contain an antigen(s) and/or an adjuvant(s) to induce an intestinal mucosal or a systemic immune response.

The composition may have controlled release as a factor of the shell coating(s). For example controlled release may be a factor of the shell composition. Alternatively, controlled release may be a factor of the core. The controlled release may be a factor of the shell coating and/or the shell composition and/or the core constituents.

The minicapsules may be administered in a hard gelatine capsule, a sprinkle, a tablet or via a feeding tube such as a nasal gastric tube or a duodenal feeding tube.

The minicapsules may further comprise excipients to maximize solubility of active pharmaceutical compound(s)

The minicapsules may further comprise excipients to maximize permeability of the active pharmaceutical compound(s) in the small intestine.

The composition may further comprise excipients to maximize permeability of the active pharmaceutical compound(s) in the ileum, including, but not limited to sodium caprate, sodium dodecanoate, sodium palmitate, SNAC, chitosan and derivatives thereof, fatty acids, fatty acid esters, polyethers, bile salts, hydroxylase inhibitors, antioxidants and/or nitric oxide donors, including nitric oxide donor groups covalently attached to various active pharmaceutical ingredients.

The composition may further comprise excipients to maximize permeability of the active pharmaceutical compound(s) in the colon including, but not limited to sodium caprate, sodium dodecanoate, sodium palmitate, SNAC, chitosan and derivatives thereof, fatty acids, fatty acid esters, polyethers, bile salts, hydroxylase inhibitors, antioxidants and/or nitric oxide donors, including nitric oxide donor groups covalently attached to various active pharmaceutical ingredients.

The composition may further comprise excipients to enhance the therapeutic potential of active pharmaceutical agents in the ileum and colon including, but not limited to absorption limiters, essential oils such as omega 3 oils, natural plant extracts such as neem, ion-exchange resins, bacteria degradable conjugation linkers such as azo bonds, polysaccharides such as amylose, guar gum, pectin, chitosan, inulin, cyclodextrins, chondroitin sulphate, dextrans, guar gum and locust bean gum, nuclear factor kappa B inhibitors, acids such as fumeric acid, citric acid and others, as well as modifications thereof.

The composition may further comprise excipients or other active pharmaceutical or other ingredients to enhance systemic bioavailability following absorption in the small intestine including efflux pump inhibitors, including, but not limited to PgP pump inhibitors, and metabolism inhibitors, including, but not limited to, cytochrome P450 3A inhibitors.

The composition may further comprise excipients to reduce systemic side effects associated with absorption in the small intestine including, but not limited to, antioxidants, such as curcuminoids, flavanoids or more specifically including curcumin, beta-carotene, α-tocopherol, ascorbate or lazaroid.

The pharmaceutical active may be in a solubilised or readily soluble liquid, semi-liquid or solid form.

The pharmaceutical active may be an immunosuppressive, for example cyclosporine A or tacrolimus or sirolimus or derivatives thereof.

The composition may provide sustained release of the immunosuppressive, in soluble or readily soluble form, throughout the entire length of the gastrointestinal tract.

The composition may facility release over 24 hours, or at different time periods throughout 24 hours.

The composition may facilitate absorption over 24 hours.

The composition may be used in the treatment of graft-versus-host disease, for example in the treatment of gastrointestinal graft-versus-host disease.

The pharmaceutical active immunosuppressive may be released throughout the colon and/or ileum.

The composition may be used in the treatment of inflammatory bowel disease.

The pharmaceutical active may be a hydroxylase inhibitor, for example a propyl hydroxylase inhibitor or an asparaginyl hydroxylase inhibitor.

The pharmaceutical active may be DMOG.

The pharmaceutical active may be hydralazine.

The pharmaceutical active may be FG4095.

The composition may be used in the treatment of inflammatory bowel disease.

The pharmaceutical active may be a plant extract.

The pharmaceutical active may be a marine extract.

The pharmaceutical active may be an essential oil.

The composition may be used in the treatment of inflammatory bowel disease.

The composition may be used in the treatment of irritable bowel syndrome.

The composition may be used in the treatment of constipation.

The composition may be used in the treatment of diarrhoea.

The pharmaceutical active may be a vaccine.

The pharmaceutical active may modulate oral tolerance. For example, the active entity may be gluten or a gluten derivative.

The composition may be used in the treatment of celiac disease.

The pharmaceutical active may modulate irritable bowel syndrome.

The pharmaceutical active may be a hydroxylase inhibitor.

The pharmaceutical active may be an ion channel blocker.

The pharmaceutical active may be a plant extract.

The pharmaceutical active may be an opioid, for example the pharmaceutical active may be morphine or morphine sulphate.

The opioid may be combined with an opioid-induced constipation modulator for example a peripheral opioid receptor antagonist. The peripheral opioid receptor antagonist may be methylnaltrexone. Alternatively, the peripheral opioid receptor antagonist may be naltrexone or naloxone.

The combination opioid and peripheral opioid receptor may be combined with an ion-channel blocker for example a calcium channel blocker. The calcium channel blocker may be nimodipine.

The composition may have an extended opioid effect and constipation may be limited.

The combination opioid and peripheral opioid receptor may be combined with an ion-channel blocker for example a calcium channel blocker. The calcium channel blocker may be nimodipine.

The composition may have an extended opioid effect, constipation may be limited and the product may be tamper-proofed.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION

Figure 1:
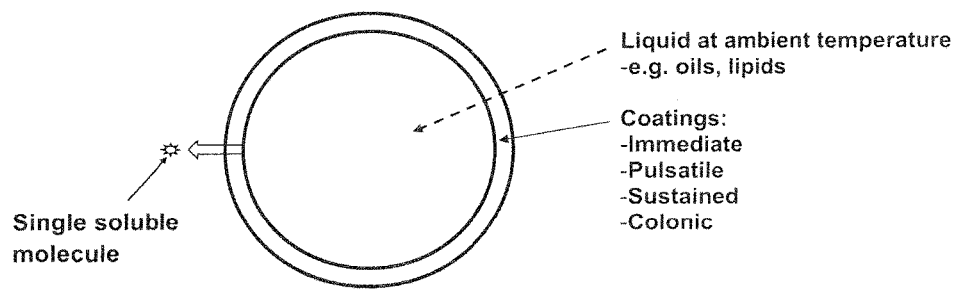
FIG. 1 is a schematic of a liquid-filled minicapsule, wherein the active is solubilised, with controlled release polymer coatings. The open arrow represents the release of a drug molecule into the external medium, where it is fully soluble when released (Format 1)

The controlled release of active pharmaceutical agents is only truly useful if the agent is available to interact with its receptor or site of action in an active form. Unless the agent is in a fully soluble form it is unlikely to interact with its intended receptor or exert its desired action. The invention is a drug delivery format that enables the release of an active(s) from the format in soluble or readily-soluble form.

As the invention permits the release of the active in soluble or readily-soluble form, it thus enables a true once-daily drug formulation, especially for a small molecule drug with poor water-solubility, possibly with limited stability or a short half-life, as the drug is absorbed not only in the small intestine but also in the colon.

The invention provides an oral drug delivery technology that permits the colon-specific release of pre- or readily-solubilised drugs in tandem with a controlled release formulation that permits release and absorption in the small intestine, ileum and/or colon of soluble or readily-soluble drug molecules to ensure true once-daily formulations for hydrophilic, hydrophobic or lipophilic small molecule drugs with variable stability.

As the invention is comprised of a multitude of separate minicapsules, either containing liquid, semi-solid or solid formulations, the invention enables the development of novel combination therapies in a single dosage form, each component of the combination having distinct release profiles, the release being inherent to the core formulation, the shell or the entirety of the minicapsule or some additional polymer coating thereon.

In addition to enabling once-daily delivery of the above classes of small molecules, colon delivery is advantageous as an effective drug delivery mechanism for certain drugs, including biopharmaceuticals and vaccines, drugs formulated for enhanced lymphatic absorptions as well as for enhanced treatment of diseases of colon (ulcerative colitis, Chron's disease, Gastro-Intestinal Graft Versus Host Disease (GI-GVHD), Irritable Bowel Syndrome, constipation, diarrhoea, carcinomas and other infections) whereby high local concentration can be achieved while minimizing side effects that occur because of release of drugs in the upper GIT or unnecessary systemic absorption. The colon is rich in lymphoid tissue, uptake of antigens into the mast cells of the colonic mucosa produces rapid local production of antibodies and this helps in efficient vaccine delivery (Sarasija, S. and Hota, A., Colon-specific drug delivery systems. *Ind J Pharm Sci*, 62: 1-8, 2000).

The colon is a site where a drug molecule, particularly but not exclusively hydrophilic, that has limited intestinal absorption may have an improved bioavailability. The colon is recognized as having a somewhat less hostile environment with less diversity and intensity of activity than the stomach and small intestine. Additionally, the colon has a longer retention time and appears highly responsive to agents that enhance the absorption of poorly absorbed drugs. Apart from retarding or targeting dosage forms, a reliable colonic drug delivery is also an important for the colonic absorption of perorally applied, undigested, unchanged and fully active peptide drugs. As the large intestine is relatively free of peptidases such special delivery systems will have a greater chance to get their drug sufficiently absorbed after peroral application.

Traditional dosage forms in which an immediate release (IR) dosage form is administered at periodic intervals typically gives rise to a pulsatile plasma profile, related to the time of ingestion and usually within a short period following such ingestion. Where release from the dosage form is rapid or 'immediate', the peak in the plasma drug concentration is observed after administration of each IR dose with troughs or low plasma concentrations obvious between consecutive administration time points. The pulsatile plasma profiles resulting from such dosage regimes may affect the pharmacological and therapeutic effect, thereby resulting in beneficial or detrimental consequences for certain drug therapies. In some instances, the fall off of the plasma concentration of the active ingredient between peaks results in a wash-out period and may contribute to a reduction in or prevention of patient tolerance to various types of drugs. Pulsatile release formats have proven successful for a range of drugs but many others have not benefited from such delivery systems and it has not been particularly successful for colon-specific or the development of true once-daily forms of certain drug classes, including low solubility small molecules and biopharmaceuticals.

Alternatively, other drugs may not be absorbed in the small intestine but may exhibit greater absorption levels in the colon. The invention provides drug delivery technologies to enhance absorption of hydrophilic, hydrophobic or lipophilic drugs from the colon. By-passing the gastric and small intestinal regions, and releasing drugs intact and in soluble as well as permeabilised form directly into the colon enhances absorption of the drug from the colon.

Examples of drugs that have demonstrated limited colonic absorption include Tacrolimus, Cyclosporine, Carvedilol, Budesonide and Celecoxib.

Tacrolimus, a macrolide agent is an immunosuppressant and is primarily used in post-organ transplant patients to prevent organ rejection. Tacrolimus is differentially absorbed from in different regions of the gastrointestinal tract, being optimally absorbed from the small intestine, with ileum and colonic absorption efficiency dropping to half that observed for the small intestine. Also, a food effect is observed. After absorption from the gastrointestinal tract, drug effects persist for 8-12 hours after oral administration of conventional IR tablets. The total dosage is typically in the range of 2.5-10 mg per day, in exceptional cases rising to 20 mg/day. Under conventional dosage regimes, Tacrolimus is given twice daily, typically with one dose given before breakfast and a second dose given in the late afternoon. Adverse effects, due to the initial rapid absorption from the small intestine results in above therapeutic plasma concentrations, associated with tacrolimus treatment include nephrotoxicity and the development of patient infection due to immunosuppression. There is a need for a controlled release format that prevents toxic side effects while enhancing absorption from the ileum and colon.

Cyclosporine is a cyclic polypeptide immunosuppressant agent. Formulated as an emulsion, it is indicated for the prevention of organ rejection in kidney, liver and heart transplants, for the treatment of severe active rheumatoid arthritis (RA) and severe recalcitrant plaque psoriasis. Other potential indications include Bechet's disease, anaemia, nephrotic syndrome and Graft Versus Host Disease (GVHD), including Gastro-Intestinal Graft Versus Host Disease (GI-GVHD). Significant nephrotoxicity and hepatotoxicity is a serious, dose-related side effect associated with long term use of cyclosporine. This is most likely due to the bolus-like release from the only available administration format, the large soft-gel capsule. In a study by Sandborn et al. the relative systemic absorption of cyclosporine following oral and intravenous as well as oil- and a water-based enemas was determined. Based on negligible plasma cyclosporine concentrations following enema administration, it was suggested that cyclosporine, even when solubilised, is poorly absorbed from the colon. Despite the lack of colonic absorption the enemas demonstrated considerable efficacy in the treatment of inflammatory bowel disease. Interestingly, orally administered cyclosporine demonstrated very limited efficacy in the treatment of inflammatory bowel disease. This is most likely due to the fact that the cyclosporine was systemically absorbed from the small intestine or degraded in the intestine with little or no intact cyclosporine reaching the colon to treat what is considered by some to be a cell mediated immune dysfunction at the level of the intestinal mucosa. Thus, based on the associated side effects, there exists a need for a controlled release formulation to prevent dose-related side effects and also a need for an orally delivered, colon-specific released product for the treatment of colon associated inflammatory bowel disease without any associated dose related side-effects.

Additionally, for conditions that may affect the entire gastro-intestinal tract, including the small intestine, such as Crohn's Disease and GI-GVHD, a sustained release format of pre-solubilised Cyclosporine, exhibiting limited systemic absorption is desirable.

Furthermore, in addition to cyclosporine and tacrolimus, other immunosuppressant, including, but not limited to sirolimus may be would benefit from an improved controlled or targeted release drug delivery technology. All immunosuppressant agents, including but not limited to tacrolimus, cyclosporine and sirolimus, have the potential to benefit from the development of a pre-solubilised, colon-specific drug delivery format in the context of inflammatory bowel diseases, including Crohn's Disease, Ulcerative Colitis and GI-Graft-Versus-Host Disease.

Carvedilol is an antioxidant and non-selective alpha- and beta-blocker used in the management of essential hypertension, alone or in combination with other antihypertensive agents, and for the treatment of mild-to-severe heart failure of ischemic or cardiomyopathic origin. Other approved indications, include the reduction of cardiovascular mortality in clinically stable patients who have survived the acute phase of a myocardial infarction and a left ventricular ejection fraction of less than or equal to 40%. Carvedilol is poorly water soluble with highest solubility at pH 5.0, is absorbed rapidly from the small intestine, reaching maximum plasma concentration within two hours and has a half-life of 7-10 hours. It undergoes extensive first-pass metabolism resulting in an absolute bioavailability of approximately 25%. While a food effect is suggested, the pharmacokinetics for the marketed product, Coreg™, is linearly related to dose. It has been demonstrated that absorption decreases within the intestine with relative absorption in the jejunum, ileum and colon of approximately 56%, 28% and 7% respectively. As a BSC Class II product, its absorption is considered solubility limited, rather than permeability limited. Thus, a controlled release format to target initial release into the jejunum followed by release of the active in soluble form into the colon is desirable for the development of a true once-daily carvedilol formulation.

Budesonide is a poorly-soluble, synthetic steroid of the glucocorticoid family. The naturally-occurring hormone whose actions budesonide mimics, is cortisol or hydrocortisone which is produced by the adrenal glands. Glucocorticoid steroids have potent anti-inflammatory actions. Reformulated as Entocort EC, budesonide is released from granules in the ileum of the small intestine and the right (proximal) colon, where the inflammation of Crohn's disease occurs. Budesonide acts directly by contact with the ileum and colon. The budesonide that is absorbed into the body travels to the liver where it is broken-down and eliminated from the body. This prevents the majority of the absorbed drug from being distributed to the rest of the body. As a result, budesonide causes fewer severe side effects throughout the body than other corticosteroids. The effectiveness of budesonide in the treatment of Crohn's and broader Inflammatory Bowel Diseases could be enhanced if developed as a pre-solubilised, ileum- or colon-specific drug delivery format.

Celecoxib is an oral COX-2 inhibitor, developed and indicated for treating the signs and symptoms of adult rheumatoid arthritis (RA), osteoarthritis (OA) and ankylosing spondylitis (AS); for managing acute pain in adults; for treating primary dysmenorrhea; and for reducing the number of colorectal polyps in familial adenomatous polyposis (FAP) and as an adjunct to related care, including surgery, with potential applications in post-traumatic pain and tooth extraction pain. In April 2005, following the withdrawal of Vioxx, an FDA panel concluded that Celebrex carried a 'moderate' cardiovascular risk. A poorly soluble drug, celecoxib is administered in capsule format. To focus on the FAP indication, colon specific delivery would be advantageous as a targeted delivery system and to reduce any potential side effect risks.

As the above cited drug examples have proven difficult to formulate, true once-daily formats have proven difficult to develop. To overcome this issue, enhanced delivery systems with the potential to combine aspects of any of solubility, permeability and stability enhancement along with gastrointestinal targeted release are required.

The invention is particularly applicable to chronotherapeutics. Based on the body's natural circadian rhythms, certain disease conditions lessen or worsen depending on the time of day or night. Scientific and medical research has proven that many physiological biochemical pathways follow the natural circadian body rhythms. As a consequence, cardiovascular conditions such as angina pectoris and myocardial infarction are more common in the early hours of the morning while the sympathetic nervous system relaxes during the night hours, thereby lessening the need for therapeutics that affect this system, such as beta blockers (Lemmer, Chronopharmacology, Marcel Decker, 1989; Lemmer, Pharmacol. Ther., 111:629, 2006) Likewise, allergies and asthma attacks are more common during the night-time hours (Reinberg et al, Eur J Clin Pharmacol 14:245, 1978). Furthermore, absorption from and perfusion of the small intestine varies according to the time of day or night while the motility of the gastrointestinal tract and gastric emptying vary from day to night (Lemmer et al., Chronobiol Int 8:485, 1991; Lemmer and Nold, Br J Clin Pharmacol 32:627, 1991, Goo et al., Gastroenterology 93:515, 1987)

The invention enables successful colonic delivery. In the invention a drug is protected from absorption and/or the environment of the upper gastrointestinal tract (GIT) but allows abrupt and/or sustained release into the proximal colon, which is the optimum site for colon-targeted delivery of drugs. Such colon targeting is particularly of value for the treatment of diseases of colon such as Crohn's diseases, ulcerative colitis, colorectal cancer and amebiasis. Small molecules, peptides, proteins, antibodies, including antibody fragments, oligonucleotides, including siRNAs and vaccines pose potential candidature for colon targeted drug delivery.

In various embodiments comprising a membrane-controlled dosage form, the polymeric material comprises methacrylic acid co-polymers, ammonio methacrylate co-polymers, or mixtures thereof. Methacrylic acid co-polymers such as EUDRAGIT™ S and EUDRAGIT™ L (Evonik) are suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit a solubility at a pH between the pHs at which EUDRAGIT™ L and EUDRAGIT™ S are separately soluble.

The membrane coating can comprise a polymeric material comprising a major proportion (i.e., greater than 50% of the total polymeric content) of at least one pharmaceutically acceptable water-soluble polymers, and optionally a minor proportion (i.e., less than 50% of the total polymeric content) of at least one pharmaceutically acceptable water insoluble polymers. Alternatively, the membrane coating can comprise a polymeric material comprising a major proportion (i.e., greater than 50% of the total polymeric content) of at least one pharmaceutically acceptable water insoluble polymers, and optionally a minor proportion (i.e., less than 50% of the total polymeric content) of at least one pharmaceutically acceptable water-soluble polymer.

Ammonio methacrylate co-polymers such as EUDRAGIT™ RS and EUDRAGIT™ RL (Evonik) are suitable for use in the modified release formulations of the present invention. These polymers are insoluble in pure water, dilute acids, buffer solutions, or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMC1) groups in the polymer. Those polymers having EA:MMA:TAMC1 ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The amino methacrylate co-polymers can be combined in any desired ratio, and the ratio can be modified to modify the rate of drug release. For example, a ratio of EUDRAGIT™ RS:EUDRAGIT™ RL of 90:10 can be used. Alternatively, the ratio of EUDRAGIT™ RS:EUDRAGIT™ RL can be about 100:0 to about 80:20, or about 100:0 to about 90:10, or any ratio in between. In such formulations, the less permeable polymer EUDRAGIT™ RS would generally comprise the majority of the polymeric material with the more soluble RL, when it dissolves, permitting creating gaps through which solutes can enter the core and dissolved pharmaceutical actives escape in a controlled manner.

The amino methacrylate co-polymers can be combined with the methacrylic acid co-polymers within the polymeric material in order to achieve the desired delay in the release of the drug. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the core.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. In a study by Gupta et al (*Int J Pharm,* 213: 83-91, 2001) Eudragit FS 30 D demonstrated its potential for colonic delivery by resisting drug release up to pH 6.5 and the combination of Eudragit™ RL and RS proved successful for the sustained delivery of 5-ASA at the pH of the colon. Thus, Eudragit™ FS 30 D alone or with other controlled release polymers holds great potential to enable delivery of minicapsule formulations specifically to the colon.

In addition to the EUDRAGIT™ polymers described above, a number of other such copolymers can be used to control drug release. These include methacrylate ester co-polymers such as the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114.

Several derivatives of hydroxypropyl methylcellulose (HPMC) also exhibit pH dependent solubility. Shin-Etsu Chemical Co., Ltd. esterified HPMC with phthalic anhydride to produce hydroxypropyl methylcellulose phthalate (HPMCP), which rapidly dissolves in the upper intestinal tract. Due to the limited compatibility of HPMCP with several types of plasticizers, hydroxypropyl methylcellulose acetate succinate (HPMCAS) was developed. The presence of ionizable carboxyl groups in the HPMCAS structure cause the polymer to solubilize at high pH (>5.5 for the LF grade and >6.8 for the HF grade). This polymer exhibits good compatibility with a variety of plasticizing agents and is commercially available from Shin-Etsu Chemical Co. Ltd. under the proprietary name AQOAT® in a powdered form to be redispersed in water.

Surelease® dispersion is a unique combination of film-forming polymer, plasticizer and stabilizers. Designed for sustained release and taste masking applications, Surelease is an easy-to-use, totally aqueous coating system using ethylcellulose as the release rate controlling polymer. The dispersion provides the flexibility to adjust drug release rates with reproducible profiles that are relatively insensitive to pH. The principal means of drug release is by diffusion through the Surelease dispersion membrane and is directly controlled by film thickness. Increasing or decreasing the quantity of Surelease® applied can easily modify the rate of release. With Surelease dispersion, reproducible drug release profiles are consistent right through from development to scale-up and production processes.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating membrane can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer. The coating process can be carried out by any suitable means, for example, by using a perforated pan system such as the GLATT, ACCELACOTA, Vector, Diosna, O'Hara, HICOATER or other such coating process equipment.

Seamless minicapsules may be manufactured using the method described in U.S. Pat. No. 5,882,680 (Freund), the entire contents of which are incorporated herein by reference.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566.

A number of modified dosage forms suitable for use are described below. A more detailed discussion of such forms can also be found in, for example The Handbook of Pharmaceutical Controlled Release Technology, D. L. Wise (ed.), Marcel Decker, Inc., New York (2000); and also in Treatise on Controlled Drug Delivery: Fundamentals, Optimization, and Applications, A. Kydonieus (ed.), Marcel Decker, Inc., New York, (1992), the relevant contents of each of which are hereby incorporated by reference for this purpose. Examples of modified-release formulations include but are not limited to, membrane-modified, matrix, osmotic, and ion-exchange systems. All of these can be in the form of single-unit or multi-unit dosage forms, as alluded to above.

With membrane-modified extended-release dosage forms, a semi-permeable membrane can surround the formulation containing the active substance of interest. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane, which may be determined by, e.g., the composition of the membrane, will determine the nature of release from the dosage form.

In particular, the present invention provides for formulations of minicapsules or minispheres wherein the modified release is dependent upon, where appropriate, any one of the core formulation constituents, the shell composition or the shell coating. The minicapsules or minispheres may be produced through the utilisation of surface tension of one or more different solutions which when ejected through an orifice or nozzle with a certain diameter and subject to specific frequencies and gravitational flow, forms into a spherical form and falls into a cooling air flow or into a cooling or hardening solution and the outer shell solution where it is gelled or solidified. This briefly describes the formation of seamless minispheres. According to prior art the core solution is mainly a hydrophobic solution or suspension. The outer shell solution can be any gel forming agent but is normally gelatine- or alginate-based based but may also include polymers or other materials that enable controlled release. However a hydrophilic solution can also be encapsulated with the existence of an intermediate solution, which can avoid the direct contact of the hydrophilic core solution with the outer shell. With the nozzle having a single orifice, a minicapsule or a bead of shell/core mixed suspension can be processed and may further be processed using a melt extruder. With the nozzle having two orifices (centre and outer), a hydrophobic solution can be encapsulated. Where appropriate, it may be possible that both the core and/or shell may be comprised of a material or material composites that have been processed by a wet- or dry-extrusion mechanism, melt or otherwise fluidized prior to mixing or extrusion. Ideally, to enable drug content and release consistency, it is preferred that all processes will result in fairly uniform morphologies with a relatively smooth surface to facilitate quite even coating layers to be added in a uniform manner. With the nozzle having one or more orifices seamless minicapsules for various applications can be processed using minicapsule processing equipment enabled by, but not limited to, Freund Spherex, ITAS/Lambo Globex or Inotech processing equipment. As outlined above the coating process can be carried out by any suitable means, for example, by using a perforated pan or fluidized-based system such as the GLATT, Vector, ACCELACOTA, Diosna, O'Hara and/or HICOATER processing equipment.

The result is modified release compositions that in operation deliver one or more active ingredients in a unique, bimodal or multimodal manner. The present invention further relates to solid oral dosage forms, sachets or suppositories containing such multiple minicapsule or minisphere controlled release compositions as well as methods for delivering one or more active ingredients to a patient in a bimodal or multimodal manner. Furthermore, the invention permits targeted release of orally delivered formulations to specific regions of the gastrointestinal tract to maximize absorption, confer protection on the payload, to optimize treatment of diseased intestinal tissue or enhance oral bioavailability. Additionally, the invention enables one or more pharmaceutical active to be administered sequentially or concomitantly to improve disease treatment and management and to benefit from the body's natural circadian rhythms. The invention also permits the release of pharmaceutical actives into the ileum and colon for the enhanced treatment of local intestinal diseases or to facilitate the absorption of active pharmaceutical agents, including biopharmaceuticals such as peptide and proteins.

The invention enables a pharmaceutical agent, small molecule or macromolecule, to be clinically effective, to reach its intended target in an active form, either as the native compound or an active metabolite of the compound. The use of enteric polymer coatings protects the contents of minicapsules from gastric acid degradation while other colon-specific coatings permit release of minicapsule contents only in the colon where the proteolytic enzyme content is significantly less than in the small intestine. Thus, by controlling the minicapsule coatings the invention provides formulations that ensure that the active contents are released intact at sites where absorption or therapeutic activity is optimal.

In the invention, for drugs where systemic bioavailability is critical, that transport of the active agent from the intestinal or colonic lumen to the blood or lymphatic system is maximized. As the physicochemical properties of drugs vary widely absorption of different drug classes, from hydrophilic, hydrophobic to lipophilic, are absorbed to varying extents as they pass along the gastrointestinal tract from stomach to colon. In general, the more lipophilic agents are more readily absorbed from the entire intestine than are hydrophilic agents. Where lipophilic agents exhibit poor permeability they are often formulated as micro- or other emulsions that permit interaction with bile salts which enhances absorption in the small intestine. To enhance hydrophilic intestinal permeability various approaches have been adopted, including the development of lipid-based conjugates which confer upon the active agent a more lipid-like nature which permits enhanced small intestinal permeability and hence systemic bioavailability. The potential applications include, but are not limited to, anticancer agents to target metastatic cancerous cells in the lymphatic system, vaccines, immunomodulators, including immunostimulators, agents that undergo extensive first-pass effects in the liver, as well as to enhance the relative half-live of active pharmaceuticals in patients with short bowels and where absorption is limited to the intact small intestine. Where the absorption of small molecules with limited half-lives that are systemically absorbed only through the small intestine is required, the development of controlled release floating systems, whereby the system, in this instance controlled-release multiple minicapsules, is buoyant in the gastric environment may be enabled by this invention.

The invention relates to drug delivery in the colon which has been largely overlooked from a drug delivery perspective. Mainly having evolved to regulate electrolyte balance and to further breakdown complex carbohydrate structures there is a significant flow of water from the colonic lumen into the body. In addition, the colon is home to a natural bacterial flora to degrade complex carbohydrates to ensure effective excretion, provide much needed fibre and some nutrient absorption. With a much lower concentration of proteolytic and other enzymes populated in the colon, it is a much more benign environment for proteins and peptides as well as other biological entities such as carbohydrates and nucleic acids. From a drug delivery perspective, the colon presents a number of interesting possibilities: the bacteria can be harnessed to break down controlled release coatings that are resistant to acidic breakdown as well as pH differentials; the benign environment ensure than active pharmaceuticals, including biopharmaceuticals, are less likely to be degraded if released locally into the colon; the almost continuous flow of fluids from the colonic lumen to the bloodstream may be harnessed to carry hydrophilic entities from the intestine to the lumen. Finally, the long transit time in the colon, ranging form 10-20 hours provides greater residence and potential for interaction with the colonic mucus and epithelial cells leading to enhanced absorption.

Technologically, this invention is based on various modifications of basic one- or multi-layered minicapsules, modulating the core, the shell or the coating to permit enhanced solubility and permeability of the drug or other active or non-active entity as well as conferring protection on drugs or entities that are susceptible to various forms of intestinal, mucosal or systemic degradation and targeted release of the therapeutically-active or -inactive entities to predetermined regions of the gastrointestinal tract.

In addition to the above minicapsule modifications, the present invention provides the coating of minicapsules or minispheres with a muco- or bio-adhesive entity which will ensure that they first adhere to the mucosa prior to releasing the fragile payload. The advantages thus enabled include further protection of the active entities but also release of the actives proximal to the site of absorption. As absorption is, in part, related to the surface area exposed to the active as well as the concentration gradient from intestinal luminal side to the intestinal basal side, the higher local yet dispersed concentration has greater potential to ensure enhanced absorption, not only of hydrophilic drugs, but also lipophilic or hydrophobic drugs.

A barrier to effective colonic delivery of hydrophobic and lipophilic drugs is that the colon did not evolve to solubilize foodstuffs and other entities but rather to ensure electrolyte balance and maximize fibre breakdown and fermentation. The colon remains very porous to hydrophilic entities. By delivering hydrophobic or lipophilic drugs to the colon in a pre-solubilised or readily soluble format and releasing such in the colon, the potential for absorption is enhanced significantly. The present invention permits the encapsulation of pre-solubilized or readily soluble drugs in liquid or hydrolysable semi-solids or solids into the minicapsule core and then modulation of the shell to include intestinal- or colon-controlled release polymers or coating the shell with same. The result is release of optimized formulations at specific sites along the intestinal tract for maximal therapeutic efficacy or systemic absorption.

Likewise, delivery of formulations that are readily broken down in an aqueous environment or a bacteria rich environment has the potential, when coated with colon-specific controlled release polymers or include entities that are degraded by bacteria have the potential to protect susceptible entities from the gastric or intestinal environment yet ensure that they are released intact in the colon where, once liberated, will be readily absorbed. Redox-sensitive, pectin-, alginate-, chitosan- or other bacterially susceptible polymer-based matrices, coatings or other sustained release formulations, liquid, semi-solid or solid, can be encapsulated into or coated onto one- or multi-layered minicapsules.

The formulations of the present invention can exist as multi-unit or single-unit formulations. The term "multi-unit" as used herein means a plurality of discrete or aggregated minicapsules, minispheres, particles, beads, pellets, granules, tablets, or mixtures thereof, for example, without regard to their size, shape, or morphology. Single-unit formulations include, for example, tablets, hard gelatin capsules, caplets, and pills.

The methods and formulations of the present invention are intended to encompass all possible combinations of components that exhibit modified-release and immediate-release properties. For example, a formulation and/or method of the invention can contain components that exhibit extended-release and immediate-release properties, or both delayed-release and immediate-release properties, or both extended-release and delayed-release properties, or a combination of all three properties. For example, a multi-minicapsule or multi-minisphere formulation including both immediate-release and extended-release components can be combined in a capsule, which is then coated with an enteric coat to provide a delayed-release effect. Or, for example, a delayed- and extended-release caplet may comprise a plurality of discrete extended-release particles held together with a binder in the caplet, which is coated with an enteric coating to create a delay in dissolution.

As used herein, the term "modified-release" formulation or dosage form includes pharmaceutical preparations that achieve a desired release of the drug from the formulation. A modified-release formulation can be designed to modify the manner in which the active ingredient is exposed to the desired target. For example, a modified-release formulation can be designed to focus the delivery of the active agent entirely in the distal large intestine, beginning at the cecum, and continuing through the ascending, transverse, and descending colon, and ending in the sigmoid colon. Alternatively, for example, a modified-release composition can be designed to focus the delivery of the drug in the proximal small intestine, beginning at the duodenum and ending at the ileum. In still other examples, the modified-release formulations can be designed to begin releasing active agent in the jejunum and end their release in the transverse colon. The possibilities and combinations are numerous, and are clearly not limited to these examples.

The term "modified-release" encompasses "extended-release" and "delayed-release" formulations, as well as formulations having both extended-release and delayed-release characteristics. An "extended-release" formulation can extend the period over which drug is released or targeted to the desired site. A "delayed-release" formulation can be designed to delay the release of the pharmaceutically active compound for a specified period. Such formulations are referred to herein as "delayed-release" or "delayed-onset" formulations or dosage forms. Modified-release formulations of the present invention include those that exhibit both a delayed- and extended-release, for example, formulations that only begin releasing after a fixed period of time or after a physicochemical change has occurred, for example, then continue releasing over an extended period.

As used herein, the term "immediate-release formulation," is meant to describe those formulations in which more than about 50% of active ingredient is released from the dosage form in less than about 2 hours. Such formulations are also referred to herein as "conventional formulations."

As used herein, the phrase "drug-release profile that is independent of surrounding pH" means effectively a drug composition comprising a polymeric system that is non-enteric or whose permeability and solubility properties do not change with environmental, i.e., external, pH. Meaning, a drug composition having release characteristics such as dissolution is substantially unaffected by pH or regardless of pH-changes in the environment. This is in comparison to a release profile that is pH-dependent where the release characteristics vary according to the pH of the environment.

Applications

Colonic Delivery—In addition to oral delivery of small molecules and macromolecules, including proteins, peptides, antibodies and any fragment or otherwise modified constructs thereof, the present invention also has the potential to enable the development of optimized colonic delivery of various health promoting live or attenuated organisms, including vaccines, probiotic bacteria, or genetically modified bacteria, modified to express and secrete therapeutic entities such as various interleukins.

As the colon is rich in lymphoid tissue, uptake of antigens into the mast cells of the colonic mucosa produces rapid local production of antibodies and this may be exploited through use of modified minicapsules to develop efficient oral vaccine delivery systems. This will involve the encapsulation of antigens and adjuvants in a suitable oil, emulsion, particulate suspension or other format within minicapsule with modified shells or shell coatings that include colon-specific polymers and/or muco- or bio-adhesive molecules. Additionally, colon-specific lymphatic tissue targeted delivery of immunotherapeutics, including immunostimulators and immunosuppressants, is attractive as the lymphatic system acts as a reservoir or warehouse for the immune system.

Also, exploiting the lymphoid-rich colonic tissue, the present invention will utilize lipid-based formulations that are readily absorbed into the lymphatic vasculature and channelled toward the blood vasculature provides a potential means to enhance delivery of highly lipophilic drugs or other entities, including hydrophobic peptides, proteins or other biopharmaceutical agents, including antibodies or any fragment thereof.

It is known that certain medium and long-chain fatty acids exert an intestinal epithelial effect which leads to an increased permeability of intestinal membranes to entities that may otherwise be impermeable or exhibit limited permeability. The medium chain triglycerides, including but not limited to sodium caprate, enhance absorption to a greater extent in the small intestine than in the ileum or colon (results attached). In a study to investigate the effects of the long-chain polyunsaturated fatty acids, mainly eicosapentaenoic acid (EPA) and docosahexaenoic acid (DHA) on insulin absorption from rat intestinal loops in situ, Suzuki et al demonstrated that both EPA and DHA strongly enhanced insulin absorption and induced hypoglycemia after rectal and colonic dosing. DHA did not induce gross morphological changes in the structure of the intestinal mucosa (Suzuki et al, Journal of Pharmaceutical Sciences, Vol 87, 10: Pgs. 1196-1202); 1998). Thus, it is apparent that medium chain triglycerides enhance intestinal permeability while DHA is a possible means of facilitating the intestinal absorption of insulin and possibly other macromolecules, peptides and proteins included, without inducing any serious damage to epithelial cells. Combining poorly permeable entities with medium- or long-chain fatty acids and targeted delivery to local regions of the intestine or colon has the potential to enhance absorption of otherwise poorly permeable entities. The current invention seeks to enable such delivery through the encapsulation of entities formulated with polyunsaturated fatty acids using a gelling agent, including, but not limited to one or a mixture of gelatine, pectin, alginate or chitosan, with or without an additional colon-specific coating.

Thus, while the primary advantage of the current invention relates to enhanced colon delivery for absorption from the colon or treatment of diseased intestinal and colonic tissue, the invention also permits the development of sustained absorption of hydrophobic and lipophilic drugs that otherwise would not be soluble in the colon. By extension, the invention also facilitates the development of novel combination therapies as well as inventive chronotherapies comprising one or a multiple of drugs released at different time points.

Targeted Release/Enhanced Sustained Absorption/Reduced Side Effects

As known to those practiced in the Art, carvedilol is poorly water soluble with highest solubility at pH 5.0, is absorbed rapidly from the small intestine, reaching maximum plasma concentration within two hours and has a half-life of 7-10 hours. It undergoes extensive first-pass metabolism resulting in an absolute bioavailability of approximately 25%. While a food effect is suggested, the pharmacokinetics for the marketed product, Coreg™, is linearly related to dose. It has been demonstrated that absorption decreases within the intestine with relative absorption in the jejunum, ileum and colon of approximately 56%, 28% and 7% respectively. As a BSC Class II product, its absorption is considered solubility limited, rather than permeability limited. Thus, a controlled release format to target initial release into the jejunum followed by release of a solubilised form of the active into the colon is desirable for the development of a true once-daily carvedilol formulation. In the current invention, a once-daily product will be developed. This will be achieved through the development of a sequential pulsatile release minicapsule format, the core of such minicapsules will contain carvedilol in pre-solubilised form and coated with controlled release polymers to ensure release two- or three-times within a 24 hour period, for example immediate release for intestinal absorption and 12 hour-delayed release for colonic absorption. Alternatively, the immediate release component could be formulated as solid minisphere form.

Similarly, Tacrolimus and Sirolimus are differentially absorbed from in different regions of the gastrointestinal tract, being optimally absorbed from the small intestine, with ileum and colonic absorption efficiency dropping to half that observed for the small intestine. Also, a food effect is observed. After absorption from the gastrointestinal tract, drug effects persist for 8-12 hours after oral administration of conventional IR tablets. The total dosage is typically in the range of 2.5-10 mg per day, in exceptional cases rising to 20 mg/day. Under conventional dosage regimes, Tacrolimus is given twice daily, typically with one dose given before breakfast and a second dose given in the late afternoon. Adverse effects, due to the initial rapid absorption from the small intestine results in above therapeutic plasma concentrations, associated with tacrolimus treatment include nephrotoxicity and the development of patient infection due to immunosuppression. There is a need for a controlled release format that prevents toxic side effects while enhancing absorption from the ileum and colon. Formulating Tacrolimus in a minicapsule format, the core of which is pre-solubilised, has the potential to enhance the absorption of Tacrolimus from the colon. Also, through development of a sustained release format, either through modifying the core formulation to enable sustained release or coating the surface with a sustained release polymer will reduce the peak plasma drug concentration, thereby reducing the potential dose-related side effects, including nephrotoxicity and excessive immunosuppression.

Intestinal Diseases

Gastrointestinal conditions pose a significant worldwide health problem. Inflammatory bowel diseases, which genus encompass a range of diseases including Crohn's disease and ulcerative colitis, affect nearly 1 million people in the United States each year. The two most common inflammatory conditions of the intestine, ulcerative colitis (UC) and Crohn's disease (CD), are collectively known as inflammatory bowel disease (IBD). These conditions are diseases of the distal gut (lower small intestine, large intestine, and rectum) rather than the proximal gut (stomach and upper small intestine). Between the two, ulcerative colitis primarily affects the colon, whereas Crohn's disease affects the distal small intestine as well.

Inflammatory Bowel Disease (IBD)

Although they are distinct IBD conditions, the same drugs are commonly used to treat both UC and CD. Drugs commonly used in their treatment include steroids (e.g., budesonide and other corticosteroids, and adrenal steroids such as prednisone and hydrocortisone); cytokines such as interleukin-10; antibiotics; immunomodulating agents such as azathioprine, 6-mercaptopurine, methotrexate, cyclosporine, and anti-tumor necrosis factor (TNF) agents such as soluble TNF receptor and antibodies raised to TNF; and also antinflammatory agents such as zinc. The most commonly prescribed agents for IBD include sulfasalazine (salicyl-azosulfapyridine, or "SASP") and related 5-aminosalicylic acid ("5-ASA") products, including mesalazine.

Inflammation of the ileum (the farthest segment of the small intestine) due to Crohn's disease is known as iletis. When both the small intestine and the large intestine are involved, the condition is called Crohn's enterocolitis (or ileocolitis). Other descriptive terms may be used as well. Diagnosis is commonly made by x-ray or colonoscopy. Treatment includes medications that are anti-inflammatories, immune suppressors, or antibiotics. Surgery can be necessary in severe cases. Crohn's disease is an area of active research around the world and new treatment approaches are being investigated which have promise to improve the lives of affected patients.

Gastrointestinal Graft-Versus-Host-Disease (GI-GVHD)

GI GVHD is a life-threatening condition and one of the most common causes for bone marrow and stem cell transplant failure. These procedures are being increasingly used to treat patients with leukemia and other cancers to eliminate residual disease and reduce the likelihood of relapse. Unlike solid organ transplants where the patient's body may reject the organ, in GVHD it is the donor cells that begin to attack the patient's body—most frequently the gut, liver and skin. Patients with mild-to-moderate GI GVHD typically develop symptoms of anorexia, nausea, vomiting and diarrhea. If left untreated, GI GVHD can progress to ulcerations in the lining of the GI tract, and in its most severe form, can be fatal. Systemic immunosuppressive agents such as prednisone, which are the current standard treatments for GI GVHD, are associated with high mortality rates due to infection and debility. Further, these drugs have not been approved for treating GI GVHD in the U.S. or European Union, but rather are used off-label as investigational therapies for this indication.

Minicapsule-enabled colon-targeted immunosuppressant therapy delivering agents such as cyclosporine A to the colon is a novel oral, locally acting active therapy which will reduce the need for systemic immunosuppressive drugs such as prednisone, which is currently used to prevent and control GI GVHD. Drugs such as prednisone have the unwanted and potentially dangerous side effects of weakening the patient's immune system leaving them susceptible to opportunistic infections as well as substantially inhibiting the intended anti-cancer effect of bone marrow and stem cell transplants. Minicapsule-enabled colon-targeted immunosuppressant therapy is designed to reduce the need for systemic immunosuppressive drugs and thereby improve the outcome of bone marrow and stem cell transplantation. Therefore, it is possible that delivery of intact peptides or proteins to the colon may be achieved.

Cyclosporine, Tacrolimus and Sirolimus are recognized, on- and off-label, as common treatments for IBD and is widely used for this purpose. However, cyclosporine, tacrolimus and sirolimus therapy continue to exhibit problems, including side effects to be detailed hereinafter. Additionally, both exhibit a half-life and efficacy profile that is less than maximal, reflected in high and multiple daily doses, lower response and remission rates, and higher relapse rates, related to its site and mechanism of action and efficiency of delivery to the cells of the distal gut. Extensive Cyclosporine and Tacrolimus absorption from the small intestine reduces its availability at distal sites in the gut, which are the sites of the therapeutic effect and the preferred sites of delivery, thereby necessitating high doses to be administered. Ideally, the compound should reach the distal gut (ileum and/or colon) in unchanged form, but not be absorbed into the systemic circulation as the parent compound from there. The absorption into the systemic circulation from proximal and/or distal sites as the parent compound results in side effects associated with the absorbed drug and its systemic effects. Existing oral dosage forms of cyclosporine and tacrolimus, namely soft or hard gelatine capsules, are unsuited to controlled or ileum/colon targeted release.

To overcome systemic side effects and the need to administer high doses frequently, the current invention proposes first formulating either Cyclosporine or Tacrolimus as solubilised formulations, encapsulating with a gelling agent to produce minicapsules. The encapsulating agent may contain controlled release polymers that release only in the ileum or colon or may be coated with a polymer or other coating that results in same. The advantages are several-fold, including: reduced systemic absorption of the active cyclosporine or tacrolimus which is known to result in dose related toxicities, including nephrotoxicity, release of sufficient dose of cyclosporine or tacrolimus in soluble form as well as a broad distribution of cyclosporine or tacrolimus throughout the colon. Furthermore, incorporating a mucoadhesive into the encapsulating shell or coating the encapsulating shell with a mucoadhesive may ensure that the minicapsules are in contact with the colonic mucus layer prior to releasing the active proximal to the diseased tissue.

For certain Crohn's Disease sub-groups it may be required to enable release throughout the gastrointestinal tract, including the small intestine. Likewise for GI-GVHD, it may be beneficial to have sustained release throughout the entire gastrointestinal tract from small intestine to colon.

Propyl and asparaginyl hydroxylase inhibitors are key oxygen-sensing enzymes that confer hypoxia sensitivity to key transcriptional regulatory pathways, including HIF-1 and NFκB. Knockout of either HIF or (IKκB-dependent) NFκB pathways in intestinal epithelial cells promotes inflammatory disease in murine models of colitis. Both HIF1 and NFκB pathways are repressed by the action of hydroxylases through the hydroxylation of key regulatory molecules.

Cummins et al. (Cummins et al. Gastroenterology 2008) demonstrated that dimethyloxalglycine (DMOG) induces both HIF1 and NFκB activity in cultured intestinal epithelial cells and is profoundly protective in dextran-sodium sulphate-induced colitis in a manner that is at least in part reflected by the development of an anti-apoptotic phenotype, which may reduce epithelial dysfunction.

A downside of propyl- and asparaginyl hydroxylase inhibitors is potential pro-angiogenic and anti-apoptotic activity, which systemically may lead to unwanted side effects. Therefore, a delivery system that would delivery propyl- and asparaginyl hydroxylase inhibitors such as, but not limited to, DMOG, hydralazine, FG-4095 and derivatives thereof, to the local diseased gastrointestinal epithelial cells in lower, possibly sub-toxic concentrations is highly desirable. Furthermore, local ileum or colonic delivery may reduce systemic absorption, thereby further reducing the risk of side effects.

The current invention enables the targeted release of propyl- and asparaginyl hydroxylase inhibitors to the disease colonic tissue and has resulted not only in demonstrated reduced colonic inflammation, but may also reduce the systemic concentration of such inhibitors leading to limited side effects. Additionally the invention allows for targeted release of Inhibitor of nuclear factor kappa B kinase beta subunit inhibitors or NFkB activators.

Other immunosuppressants could be considered, either alone or in combination with cyclosporine A or tacrolimus or derivatives thereof. This include, but are not limited to, various glucocorticosteriods; cytostatics such as methotrexate and azathioprine; antibodies such as the T-cell receptor directed anti-CD3 OKT3; the immunophilin receptor binder sirolimus; interferons; opioids; TNFα-binding proteins, including, but not limited to, infliximab, etanercept, adalimumab, cucumin and catechins; and Mycophenolate Mofetil acid acts as a non-competitive, selective and reversible inhibitor of inosine monophosphate dehydrogenase.

Additional therapeutics with potential for the treatment of inflammatory bowel disease or irritable bowel syndrome include, but are not limited to, pharmaceutical compositions comprising a dose of an NO donor, such as, but not limited to, NOC5 [3-(2-hydroxy-1-(methylethyl)-2-nitrosohydrazino)-1-propanamine], NOC12 [N-ethyl-2-ethyl-hydroxy-2-nitrosohyrdrazino-ethanamine], nitroglycerine or other therapeutics modified to include a conjugated NO donor.

Yet other pharmaceutical compositions include various calcium channel blockers, including but not limited to nimodipine, amlodipine, verapamil, including various enantiomers and salts thereof as well as NO donor conjugates thereof. Certain natural extracts, including Neem oil, aloe vera, tripala, tumeric and other essential oils, including the omega polyunsaturated oils such as EPA, DHA, conjugated linoeic acid (CLA) and other derivatives thereof, have potential as treatments to alleviate or prevent inflammatory bowel disease as well as other intestinal disorders, including gastric, duodenal and intestinal ulcers. Additionally, certain plant extracts, including berry extracts such as blueberry, achi, resorcinolic/phenolic lipids, resveratrol, flavanoids and derivatives thereof, alone or in combination, have potential application in IBD and IBS and other intestinal or systems conditions. The mode of action of berry extracts, such as blueberry extract, remains uncertain but has effect on intestinal motility, stool formation and colonic flora. Yet other potential therapeutics include, but are not limited to, proteins, therapeutic peptides, vaccines, antibodies or fragments thereof. Local delivery to the mucosa will overcome degradation and ensure that a high local concentration is available to enhance therapeutic efficacy. Encapsulating any of the above, alone or in any combination, into minicapsules or minispheres and targeting the release to areas of the intestine that are diseased provide for enhanced disease management as well as perhaps a reduction in any potential for systemic side effects.

As mentioned above, the following therapeutics: steroids (e.g., budesonide and other corticosteroids, and adrenal steroids such as prednisone and hydrocortisone, administered alone or in combination with a xanthine or methylxanthine compound); cytokines such as interleukin-10; antibiotics; immunomodulating agents such as azathioprine, 6-mercaptopurine, methotrexate, cyclosporine, and anti-tumor necrosis factor (TNF) agents such as soluble TNF receptor and antibodies raised to TNF; and also antinflammatory agents such as zinc are widely prescribed. The most commonly prescribed agents for IBD include sulfasalazine (salicyl-azo-sulfapyridine, or "SASP") and related 5-aminosalicylic acid ("5-ASA") products are commonly prescribed and due to significant side-effects of some of these as well as the above mentioned therapies would benefit from targeted colonic delivery and in some cases, pre-formulated to enhance solubility or permeability.

An alternative approach to treating intestinal or colonic disease is to deliver live organisms, including various bacteria such as probiotics, to specific regions of the intestine or colon where they exert protective or therapeutic effects. Steidler has shown that it is possible to first develop genetically modified bacteria to produce proteins and then to target the release of such proteins, including anti-inflammatory cytokines to regions of the gastrointestinal tract where they will optimally exert protective or therapeutic effects. This invention can formulated the bacteria for storage stability and target the release of such agents to the site of optimal action.

This invention is advantageous in providing methods and formulations for treating inflammatory bowel disease. The invention proposes delivering effective concentrations of pre-solubised Cyclosporine, Tacrolimus, Sirolimus, Hydralazine or DMOG to affected areas of the gastrointestinal tract, with minimized systemic absorption of parent drug. The invention is directed to, among other things, a pharmaceutical composition for administration to a subject in need thereof comprising a dose of an active pharmaceutical compound, and pharmaceutically acceptable salts, esters and pro-drugs thereof, and at least one pharmaceutically acceptable excipient, wherein the composition exhibits localized release and exhibits:

For Ulcerative Colitis and Crohn's Disease—a dissolution profile, when tested in a U.S.P. Type II apparatus (paddles) at 37.degree.C. and 50 rpm, in pH 6.8 buffer for the test: Up to 4 hours: less than or equal to about 20% drug released; 6 hours: less than or equal to about 35% drug released; 8 hours: less than or equal to about 50% drug released; 12 hours: less than or equal to about 60% drug released; 18 hours: less than or equal to about 75% drug released; and 24 hours: from about 25% to about 100% drug released.

For GI-GVHD—a dissolution profile, when tested in a U.S.P. Type II apparatus (paddles) at 37.degree.C. and 50 rpm, in pH 6.8 buffer for the test: 1 hour: less than or equal to about 20% drug released; 4 hours: less than or equal to about 35% drug released; 6 hours: less than or equal to about 50% drug released; 12 hours: less than or equal to about 60% drug released; 16 hours: less than or equal to about 75% drug released; and 24 hours: from about 25% to about 100% drug released.

This invention relates to formulations and methods for treating inflammatory bowel disease. The term "inflammatory bowel disease" includes, but is not limited to, ulcerative colitis, Crohn's disease and GI-GVHD. Other diseases contemplated for treatment or prevention by the present invention include non-ulcerative colitis, and carcinomas, polyps, and/or cysts of the colon and/or rectum. All of these diseases fall within the scope of the term "inflammatory bowel disease" as used in this specification, yet the invention does not require the inclusion of each recited member. Thus, for example, the invention may be directed to the treatment of Crohn's disease, to the exclusion of all the other members; or to ulcerative colitis, to the exclusion of all the other members; or to any single disease or condition, or combination of diseases or conditions, to the exclusion of any other single disease or condition, or combination of diseases or conditions.

Constipation Relief

Constipation manifests in a number of disease conditions or as a side-effect of certain therapies. Certain diseases, including irritable bowel syndrome, may result in significant episodes of constipation. It has been well documented that many therapeutics, including, but not limited to, opioids and antibiotics result in constipation. Opioids, including, but not limited to, morphine, morphine sulphate and the systemically active opioids naltrexone and naloxone are widely prescribed for the effective treatment of a myriad of conditions that require pain modulation. Often, the rate limiting step to effective opioid treatment is constipation. To overcome constipation, a number of approaches have been adopted, including, but not limited to osmotic agents such as polyethylene glycol, laxatives such as the naturally occurring senna and bisacodyl and 5HT receptor antagonists such as the 5HT4 antagonist zelnorm. While such adjuvant agents may be effective in treating these adverse effects, they are associated with additional adverse effects and are sometimes ineffective. As an alternative, the opioid mu receptor antagonists methylnaltrexone and alminopan have shown positive benefits in the treatment of opioid-induced constipation.

Methylnaltrexone has been in development since it was first synthesized in 1979 to offset the constipating effect of morphine, but it is not yet approved by the FDA for this use. By not crossing the blood-brain barrier, methylnaltrexone is thought to counter the constipating effects of opioids without reducing their effectiveness as pain relievers. Major questions remain about what dose is most effective and at what point, and how often, the drug should be given. Alminopan has reported efficacy in accelerating gastrointestinal recovery in patients undergoing laparotomy. It is a peripherally acting mu-opioid receptor antagonist designed to block the adverse side effects of opioid analgesics on the gastrointestinal tract without blocking their beneficial analgesic effects. A pooled analysis of 3 phase 3 efficacy trials assessed the effect on opioid analgesics after surgery. Almivopan accelerated gastrointestinal recovery while maintaining centrally mediated analgesia as measured by opioid consumption and visual analog pain scores.

The present invention will permit the controlled release of products that will overcome the constipating effects of opioids. It may be beneficial to have these products released either throughout the gastrointestinal tract or to specific locations, either to the small intestine, the ileum or the colon. The benefits may include lower dose requirements, improved efficacy as well as ease of administration and greater distribution of the product. In addition to overcoming the constipating effects of opioids, the present invention may also suit other conditions such as post-operative ileus or general constipation. Potential products include controlled release osmotic agents such as polyethylene glycol, laxatives such as the naturally occurring senna and bisacodyl, 5HT receptor antagonists such as the 5HT4 antagonist zelnorm as well as the opioid mu receptor antagonists methylnaltrexone and alminopan.

There exists an unmet need for an oral dosage form that permits once-daily delivery of opioid-based drugs, with reduced side effects. The optimal dosage form requires that the opioid-based drug is released over an 18-24 hour period, is effective over a 24 hour period and does exhibit reduced negative side effects, including constipation and pruritus.

The current invention will additionally enable the development of combination products, including combinations for the oral administration of one or more pain-relieving opioids with one or more constipation relieving agents. Specifically, the current invention proposes to develop a controlled release morphine-based product, such as morphine sulfate, that is released over 18-24 hours, in the presence or absence of a controlled release ion-channel inhibitor, such as, but not limited to nimodipine, to extend the effective analgesic period, in combination with a controlled release opioid antagonist, such as naloxone, naltrexone or methylnaltrexone, which may be released throughout the gastrointestinal tract or only in the colon and rectum.

Oral Tolerance

The intestinal mucosal immune network has evolved an ability to maintain relative unresponsiveness or tolerance to a wide array of antigens derived from dietary sources and commensal bacteria. This phenomenon is referred to as oral tolerance. Friedman et al proposed that oral tolerance is mediated by the generation of active cellular suppression or clonal anergy and that the determining factor is the dose of antigen fed orally (PNAS USA 1994; 91:6688-92). Oral tolerance is dose-specific and lose of tolerance might occur with increased dosages (Nagler-Anderson et al., PNAS USA 1986; 83:7443-6). Low dose of antigen administration favours the induction of active cellular regulation (Chen et al., 1994 Science; 265:1237-1240). Higher doses favour the induction of clonal anergy or deletion (Chen et al., 1995 Nature; 376:177-180). In another study, high doses of myelin basic protein (MBP) to mice whose T-cells carry a T-cell receptor (TCR) specific for MBP resulted in T-cell activation and receptor downmodulation (Benson et al., 2000 J Clin Invest, 106:1031-1038). Additionally, it has been shown that oral tolerance also can be enhanced by feeding immune adjuvants such as lipopolysaccharide or cholera toxin subunit B, which appear to stimulate additional populations of cells to down-regulate immune responses (Khoury et al., J Exp Med 1992; 176:1355-64).

Oral tolerance has been shown to prevent or treat a variety of T-cell mediated autoimmune disorders. In a double-blind pilot trial involving 30 patients with multiple sclerosis, oral administration of bovine myelin antigens decreased the number of T-cells that reacted with myelin basic protein, with no measurable toxicity (Werner et al., Science 1993; 259:1321-4). Trentham et al demonstrated clinical efficacy of oral tolerance by feeding type II collagen to 60 patients with severe, active rheumatoid arthritis (Trentham et al., Science 1993; 261:1727-30). In an animal model of trinitrobenzene sulfonic acid (TNBS), Th1-mediated colitis, it was reported that feeding colonic extracts haptenated with TNBS prevented the development of mucosal inflammation (Neurath et al., J Exp Med 1996; 183:2605-16). In a Phase I study to evaluate the safety and efficacy of autologous colonic protein extract feeding for the treatment of moderate-to-severe Crohn's Disease, Margalit et al. demonstrated safety and induced remission in 7 out of 10 subjects (Am J Gastroenterol 2006; 101). Other animal disease models, including stroke, Alzheimer's disease and atherosclerosis as well as type 1 diabetes have responded to mucosal administration of antigens.

To exploit oral tolerance in treating oral autoimmune or inflammatory diseases, it will be necessary to understand the various responses that are induced or suppressed during this process, beginning when antigen first encounters gut-associated lymphoid tissue (GALT), a well developed immune network consisting of lymphoid nodules (Payer's Patches), epithelial villi, intraepithelial lymphocytes, and other lymphocytes scattered throughout the lamina propria. Antigens may act directly at the level of the GALT or may exert their effects after absorption. As oral tolerance and mucosal immunization are parts of one immunologic continuum related to antigen presenting cell interactions with T cells in the GALT. Thus, the oral delivery of antigens will require fine tuning—in addition to antigen dose, the nature of the antigen, the innate immune system, the genetic background and immunological status of the host, and mucosal adjuvants will influence the immunological outcome following oral antigen administration. The development of advanced orally delivered oral tolerance and mucosal immunization prophylactics or therapies may benefit from targeted delivery to specific regions of the intestinal tract. The rectum/colon is a mix of immune inductive (organised lymphoid tissues) and effector sites (diffuse lamina propria) whereas the jejunum contains almost no immune inductive sites. This is reflected in the lymphoid composition of each tissue: the jejunum contains mostly memory $CD4^+$ T cells, while the colon contains a larger proportion of naïve $CD4^+$ T cells (Veazey and Lackner, 2006; PLoS Medicine; 3:12-2188-9). Thus, it could be hypothesised that during normal ingestion that peptides and proteins are so degraded when they reach the colon they no longer activate an immune response in naïve $CD4^+$ T cells.

The present invention will enable the development of formulations comprising the necessary antigenic, including any covalently or non-covalently modified, peptides to be formulated, with or without adjuvants or permeability enhancers, and to be encapsulate within single or multiple layer, with the layers or polymer coatings of which being modified to ensure release at the most appropriate location along the intestine or colon/rectum. The result will be an optimized, tunable and modular orally administered oral tolerance or mucosal immunization delivery technology. In addition to the above mentioned diseases that have been explored, the current invention may also benefit broader applications, such as, but not limited to, celiac disease, food allergies and more general allergies.

HIV Small Molecule Treatment and Vaccine

In acute HIV infection, a rapid and profound loss of $CD4^+$ $CCR5^+$ T cells within days of infection, whereas peripheral lymphoid tissues such as blood and lymph nodes, which harbour mainly naïve $CD4^+$ T cells, are less severely affected (Brenchley et al., 2004 J Exp Med 200:749-759). This recognition of the mucosal immune system as a principal target of early HIV infection has implications for vaccine development. Furthermore, Mehandru et al. studying lymphocyte populations from the intestine and peripheral blood were obtained from recently HIV-infected patients as well as uninfected volunteers demonstrated that most patients who initiate high activity anti-retroviral therapy (ART) as early as possible after HIV infection still do not experience complete restoration of intestinal $CD4^+$ T cells to baseline levels, regardless of the duration of therapy. Instead, HIV infection results in a continuous state of activation in the intestinal immune system that is not reflected in peripheral lymphoid tissues (Mehandru et al., 2006; PLoS Med 3(12): e484). The data from Mehandru et al. provide evidence that intestinal inflammation and continual infection, destruction, and turn-over of $CD4^+$ T cells occur in patients on ART. This would suggest that drugs with better intestinal tissue distribution, together with, perhaps, mechanisms to reduce or prevent immune activation in mucosal tissues may more effectively combat HIV infection.

The current invention will permit a number of approached to the prevention and treatment of HIV/AIDS, including controlled release of ARTs along the entire intestinal and colonic/rectal tract or to pre-specified sites along same. In addition, the current invention will permit the development of oral tolerance as well as intestinal/colonic mucosal vaccines or immunotherpeutics approaches. Furthermore, with the current invention, a combination ART/immune system modulation approach is possible.

Tight Junction Modulators

A number of small molecule and peptides are in development to regulate the functional state of tight junctions (TJ) and paracellular permeability. Molecules that transiently and reversibly open the TJs of epithelial and endothelial tissues such as the intestinal mucosa, blood brain barrier and pulmonary epithelia. As increased paracellular permeability is implicated as a causal factor in many disease states, modulation of permeability by TJ regulatory pathways represents a very important therapeutic opportunity. Potential applications range from the treatment of diseases involving tight junction dysfunction and autoimmunity to vaccine and drug delivery. Certain TJ modulators such, but not limited to, parozotide acetate, have potential in the treatment of gastrointestinal disorders, including Celiac Disease and Inflammatory Bowel Disease. The current invention will permit the local delivery of tight junction modulators and thus enhance the utility of such agents in the treatment of a range of diseases or to promote the induction of mucosal or systemic immunity to enable the development of oral vaccines or oral tolerance approaches.

Anti-Allergenic Therapeutics

It has been proposed by the so-called hygiene hypothesis that modulation of the immune system by infection with helminth parasites, including schistosomes, reduces the levels of allergic responses in infected individuals. This hypothesis proposes that a shift in the immune system toward type 1 immunity upon early exposure to infections such as bacterial and viral infections protects against allergic diseases by reducing the expression of Th2 cytokines generally evoked by allergens. An alternative explanation holds that certain parasitic helminth infections may protect against allergic disorders because human populations with high rates of parasitic helminth infections, which induce an immunological shift toward the "allergic" Th2 responses, have a reduced prevalence of allergic disorders. Schistosoma spp. are tropical helminth parasites, characteristically associated with being potent inducers of Th2 cytokine responses including eosinophilia and IgE responses, that have been postulated to ameliorate atopic disorders in humans (*The Journal of Immunology*, 2004, 173: 6346-6356).

Circumstantial evidence suggests that Schistosoma spp, tropical helminth parasites, ameliorate atopic disorders in humans. Schistosomes are characteristically associated with being potent inducers of Th2 cytokine responses, including eosinophilia and IgE responses. Despite Th2 responses being considered necessary for the development of allergies, the presence of schistosome infections in humans may reduce allergic responses in infected populations.

To confirm the hygiene hypothesis, Schistosoma hematobium-infected school children in Gabon had a lower prevalence of skin reactivity to house dust mites than those free of this infection. Therefore, it has been proposed that chronic down-regulation of the immune system during helminth infection evokes a regulatory environment that may impart protection from allergies.

Bashir et al. have demonstrated a role for experimental helminth infection in protection against the development of allergy in mice (Bashir et al. (2002) *J. Immunol.* 169:3284). They assessed the effect of Th2 responses induced by the intestinal helminth infection (*H. polygyrus*) on the development of an allergic response to the food allergen peanut Ag, with protection being mediated at least in part by the production of IL-10.

Although a novel mechanism by which a helminth parasite can prevent anaphylaxis in mice has been demonstrated, it may be too simplistic to envisage a common mechanism by which different helminth parasites may prevent allergic responses. Infection of mice with a gastrointestinal nematode (*H. polygyrus*) has been shown to reduce allergic responses in one study, whereas in a separate study mice infected with another gastrointestinal nematode (*Trichinella spiralis*) had exacerbated anaphylaxis (Strait et al., 2003, *J. Immunol.* 170:383.). Therefore, it is suggested that there are defined differences in the infectivity and immunity of these two parasites as well as in the allergy models used that could explain the differences between the studies.

Fallon's laboratory has demonstrated that *S. mansoni* infection protects mice from an experimental model of systemic fatal anaphylaxis, with the worm stage of infection being shown to mediate this protective effect. In this study it was demonstrated that mice infected with *S. mansoni* are refractory to experimental systemic anaphylaxis. It was established that it is the worm stage of infection that elicits the protective phenotype in this model, with worm-infected mice completely protected against anaphylaxis, whereas worm egg-infected mice were only partially protected. We have identified that schistosome worm infection of mice prevents anaphylaxis via a B cell- and IL-10-dependent mechanism. (*The Journal of Immunology*, 2004, 173: 6346-6356).

Asthma is an atopic inflammatory disorder of the airways that is characterized by increased airway hyperresponsiveness (AHR), eosinophil infiltration of the airways, and mucus hypersecretion that results in intermittent airway obstruction. The immune etiology of asthma is complex, but genetic and immunological analyses of atopic individuals have revealed that Th2-type cytokines are causally associated with allergies with a type 2 cytokine response being characterized by increased (Th2) cell development and production of IL-4, -5, -9, and -13 resulting in IgE production, mucus hyperplasia, and eosinophilia.

Fallon's laboratory demonstrated that *Schistosoma mansoni* infection protects mice from anaphylaxis through a regulatory mechanism induced by the worm. In a study to evaluated whether *S. mansoni* infection of mice, the mouse being the preferred animal model for studies on the immunobiology of schistosomiasis, altered susceptibility of the animals to OVA-induced AHR, which is also widely used as a model of human pulmonary inflammation. It was demonstrated that the worm stage of *S. mansoni* infection modulates mice so they are refractory to AHR. This is the first formal demonstration of a mechanism that human parasitic worms use to suppress allergen-induced airway inflammation.

The present invention will permit the development of formulations containing whole or fragments of parasites, including helminth worms such as *Schistosoma mansoni*, and the gastrointestinal nematode *H. polygyrus*, including any covalently or non-covalently modified formats thereof to be formulated, with or without adjuvants or permeability enhancers, and to be encapsulate within single or multiple layer, with the layers or polymer coatings of which being modified to ensure release at the most appropriate location along the intestine or colon/rectum. The result will be an optimized, tunable and modular orally administered antiallergenic delivery technology. In addition to the above mentioned diseases that have been explored, the current invention may also benefit broader applications, such as, but not limited to, asthma, celiac disease, food allergies and more general allergies.

Targeted Delivery of Conjugated Linoleic Acid (CLA)

Conjugated linoleic acid (CLA) is a collective term used to describe one or more positional and geometric isomers of linoleic acid, an essential fatty acid. Recent attention focused on CLA can be explained by the plethora of potential health benefits attributed to this unique fatty acid.

Dairy products and other foods derived from ruminant animals are the main dietary sources of CLA. The cis-9, trans-11 isomer is the predominant biologically active CLA isomer in bovine milkfat and in the overall diet of humans. Biological activity for other isomers, particularly the trans-10, cis-12 isomer, has recently been demonstrated. A variety of factors, such as the diet, can influence the CLA content of milkfat. Because the CLA content of dairy products is related to their fat content, CLA levels are greater in higher fat than in lower fat products. The finding that various dietary manipulations can increase the CLA content of milkfat may open the door for CLA-enriched dairy foods.

In vitro and experimental animal studies document a growing number of potential health benefits for CLA. These include: Anticarcinogenic Effects—CLA inhibits the proliferation of some cancers such as mammary, colorectal, prostate, and stomach cancers. Virtually all studies have used synthetic mixtures of CLA. For the first time, an anticarcinogenic effect has been demonstrated for naturally-occurring CLA in food (butter); Antiatherogenic Effects—CLA lowers total and LDL cholesterol as well as triglyceride levels and reduces the severity of atherosclerotic lesions in the aortas of experimental animals; Body Composition Changes—Intake of CLA reduces body fat and increases lean body mass in several species of growing animals; Enhanced Immune Function—CLA enhances select immune responses in experimental animals, while at the same time protecting against immune-induced cachexia or body wasting; Increased Bone Formation—CLA intake by growing animals increases the rate of bone formation by influencing factors that regulate bone metabolism; and Anti-Diabetic Effects—CLA improves glucose utilization and reverses symptoms of diabetes in laboratory animals genetically at risk for this disease.

Much remains to be learned about the underlying mechanism(s) by which CLA exerts its diverse physiological effects. A variety of mechanisms are likely to be involved. The wide spectrum of CLA's biological effects may be explained, in part, by the unique biological effects of specific CLA isomers. Although the cis-9, trans-11 CLA isomer appears to be responsible for a number of the potential health benefits attributed to CLA, new findings indicate that CLA's effects on lipid metabolism and body composition are due largely to the trans-10, cis-12 isomer.

The present invention will permit the development of formulations containing CLA or fractions or derivatives thereof, including any covalently or non-covalently modified formats thereof to be formulated, with or without adjuvants or permeability enhancers, and to be encapsulate within single or multiple layer, with the layers or polymer coatings of which being modified to ensure release at the most appropriate location along the intestine or colon/rectum. The result will be an optimized, tunable and modular orally administered product to enhance systemic absorption for systemic therapeutics or delivered to specific regions of the GIT to treat local intestinal or colonic diseases.

The present invention provides a multiple minicapsule modified release composition comprising at least one population of active ingredient-containing minicapsules which, upon administration to a patient, exhibits a single, bimodal or multimodal release profile throughout the entire gastro-intestinal tract or at pre-specified regions along the gastro-intestinal tract.

The multiple minicapsule or minisphere modified release composition may comprise at least two populations of active ingredient-containing minicapsules which, upon administration to a patient, exhibits a bimodal or multimodal release profile that results in a plasma profile within therapeutically effective pharmacokinetic parameters.

In one case the invention provides a multiple minicapsule modified release composition comprising at least two populations of active ingredient-containing minicapsules which, upon administration to a patient, exhibits a pulsatile release profile.

In another case the invention provides a multiple minicapsule modified release composition comprising at least two populations of active ingredient-containing minicapsules which, upon administration to a patient, results in a pulsatile plasma profile.

The invention also provides a multiple minicapsule modified release composition comprising at least two populations of active ingredient-containing minicapsules which, upon administration to a patient, produces a plasma profile substantially similar to the plasma profile produced by the administration of two or more IR dosage forms given sequentially.

The invention also provides a multiple minicapsule modified release composition comprising at least two populations of active ingredient-containing minicapsules in which the amount of the one or more active ingredients in the first population of minicapsules is a minor portion of the amount of the one or more active ingredients in the composition, and the amount of the one or more active ingredients in the one or more additional population of minicapsules is a major portion of the amount of the one or more active ingredients in the composition.

In another aspect the invention provides a multiple minicapsule modified release composition wherein each minicapsule contains one or more active ingredient combined in the minicapsule core, shell or coating or separately present in each to enable a sustained or zero-order pharmacokinetic profile through modification of the core formulation, the shell or minicapsule coating.

The invention further provides a multiple minicapsule modified release composition comprising at least two populations of different active ingredient-containing minicapsules in which the two or more actives are released concomitantly.

Alternatively, the invention provides a multiple minicapsule modified release composition comprising at least two populations of different active ingredient-containing minicapsules in which the two or more actives are released sequentially.

Yet another object of the invention is to provide a multiple minicapsule modified release composition to protect an acid-labile.

The invention provides a multiple minicapsule modified release composition to protect or degradative-enzyme sensitive active ingredients and to release such proximal to the intestinal epithelial cell wall or in the colon, in the lumen or proximal to the epithelial wall in the small intestine or colon.

In one case the invention provides a multiple minicapsule modified release composition whereby the active or actives are released in the ileum or colon, where the active is not absorbed but may yet be locally active.

In the invention the minicapsule core composition may include excipients in a liquid form that permit controlled or sustained release in conjunction with or independent of the shell or coating. Such forms can include various matrix structures or melt-extruded polymers or temperature modulated lipid-based excipients, including, but not limited to the Gattefosse Gelucire® range of saturated triglycerides or the Sasol range of Witepsol® saturated triglycerides which demonstrate considerable sustained release when exposed to the gastrointestinal environment.

The minicapsule core composition may include excipients in a semi-liquid or solid form that permit controlled or sustained release in conjunction with or independent of the shell or coating or where the core comprises the entire minicapsule or minisphere.

The pharmaceutically acceptable excipient may be chosen from carriers, fillers, extenders, binders, humectants, disintegrating agents, solution-retarding agents, absorption accelerators, wetting agents, absorbents, lubricants, stabilizers, coloring agents, buffering agents, dispersing agents, preservatives, organic acids, and organic bases.

The modified-release compositions of the invention may comprise an immediate-release core and a semi-permeable membrane. In some embodiments, the modified-release compositions of the invention may comprise a modified-release semi-solid core and a semi-permeable membrane.

The present invention also provides sustained release of drugs that otherwise are readily absorbed in the small intestine but exhibit limited colonic absorption is made possible through targeted release of formulations wherein the drug or other entity is pre-solubilised. Examples of such drugs include tacrolimus, carvedilol, cyclosporine and losartan.

The present invention allows for sustained release of carvediol concomitantly or sequentially with hydralazine for the treatment of certain cardiovascular conditions, including, but not limited to congestive heart failure, essential hypertension or others.

The present invention provides sustained release formulations of carvediol concomitantly or sequentially with hydralazine for the prevention or to reduce risk of certain cardiovascular conditions, including, but not limited to congestive heart failure, essential hypertension or others.

The present invention also permits development of sustained release tacrolimus or cyclosporine in combination with an antioxidant or nuclear factor kappa B inhibitor such as, but not limited to curcuminoids, such as, but not limited to curcumin, to reduce nephrotoxicity or increase effectiveness in treating inflammatory bowel disease or to enhance efficacy in the treatment of diabetes-related kidney disorders.

The present invention also permits development of sustained release tacrolimus, sirolimus cyclosporine in combination with mycophenolate motefil and/or other immunomodulators to enhance the management of post-transplant treatment.

The invention also includes methods of treating inflammatory bowel disease comprising administering to a subject in need thereof a pharmaceutical composition comprising a dose of a cyclosporine, sirolimus or tacrolimus, or pharmaceutically acceptable salts, esters and pro-drugs thereof, and at least one pharmaceutically acceptable excipient. Such formulations are preferentially developed to ensure release in the ileum and/or colon.

Yet another embodiment of this invention relates to methods of treating inflammatory bowel or irritable bowel syndrome disease comprising administering to a subject in need thereof a pharmaceutical composition comprising an effective hydroxylase inhibitor, including PHD inhibitors and asparaginyl hydroxylase inhibitors, such as but not limited to Hydralazine, DMOG or others and or covalent or non-covalent modified active or inactive entities, including nitric oxide donors (NO-donors).

Still another embodiment of this invention relates to methods of treating inflammatory bowel or irritable bowel syndrome disease comprising administering to a subject in need thereof a pharmaceutical composition comprising an effective calcium channel blocker, such as but not limited to nimodipine, verapamil, including various salts and enantiomers thereof or covalent or non-covalent modified active or inactive entities, including nitric oxide donors (NO-donors).

Another embodiment of this invention relates to methods of treating inflammatory bowel disease or irritable bowel syndrome comprising administering to a subject in need thereof a pharmaceutical composition comprising activators of Nuclear Factor Kappa B (NFκB), including, but not limited to, DMOG, Hydralazine, BAY 117082, Curcumin or others and/or covalent or non-covalent derivatives, including but not limited to, covalently attached nitric oxide donor groups, thereof, which also may inhibit apoptosis, with release of same targeted to the ileum or colon.

Still another embodiment of this invention relates to methods of treating inflammatory bowel disease comprising administering to a subject in need thereof a pharmaceutical composition comprising Tacrolimus or Cyclosporine A and a curcuminoid, such as, but not limited to, curcumin, with release of same targeted to the ileum or colon.

Yet another embodiment of this invention relates to methods of treating inflammatory bowel disease comprising administering to a subject in need thereof a pharmaceutical composition comprising a TNFα inhibitor, including small molecules as well as antibodies or other biopharmaceuticals and/or covalent or non-covalent derivatives thereof with release of same targeted to the ileum or colon.

One more embodiment of this invention relates to methods of treating inflammatory bowel disease or irritable bowel syndrome comprising administering to a subject in need thereof a pharmaceutical composition comprising a kappa B alpha (IKκBα) kinase inhibitor and/or covalent or non-covalent derivatives thereof with release of same targeted to the ileum or colon.

Yet another embodiment of this invention relates to methods of treating inflammatory bowel disease or irritable bowel syndrome comprising administering to a subject in need thereof a pharmaceutical composition comprising nicotine and/or derivatives thereof with release of same targeted to the ileum or colon.

Yet another embodiment of this invention relates to methods of treating inflammatory bowel disease or irritable bowel syndrome comprising administering to a subject in need thereof a pharmaceutical composition comprising a dose of an NO donor, such as, but not limited to, NOC5 [3-(2-hydroxy-1-(methylethyl)-2-nitrosohydrazino)-1-propanamine], NOC12 [N-ethyl-2-ethyl-hydroxy-2-nitrosohyrdrazino-ethanamine], nitroglycerine or other therapeutics modified to include a conjugated NO donor.

Another embodiment of the present invention relates to targeted delivery of natural plant, marine or other extracts, including essential oils such as Neem, aloe vera and the omega range of polyunsaturated oils, including EPA, DHA and CLA, with or without plant extracts such as, but not limited to, berry extracts, tripala, tumeric, resveratrol, resorcinolic/phenolic lipids, flavanoids and any natural or synthetic derivatives thereof.

Another embodiment of the present invention relates to a pharmaceutical composition comprising a combination of any of the above examples released anywhere along the gastrointestinal tract.

In another embodiment, this invention relates to methods of treating other colonic diseases, including, but not limited to, carcinomas, polyps, and/or cysts of the colon and/or rectum comprising administering to a subject in need thereof a pharmaceutical composition comprising a dose of a COX-II inhibitor, such as, but not limited to, Celebrex or an antimetabolite such as Methotrexate.

In an additional embodiment of the present invention, targeted release of formulations of small molecules or macromolecules, including vaccines and immunotherapeutics, that are preferentially absorbed by lymphoid tissue in the colon or elsewhere in the gastrointestinal tract is included.

A further embodiment of the present invention, targeted release of formulations to treat liver cirrhosis or other fibrosis-related conditions, including calcium channel blockers such as, but not limited to, nifedipine or hydroxylase inhibitors, such as, but not limited to, hydroxylase or nitric oxide donors or derivatives thereof, administered singly or in combination. Such active agents may be formulated with entities that preferentially target the liver, including conjugated cyclodextrins or derivatives thereof.

Yet another embodiment is the co-administration of immediate release proximal tubule diuretics and delayed release distal tubule diuretics, such as, but not limited to mannitol, acetazoloamide, furosemide, spironolactone, amiloride, triamterene, butnetanide, ethacrynic acid, or thiazides for the treatment of hypertension and other nephron-related disorders.

An additional embodiment of the invention is a single or combination product to treat diabetes or complications associated with diabetes that includes one or other of insulin, insulin sensitizers, sulphonamides, glucagons-like peptides or the like, released concomitantly or sequentially as required.

One other embodiment of the invention is a single or combination product to treat one or more cardiovascular disease that comprises a pharmaceutical formulation comprising one or other of a statin, a bile acid sequestrant, a cholesterol absorption inhibitor, a lipid absorption inhibitor, an antioxidant, aspirin, a fibrate, an ACE inhibitor, an ATII receptor inhibitor, a nitric oxide donor, a beta blocker, a calcium channel blocker and so on, released concomitantly or sequentially as required.

Still a further embodiment of this present invention is targeted gastrointestinal release of formulations containing antibodies, including fragments thereof, to maximize systemic bioavailability or enhanced local intestinal efficacy.

Still an additional embodiment of this present invention is targeted gastrointestinal release of formulations containing nucleic acid therapeutics, including antisense oligonucleotide, siRNAs and gene therapy constructs, to maximize systemic bioavailability or enhanced local intestinal efficacy.

Still an additional embodiment of this present invention is targeted gastrointestinal release of formulations containing peptides, proteins or carbohydrates, including modified or conjugated constructs, to maximize systemic bioavailability or enhanced local intestinal efficacy.

Another embodiment of the current invention relates to non-covalent complexion of a drug with a carrier such as cyclodextrins, maltodextrins, dextrins or modifications thereof and targeting the release of such to the specific sites along the gastrointestinal tract.

Another particular embodiment of the present invention relates to small molecules or biopharmaceutical molecules, which may include siRNA constructs, which have been conjugated to entities that serve either to enhance stability and/or increase the hydrophilic nature of the active drug molecule and targeted in the release of such conjugates to the small intestine or colon.

Specifically, another embodiment of the present invention relates to small molecules or biopharmaceutical molecules, which may include siRNA constructs, to which lipophilic entities have been conjugated to enhance stability and/or increase intestinal wall permeability and to target such conjugated drugs to specific sites along the gastrointestinal tract to maximise absorption for enhances systemic efficacy or to maximise local intestinal activity.

Yet a further embodiment of the present invention is targeted gastrointestinal release of formulations containing conjugated drugs, the conjugation which prevents absorption into the systemic or lymphatic vasculature yet retains local intestinal therapeutic efficacy.

Still a further embodiment of the present invention is targeted gastrointestinal release of formulations comprising poorly soluble actives, including small molecules and biopharmaceuticals formulated with amongst other excipients, permeability enhancers, such as, but not limited to, sodium dodecanoate (C12), Sodium Caprate (C10) and/or Sodium Palmitate (C16).

One more embodiment of the present invention is targeted gastrointestinal release of formulations containing live or live attenuated organisms, including bacteria or genetically modified bacteria and/or live or live-attenuated viruses.

In the current invention, in the development of treatments for inflammatory bowel disease, the active pharmaceutical ingredient is interchangeable, including any one or combination of cyclosporine A, tacrolimus, sirolimus, hydralazine, DMOG, proply- and/or asparaginyl hydroylase inhibitors, EPA, DHA, natural plant extracts, natural marine extracts or other biological and active entities, which may include siRNA constructs.

In the current invention, in the development of treatments for Graft-Versus-Host Disease, the active pharmaceutical ingredient is interchangeable, including any one or combination of cyclosporine A, tacrolimus, sirolimus, EPA, DHA, natural plant extracts, natural marine extracts or other biological and active entities, which may include siRNA constructs.

In the current invention, the immunological modulating entities, including antigens, adjuvants, emulsions, oils, and small molecules are interchangeable and may be utilised for the development of vaccines, oral tolerance modulators and allergen modulators, which may include siRNA constructs.

The invention allows for the development of solid-, semi-solid or liquid-filled minicapsules comprising one or more layer and produced using conventional seamless minicapsule processes, modified melt extrusion, non-pareil coating, non-pareil drug layering or other processes that enable the production of the desired dosage form.

The invention allows for a broad range of controlled release polymer coatings to be applied. Coating materials may include any combination of the commercially available acrylic-, methacrylic-, ethylcellulose-based polymers (such as, but not limited to the Eudragit™ and Surelease® range), as well as other polymers with natural polysaccharides, including, but not limited to amylose, pectin, alginate, amylopectin, chitosan, galactomannan, guar gum and any derivatives thereof, has the potential to customise how, where and when drugs are released from the underlying or embedded solid, semi-solid or liquid forms. In all examples cited in this specification, any specific polymer may be interchanged or combined with any other polymer to enable the required release profile according to the preferred optimal therapeutic outcome envisaged.

The invention provides a solid oral dosage form comprising the multiple minicapsule modified release composition of the present invention, the said minicapsules being one layer or multiple layer. Where a two layer minicapsule has a shell comprised of a gelling agent with a controlled release polymer or other coating or comprised of controlled release polymer or other materials.

The invention also provides a sachet format comprising multiple minicapsule modified release composition of the present invention for ease of administration to paediatrics, geriatrics or other patient populations with swallowing difficulties.

The invention will be more clearly understood from the following examples.

EXAMPLES

The FIGS. 1 to 4 schematically illustrate the various minicapsule or minisphere forms that the present invention uses. Active drug substances may be formulated using one or more populations of such minicapsule or minisphere structures.

Figure 2:
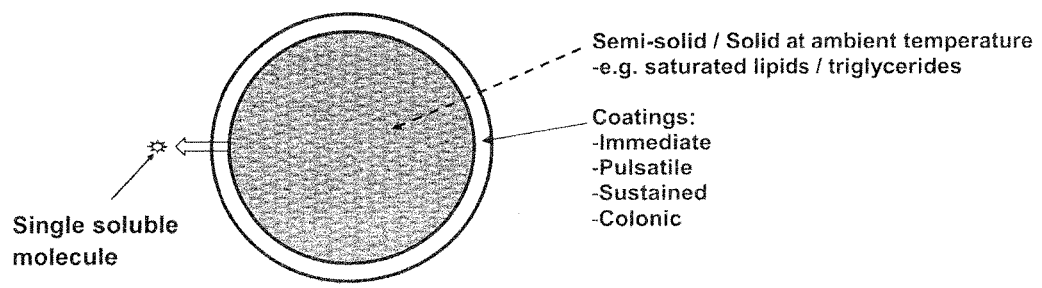
FIG. 2 is a schematic of a Semi-solid- or solid-filled minicapsule/minisphere, wherein the active is solubilised or in a suspension form, with controlled release polymer coatings; The open arrow represents the release of a drug molecule into the external medium, where it is fully soluble when released (Format 2)
Figure 3:
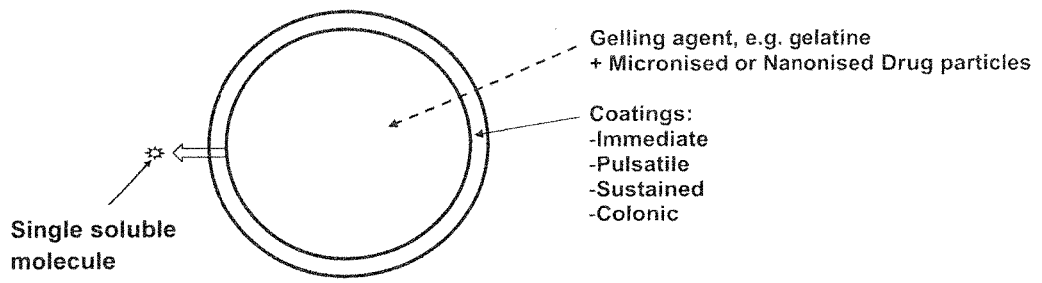
FIG. 3 is a schematic of a gelling agent encapsulating enhanced solubilised or permeabilised active substances, including substances in micronised or nanonised form, primarily in a dispersion form, either crystalline or amorphous formats; The open arrow represents the release of a drug molecule into the external medium, where it is fully soluble when released (Format 3)
Figure 4:
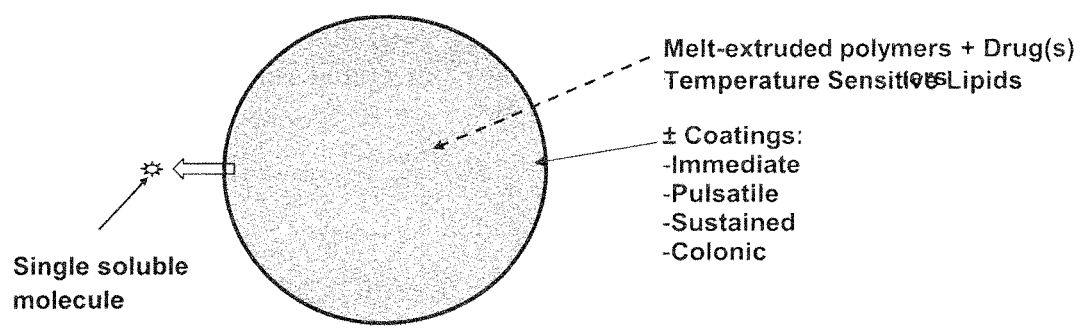
FIG. 4 is a schematic of active substances, in crystalline or amorphous form, blended with extrudable or other polymers which are melt-extruded, granulated, drug layered, spheronised or otherwise processed which may be further coated to permit controlled or targeted release along the gastrointestinal tract or, alternatively, are inherently controlled release; The open arrow represents the release of a drug molecule into the external medium, where it is fully soluble when released (Format 4)

FIG. 1—Liquid-filled minicapsule with controlled release polymer coatings. This format comprises an active substance encapsulated using a suitable gelling agent that is further coated to permit controlled or targeted release along the gastrointestinal tract. The active substance is in an enhanced solubilised or permeabilised form. The open arrow represents the release of a drug molecule into the external medium, where it is fully soluble when released (Referred to as Format 1);

FIG. 2—Semi-solid- or solid-filled minicapsule/minisphere with controlled release polymer coatings. This format comprises an active substance, liquid at processing temperature, encapsulated using a suitable gelling agent that is further coated to permit controlled or targeted release along the gastrointestinal tract. The active substance is in an enhanced solubilised or permeabilised form. The open arrow represents the release of a drug molecule into the external medium, where it is fully soluble when released (Referred to as Format 2);

FIG. 3—Gelling agent encapsulating enhanced solubilised or permeabilised active substances, including substances in micronised or nanonised form, either crystalline or amorphous formats. The resulting solid spherical structures may be further coated to permit controlled or targeted release along the gastrointestinal tract. The open arrow represents the release of a drug molecule into the external medium, where it is fully soluble when released (Referred to as Format 3);

FIG. 4—Active substances, in crystalline or amorphous form, blended with extrudable or other polymers which are melt-extruded, drug layered, spheronised or otherwise produced which may be further coated to permit controlled or targeted release along the gastrointestinal tract or, alternatively, are inherently controlled release. The open arrow represents the release of a drug molecule into the external medium, where it is fully soluble when released (Referred to as Format 4).

Example 1

As per FIG. 1 above, Example 1 represents a controlled release liquid-filled minicapsule of the Format 1 variety. The core formulation was prepared as follows. Tacrolimus was dissolved in a suitable volume of ethanol. Once dissolved, the solution was blended with a suitable mix of Labrafil and Olive oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises Tacrolimus in an enhanced solubilised and permeabilised formulation. In addition, the core formulation does enable a degree of sustained release.

TABLE 1

Once-daily Tacrolimus

| Ingredients | % w/w |
|---|---|
| Core Composition | |
| Tacrolimus | 3.25 |
| Labrafil | 36.4 |
| Olive Oil | 47.65 |
| Ethanol | 12.7 |
| Shell Composition | |
| Gelatin | 90.0 |
| Sorbitol | 10.0 |

Example 2

Figure 5:
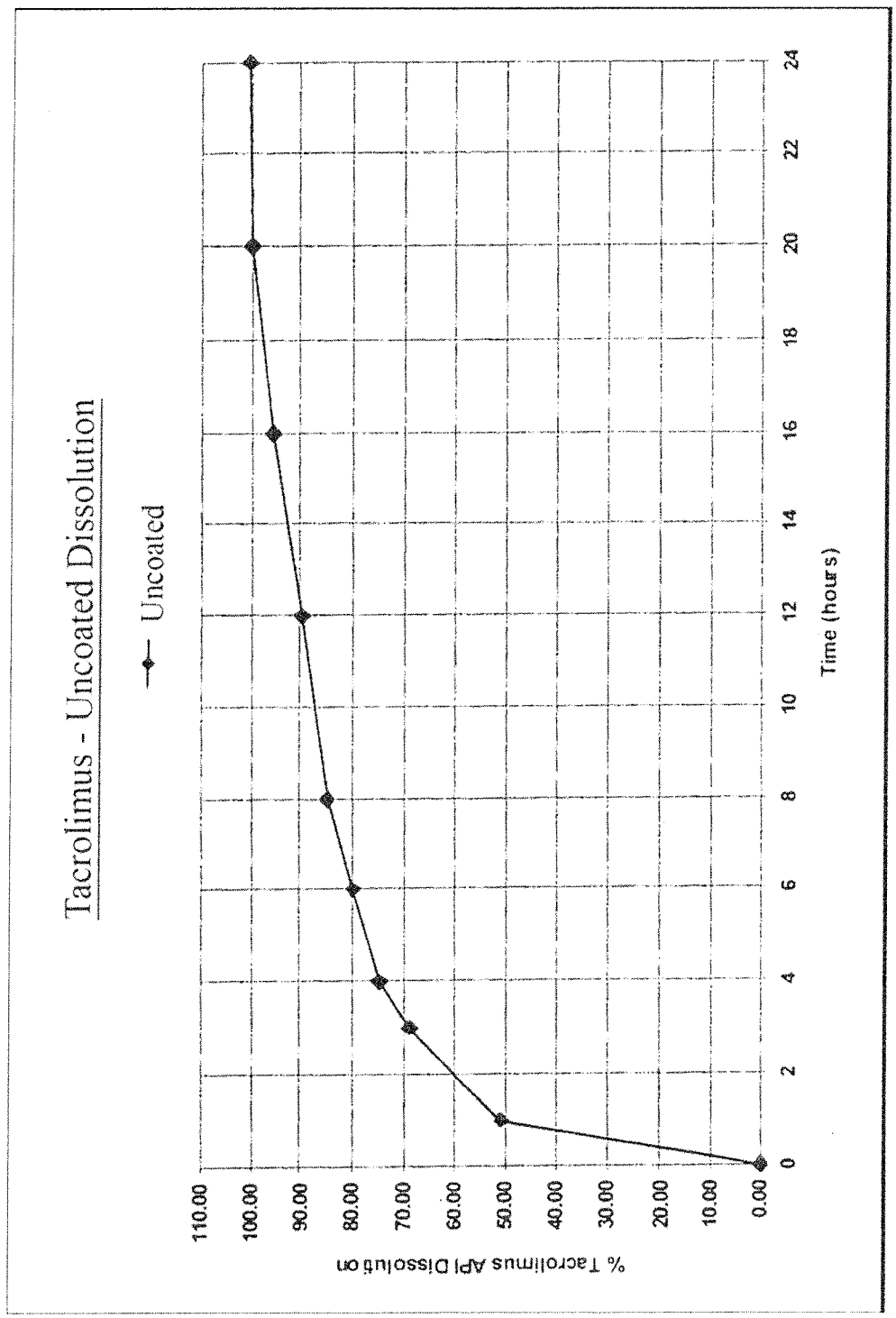
FIG. 5 is a graph showing the dissolution profile for uncoated tacrolimus minicapsules (Format 1)

Tacrolimus release from uncoated minicapsules of Example 1 (Format 1): Dissolution profiles in FIG. 5 demonstrate the following release of tacolimus from minicapsules expressed as a percentage of the total minicapsule content: less than 55% within 1 hr; less than 80% within 4 hrs; less than 90% within 12 hrs and less than or equal to 100% at 24 hr.

Example 3

Figure 6:
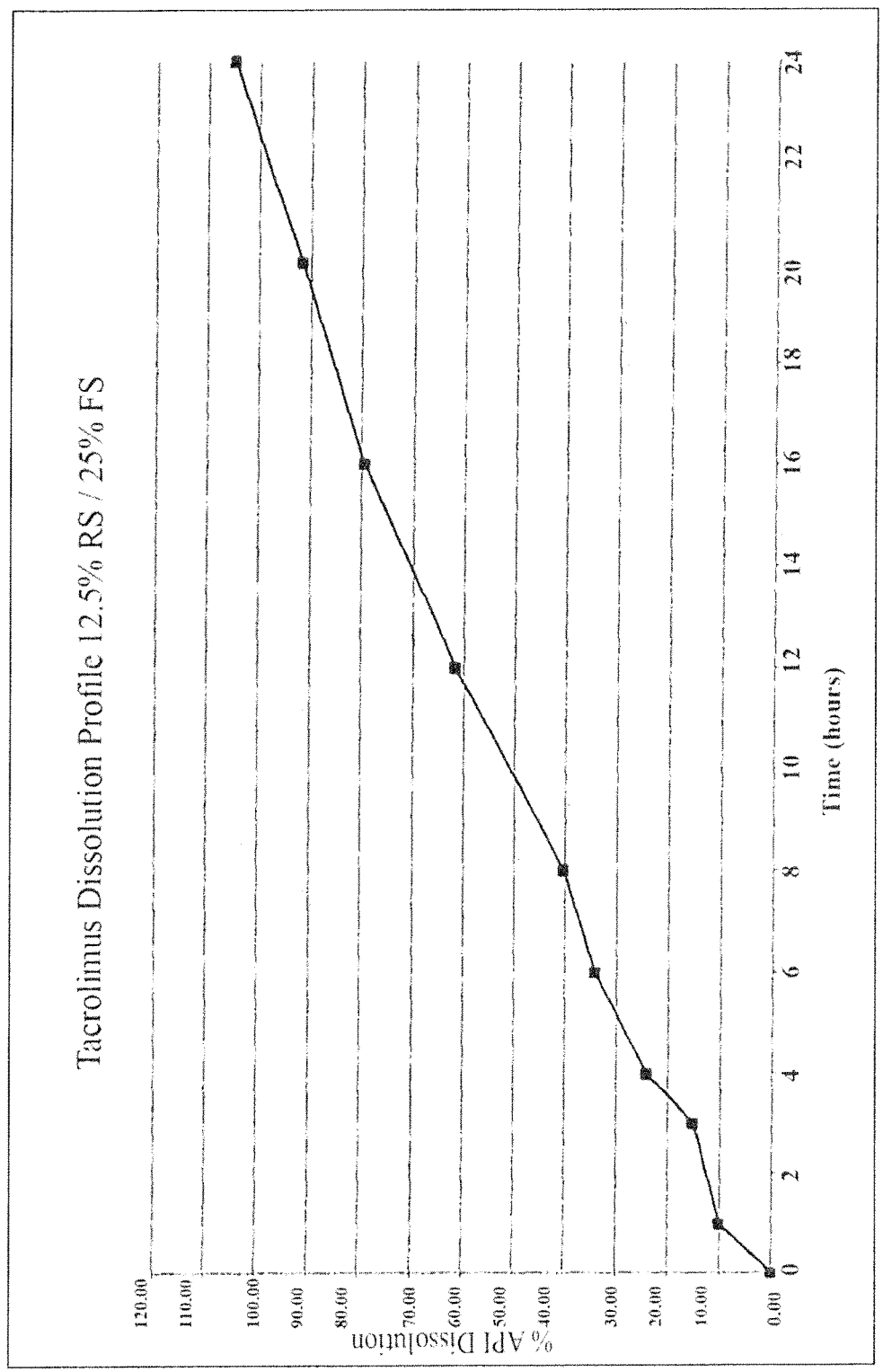
FIG. 6 is a graph showing the dissolution profile for tacrolimus minicapsules coated with 12.5% Eudragit™ RS30D followed by 25% Eudragit™ FS30D (Format 1)

Tacrolimus release from minicapsules of Example 1 (Format 1) coated with 12.5% weight gain Eudragit™ RS30D followed by 25% weight gain Eudragit™ FS30D: Dissolution profiles in FIG. 6 demonstrate the following release of tacolimus from minicapsules expressed as a percentage of the total minicapsule content: less than 10% within 1 hr; less than 30% within 4 hrs; less than 75% within 12 hrs and less than or equal to 100% at 24 hr. This is suited either to a once-daily systemic absorption product or an ileum/colon-specific product.

Example 4

Figure 7:
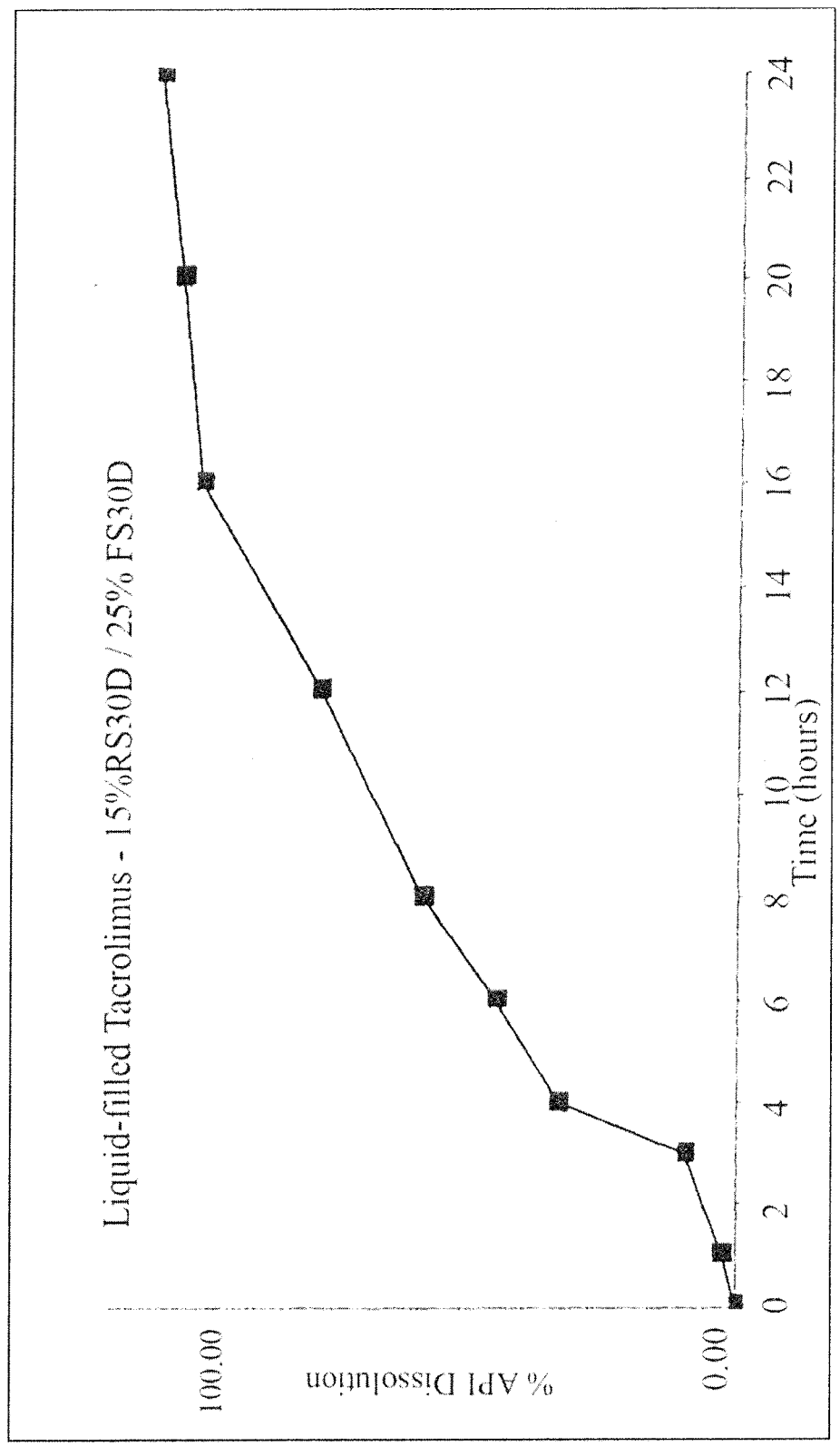
FIG. 7 is a graph showing the dissolution profile for 15% weight gain Eudragit™ RS30D/25% weight gain Surelease®—coated tacrolimus minicapsules (Format 1)

Tacrolimus release from minicapsules of Example 1 (Format 1) coated with 15% weight gain Eudragit™ RS30D followed by 25% weight gain Eudragit™ FS30D: Dissolution profiles in FIG. 7 demonstrate the following release of tacolimus from minicapsules expressed as a percentage of the total minicapsule content: less than 10% within 1 hr; less than 30% within 4 hrs; less than 75% within 12 hrs and less than or equal to 100% at 24 hr. This is suited either to a once-daily systemic absorption product or, more particularly, an ileum/colon-specific product.

Example 5

As per FIG. 2 above, Example 5 represents a controlled release liquid-filled minicapsule of the Format 2 variety. To develop a semi-solid or solid-filled capsule, the core formulation was prepared as follows: Ovalbumin (OVA) was dissolved in a suitable volume of blended Lecithin and Saturated Triglycerides (Hard Fat—Witespol® H15), heated and stirrer until in solution.

The shell solution was prepared as follows: Appropriate quantities of gelatine, sodium hydroxide, HP-55 and water were mixed, stirred and heated to 70 degrees Celsius until in solution.

The minicapsules were prepared using a Spherex Labo to produce 2-layer minicapsules, the core of which comprises ovalbumin in solution.

TABLE 2

Oral Vaccine

| Formulation | | Formulation 1 |
|---|---|---|
| Formulation of shell solution (Wt %) | Water | 82.5 |
| | Gelatin | 10.5 |
| | Glycerin | 1.75 |
| | Chitosan | 1.75 |
| | HP-55 | 3.15 |
| | NaoH | 0.35 |
| Formulation of core solution (Wt %) | Hard Fat | 88 |
| | Lecithin | 10 |
| | Ovalbumin | 2 |

Ovalbumin (antigen) and Chitosan (adjuvant) is released from uncoated minicapsules as follows: 0% released within 1 hour and 100% within 8 hours.

Example 6

As per FIG. 2 above, Example 6 represents a controlled release liquid-filled minicapsule of the Format 2 variety. To develop a semi-solid or solid-filled capsule, the core formulation was prepared as follows: Ovalbumin was mixed with Algel (Alum Adjuvant) and Poly I:C (Inosine: Cytosine) methylated—oligonucleotide, dissolved in a suitable volume of blended Lecithin and Saturated Triglycerides (Hard Fat—Witespol® H15), heated and stirred until in solution.

The shell solution was prepared as follows: Appropriate quantities of gelatine, sodium hydroxide, HP-55 and water were mixed, stirred and heated to 70 degrees Celsius until in solution.

The minicapsules were prepared using a Spherex Labo to produce 2-layer minicapsules, the core of which comprises ovalbumin in solution. To enable small intestinal and colonic delivery the minicapsules were coated with 12.5% Surelease®. To enable mucoadhesion, the minicapsule shell contained chitosan.

TABLE 3

Oral Vaccine with Poly I:C and Alum as Adjuvants

| Formulation | | % w/w |
|---|---|---|
| Formulation of shell solution (Wt %) | Water | 82.5 |
| | Gelatin | 10.5 |
| | Glycerin | 1.75 |
| | Chitosan | 1.75 |
| | HP-55 | 3.15 |
| | NaoH | 0.35 |
| Formulation of core solution (Wt %) | Hard Fat(a) | 81.45 |
| | Lecithin | 9.05 |
| | Ovalbumin | 1 |
| | Algel | 7.5 |
| | Poly I; C | 1 |

Ovalbumin (antigen) and Chitosan (adjuvant) is released from uncoated minicapsules as follows: 0% released within 1 hour and 100% within 12 hours.

Example 7

Figure 8:
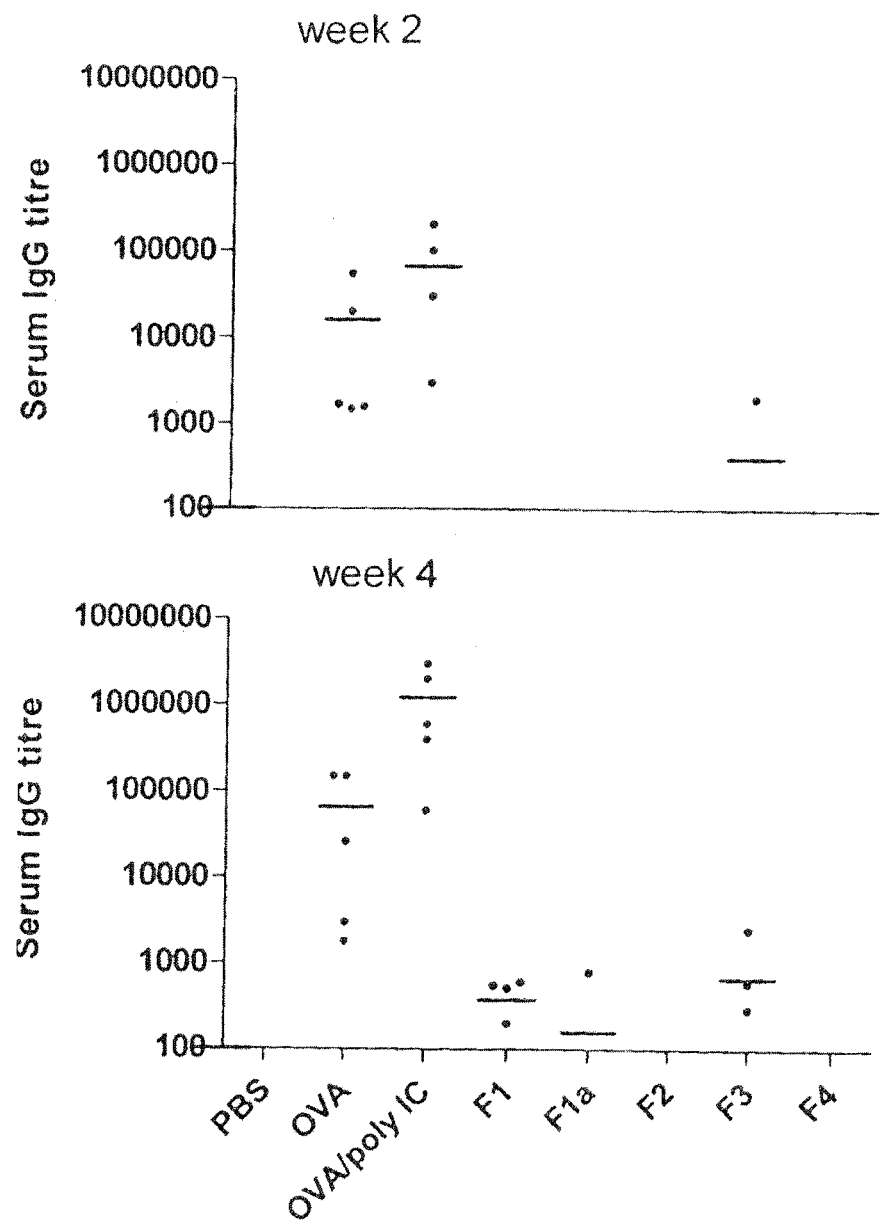
FIG. 8 represents the serum IgG responses following immunisation with OVA and OVA and poly I:C after the initial series of immunisations and particular after booster immunisation. The dots refer to antibody titres in individual mice and the line represents the mean titre for the group (Format 2)

FIG. 8 represents the immune response in mice immunised with minicapsules as described in Example 5 and Example 6. Administration of 100 µg ovalbumin with the adjuvant poly I:C in minicapsule formulations induces serum IgG responses. Mice were immunised on 3 consecutive days on week 0 followed by an identical series of booster immunisations at week 2. Serum samples were collected prior to the booster and one week following the booster and antigen specific IgG was assessed by ELISA. Immunisation with OVA or particularly OVA and poly I:C induced strong serum IgG responses after the initial series of immunisations and particular after booster immunisation Example 8

Figure 9:
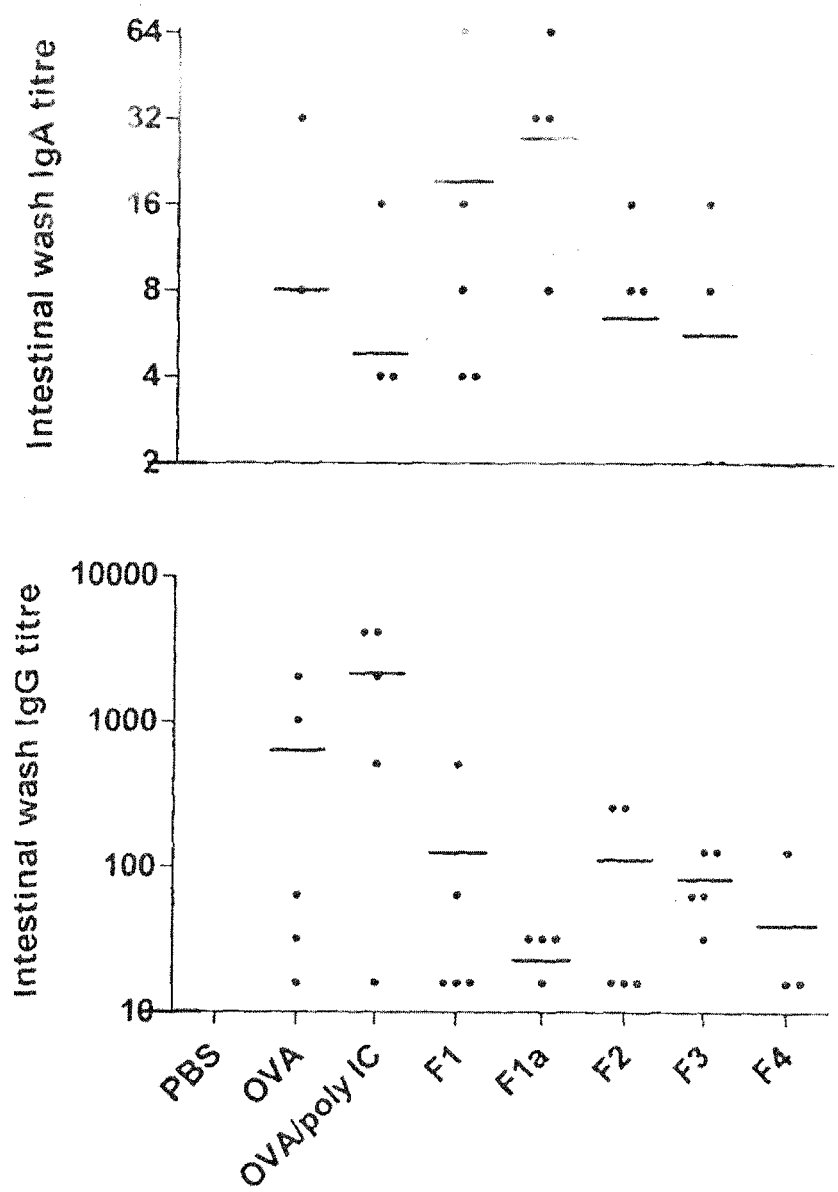
FIG. 9 represents intestinal mucosal IgA and IgG responses following immunisation with of mice with OVA in solution or uncoated and coated minicapsules containing OVA and poly I:C. The dots refer to antibody titres in individual mice and the line represents the mean titre for the group (Format 2)

FIG. 9 represents the immune response in mice immunised with minicapsules as described in Example 5 and Example 6. Administration of ovalbumin in coated minicapsule formulations is more effective in the induction of mucosal IgA (Immunoglobulin A) responses than the delivery of OVA with the adjuvant poly I:C. Mice were immunised on 3 consecutive days on week 0 followed by an identical series of booster immunisations at week 2. Intestinal washes were collected one week following the booster and antigen specific IgA and IgG was assessed by ELISA. This indicates that the protection of OVA from proteolysis by means of miniencapsulation can enhance the induction of a mucosal IgA response. Mucosal antibody responses IgG In terms of the titres of antigen specific IgG in the intestinal washes the highest responses were detected in mice immunised with OVA in solution or OVA and poly I:C.

Example 9

Figure 10:
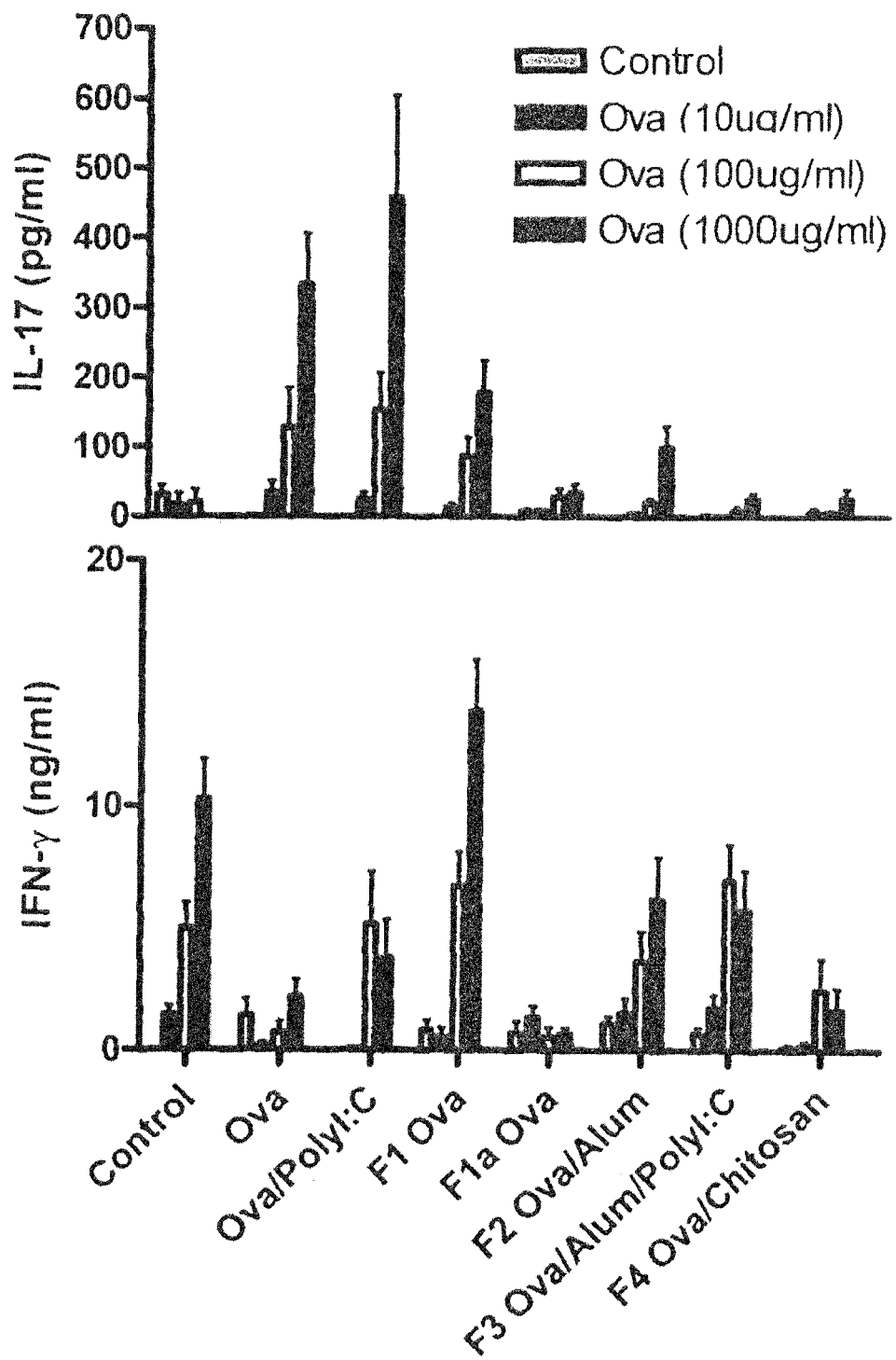
FIG. 10 represents splenic T-cell responses in mice following immunisation of mice with uncoated and coated minicapsules containing OVA with poly IC, as measured by IL-17 cytokine secretion and IFN-γ response on re-stimulation with antigen (Format 2)

FIG. 10 represents the immune response in mice immunised with minicapsules as described in Example 5 and Example 6. Immunisation with OVA, as per Examples 5 and 6, induced a strong antigen specific IFN-γ production by spleen cells. Mice were immunised on 3 consecutive days on week 0 followed by an identical series of booster immunisations at week 2. Spleen cells were re-stimulated with antigen 7 days after the booster immunisation and IL-17 and IFN-γ concentrations were determined by ELISA after 3 days. Enteric administration of OVA with chitosan induced a strong IFN-γ response on re-stimulation with antigen.

Example 10

Figure 11:
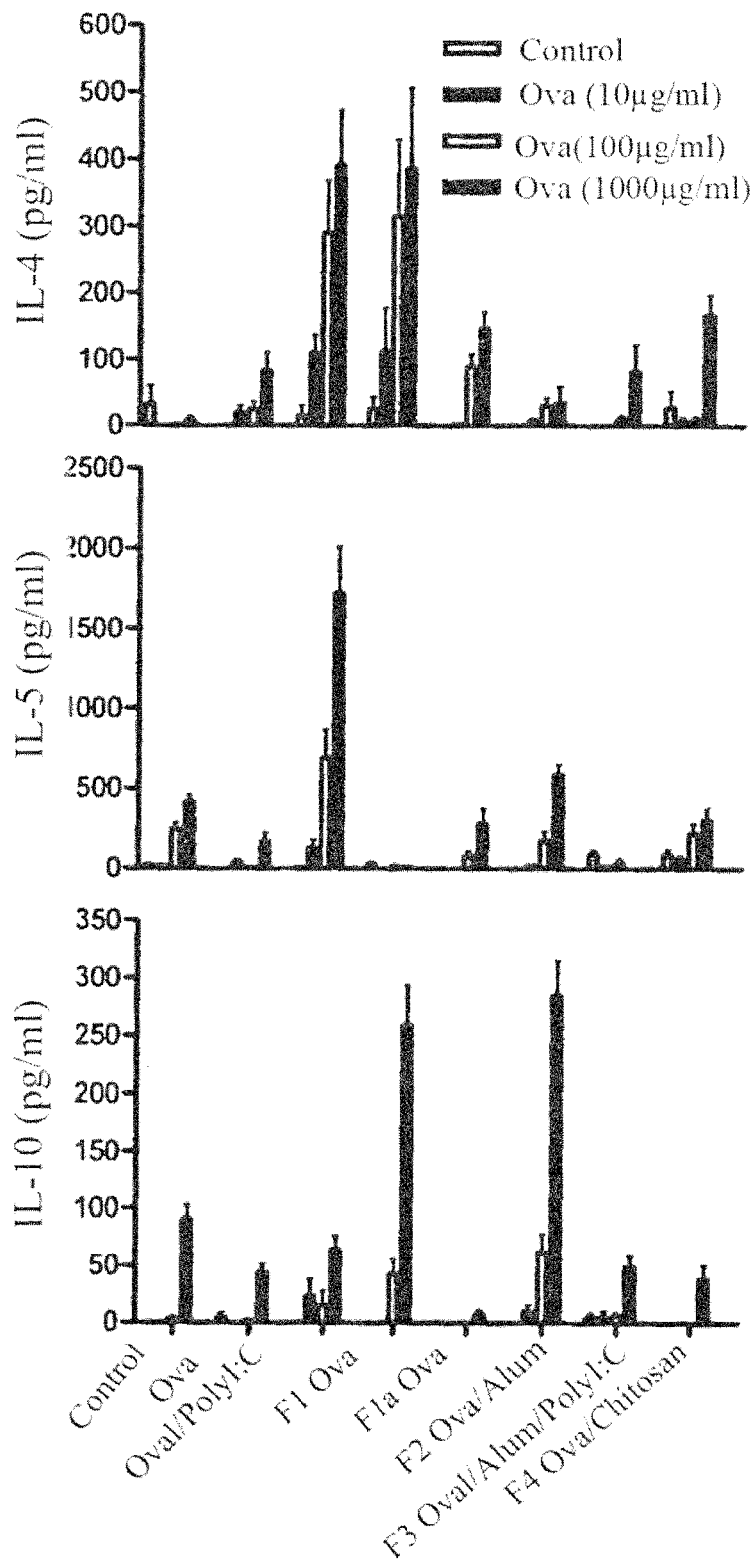
FIG. 11 represents splenic T-cell responses in mice following immunisation of mice with uncoated and coated minicapsules containing OVA with poly IC, as measured by IL-4, IL-5 and IL-10 cytokine secretion and IFN-γ response on re-stimulation with antigen (Format 2)

FIG. 11 represents the immune response in mice immunised with minicapsules as described in Example 5 and Example 6. Immunisation with OVA, as per Examples 5 and 6, induced strong antigen specific IL-4 and IL-10 production by spleen cells. Mice were immunised on 3 consecutive days on week 0 followed by an identical series of booster immunisations at week 2. Spleen cells were restimulated with antigen 7 days after the booster immunisation and IL-4, IL-5 and IL-10 concentrations were determined by ELISA after 3 days. Responses in mice immunised with uncoated minicapsules (Example 5) were weaker than in the case of the coated minicapsules (Example 6) suggesting that the enteric coat on the particles protected OVA such that more potent T cell responses were induced.

Example 11

Figure 12:
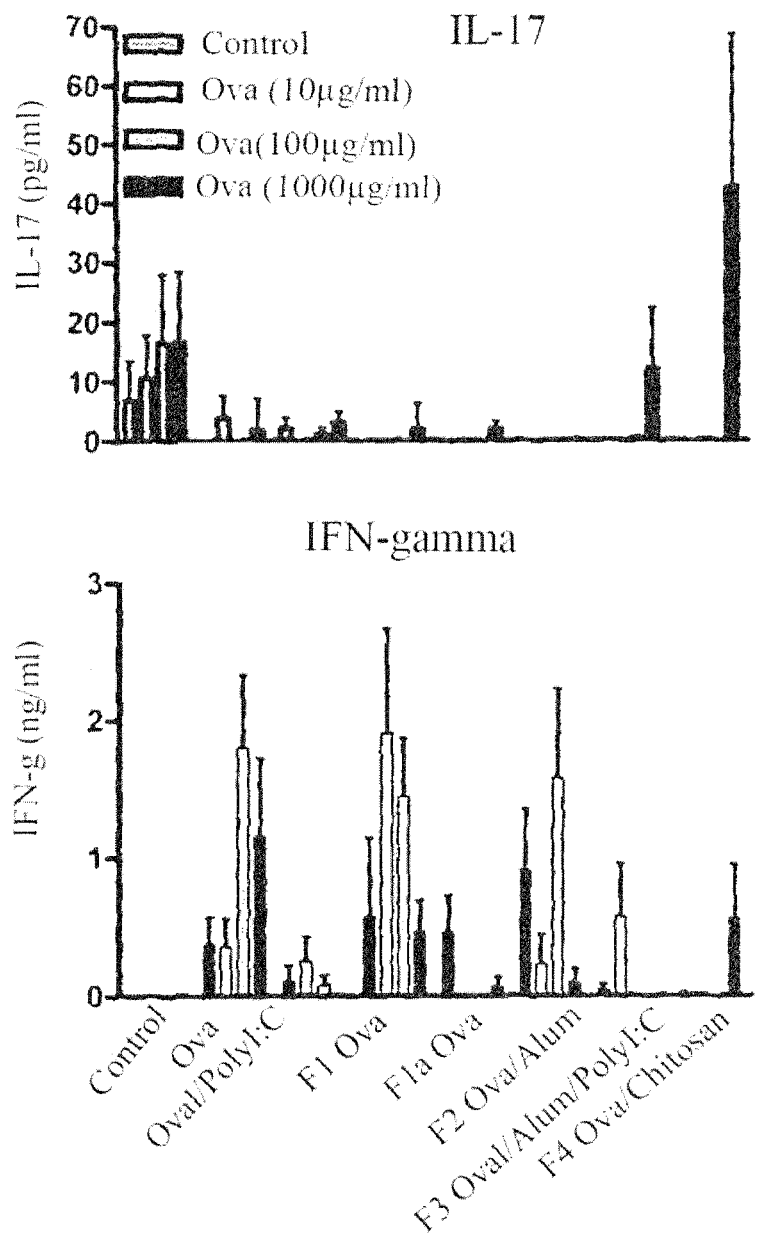
FIG. 12 represents mesenteric lymph node T-cell responses in mice following immunisation with uncoated and coated minicapsules containing OVA with poly IC, as measured by secretion of IL-4, IL-5 and IFN-γ response on re-stimulation with antigen (Format 2)

FIG. 12 represents the immune response in mice immunised with minicapsules as described in Example 5 and Example 6. Immunisation with OVA in uncoated minicapsules (Example 5) induces strong antigen specific IFN-γ production by mesenteric lymph node cells. Mice were immunised on 3 consecutive days on week 0 followed by an identical series of booster immunisations at week 2. Spleen cells were restimulated with antigen 7 days after the booster immunisation and IL-17 and IFN-γ concentrations were determined by ELISA after 3 days. The uncoated formulation (Example 5) was more effective than the coated formulation (Example 6) in terms of inducing antigen specific T cells secreting IL-4, IL-5 and IFN-γ.

Example 12

As per FIG. 3 above, Example 12a dispersion of micronized (or nanonized) drug, in this case micronized tacrolimus dispersed in a solid gelling agent and is representative of Format 3. The solid minicapsules (minispheres) were prepared as follows: Appropriate quantities of micronised tacrolimus, gelatine and sorbitol are added to water and heated to 80° C., continually stirring until in a homogeneous solution. The solution is then processed into solid minispheres at an appropriate flow rate and vibrational frequency. The resulting minispheres are cooled in oil. The cooled minispheres are harvested and centrifuged to remove residual oil and dried overnight.

TABLE 4

1-Layer Micronized Tacrolimus Minicapsules (Minispheres)

| Ingredients | % w/w |
|---|---|
| Core Composition | |
| Tacrolimus (Micronised) | 2.5 |
| Gelatin | 87.5 |
| Sorbitol | 9.7 |

To enable the development of a once-daily or an ileum- and colon-specific product, the minicapsules are coated with a range of sustained release polymers, namely differing weight gains of Surelease®, ranging from 0 to 30% weight gain, or variable weight gains of Surelease® plus variable concentrations of pectin.

Example 13

Figure 13:
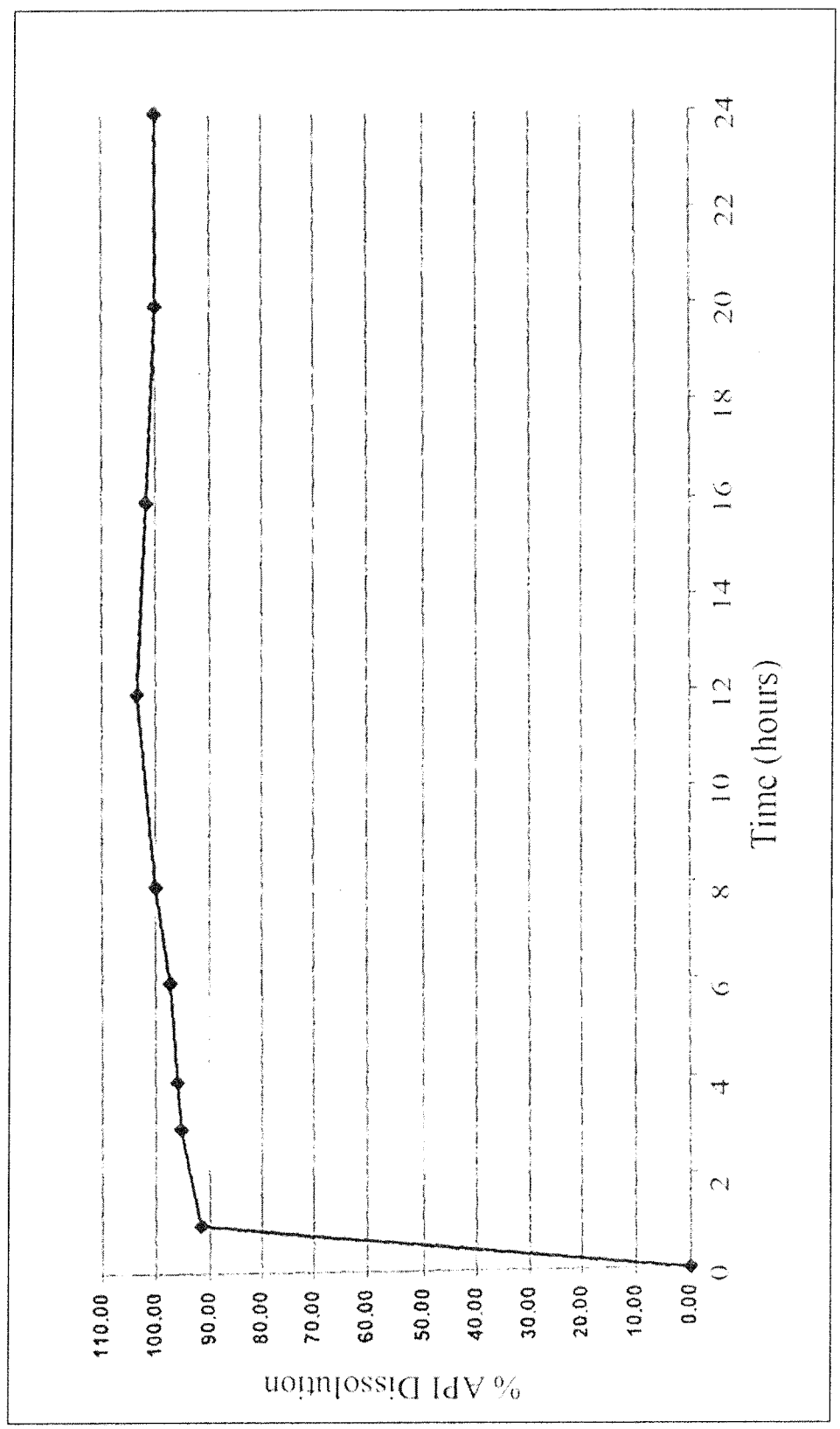
FIG. 13 is a graph showing the dissolution profile for uncoated micronized tacrolimus solid minicapsules (Format 3)

Tacrolimus release from uncoated minicapsules, prepared as per Example 12: Dissolution profiles in FIG. 13 demonstrate the following release of tacolimus from minicapsules expressed as a percentage of the total minicapsule content: greater than 90% within 1 hr and less than or equal to 100% at 4 hrs.

Example 14

Figure 14:
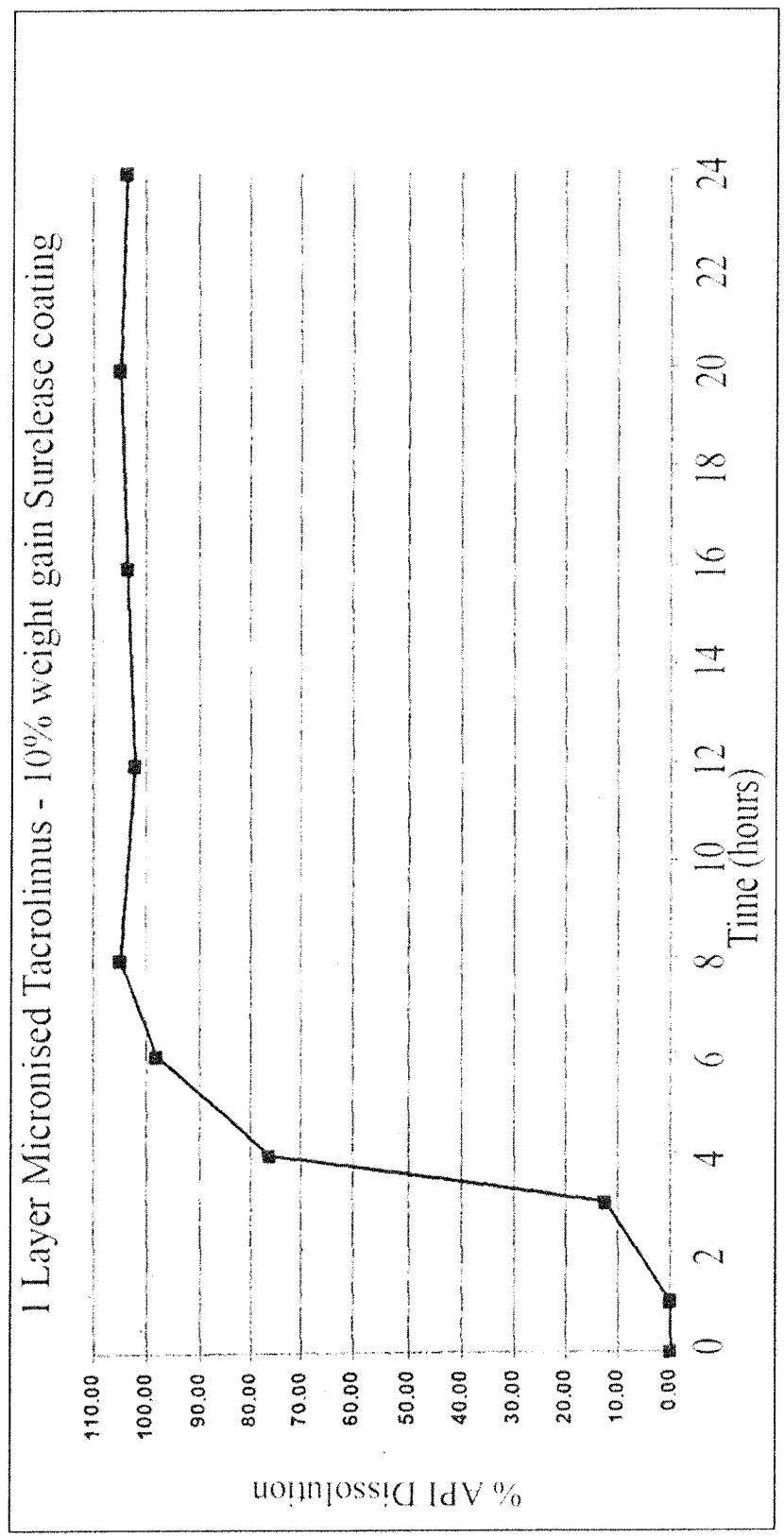
FIG. 14 is a graph showing the dissolution profile for 10% weight gain Surelease® coated micronized tacrolimus solid minicapsules (Format 3)

Tacrolimus release from minicapsules, prepared as per Example 12, coated with 10% weight gain Surelease®: Dissolution profiles in FIG. 14 demonstrate the following release of tacolimus from minicapsules expressed as a percentage of the total minicapsule content: less than 10% within 1 hr; less than 95% within 4 hrs and less than or equal to 100% at 8 hr.

Example 15

Figure 15:
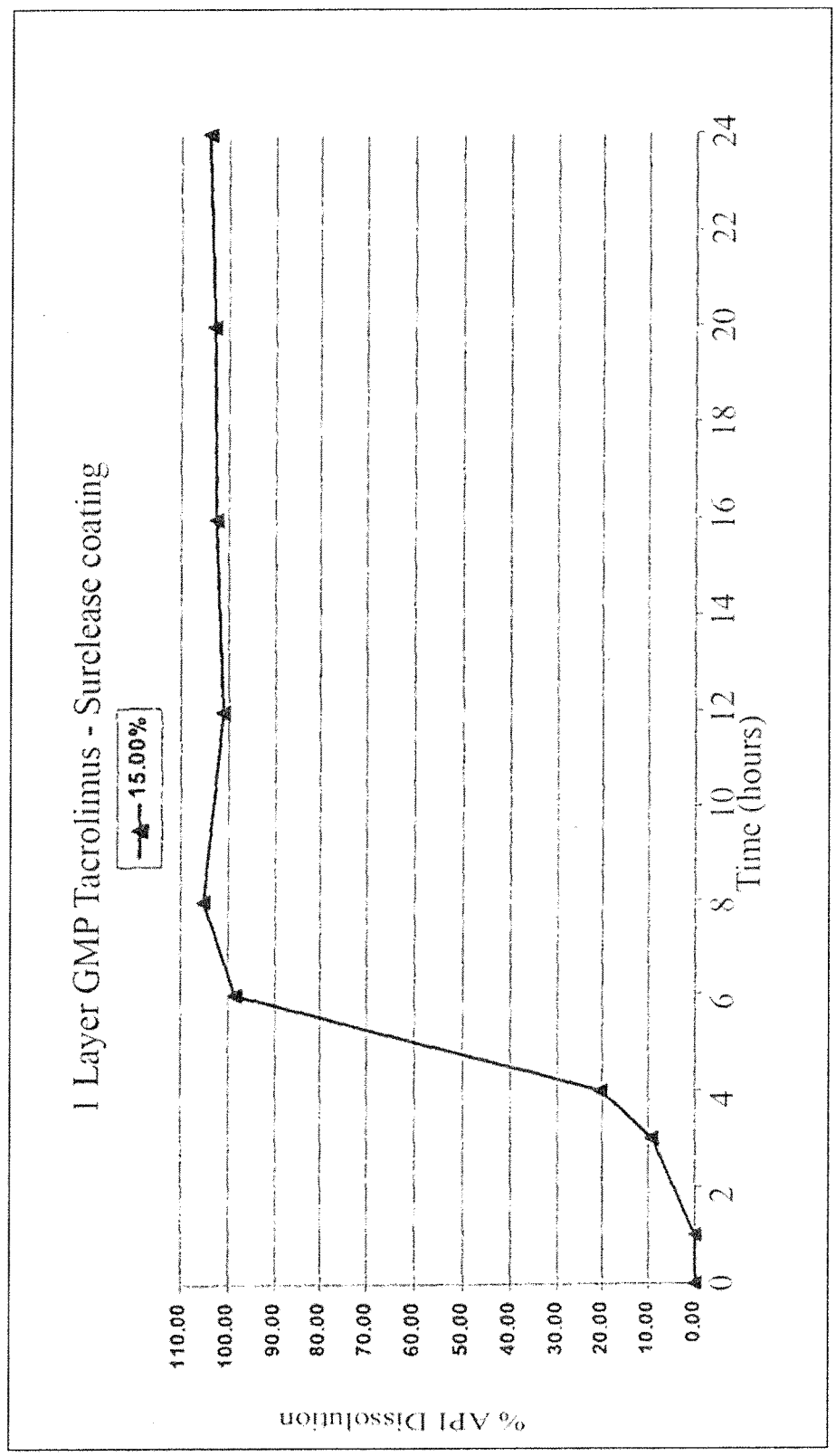
FIG. 15 is a graph showing the dissolution profile for 15% weight gain Surelease® coated micronized tacrolimus solid minicapsules (Format 3)

Tacrolimus release from minicapsules, prepared as per Example 12, coated with 15% weight gain Surelease®: Dissolution profiles in FIG. 15 demonstrate the following release of tacolimus from minicapsules expressed as a percentage of the total minicapsule content: less than 10% within 1 hr; less than 25% within 4 hrs and less than or equal to 100% at 8 hr.

Example 16

Figure 16:
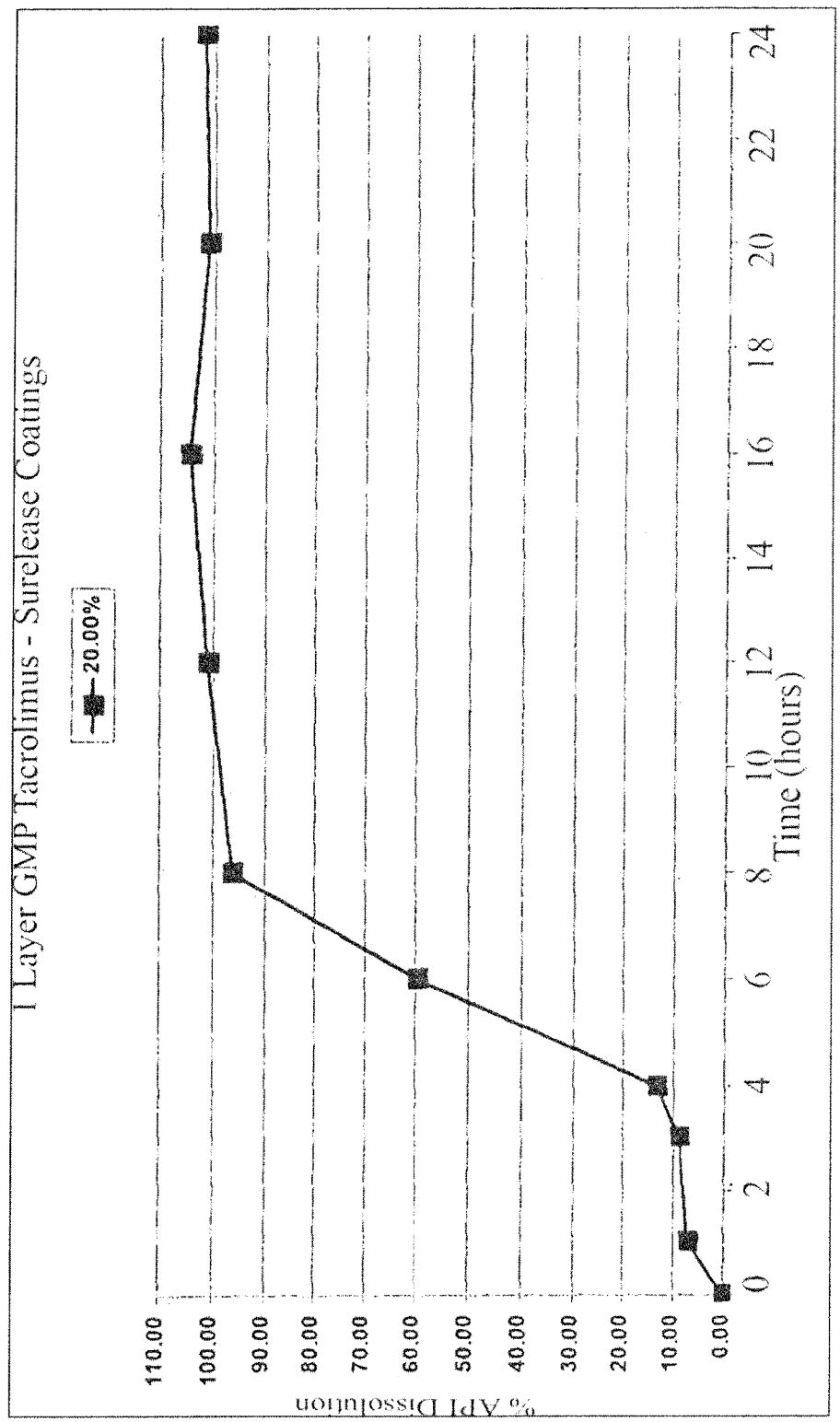
FIG. 16 is a graph showing the dissolution profile for 20% weight gain Surelease® coated micronized tacrolimus solid minicapsules (Format 3)

Tacrolimus release from minicapsules, prepared as per Example 12, coated with 20% weight gain Surelease®: Dissolution profiles in FIG. 16 demonstrate the following release of tacolimus from minicapsules expressed as a percentage of the total minicapsule content: less than 10% within 1 hr; less than 20% within 4 hrs and less than 95% within 8 hrs and less than or equal to 100% at 12 hr.

Example 17

Figure 17:
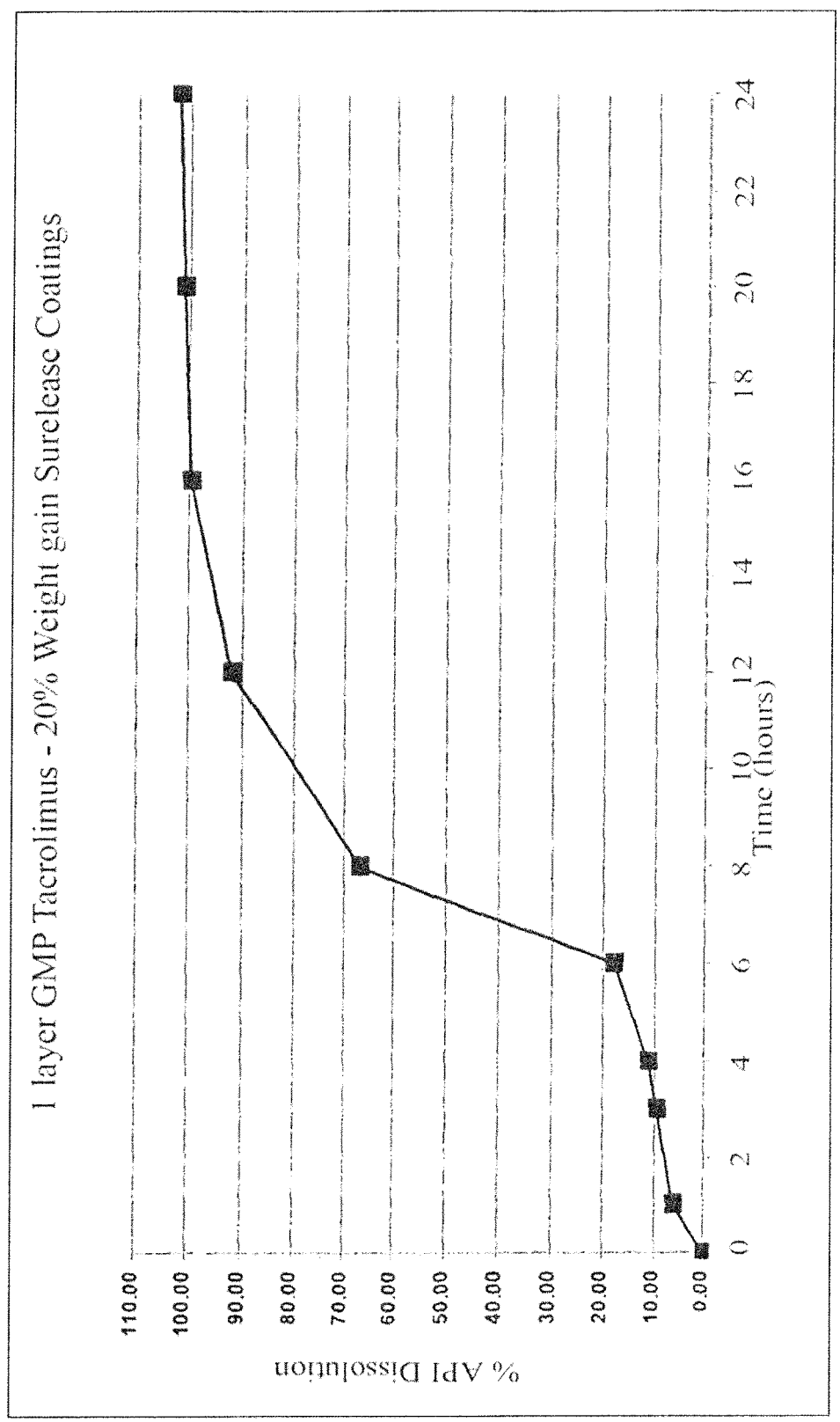
FIG. 17 is a graph showing the dissolution profile for 25% weight gain Surelease® coated micronized tacrolimus solid minicapsules (Format 3)

Tacrolimus release from minicapsules, prepared as per Example 12, coated with 25% weight gain Surelease®: Dissolution profiles in FIG. 17 demonstrate the following release of tacolimus from minicapsules expressed as a percentage of the total minicapsule content: less than 10% within 1 hr; less than 20% within 4 hrs and less than 70% within 8 hrs; less than 95% within 12 hrs and less than or equal to 100% at 24 hr.

Example 18

Figure 18:
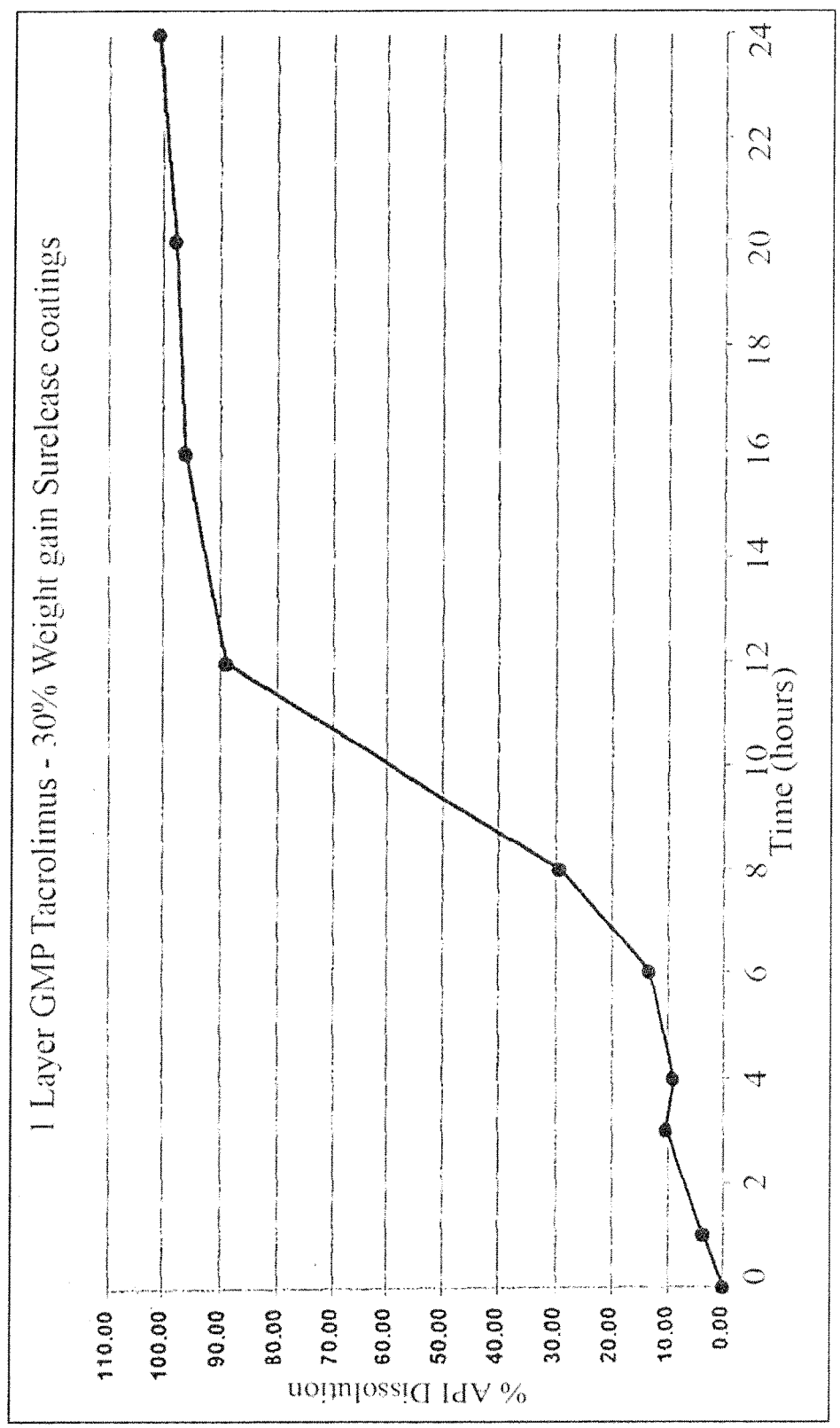
FIG. 18 is a graph showing the dissolution profile for 30% weight gain Surelease® coated micronized tacrolimus solid minicapsules (Format 3)

Tacrolimus release from minicapsules, prepared as per Example 12, coated with 30% weight gain Surelease®: Dissolution profiles in FIG. 18 demonstrate the following release of tacolimus from minicapsules expressed as a percentage of the total minicapsule content: less than 10% within 1 hr; less than 10% within 4 hrs and less than 30% within 8 hrs; less than 90% within 12 hrs and less than or equal to 100% at 24 hr.

Example 19

Figure 19:
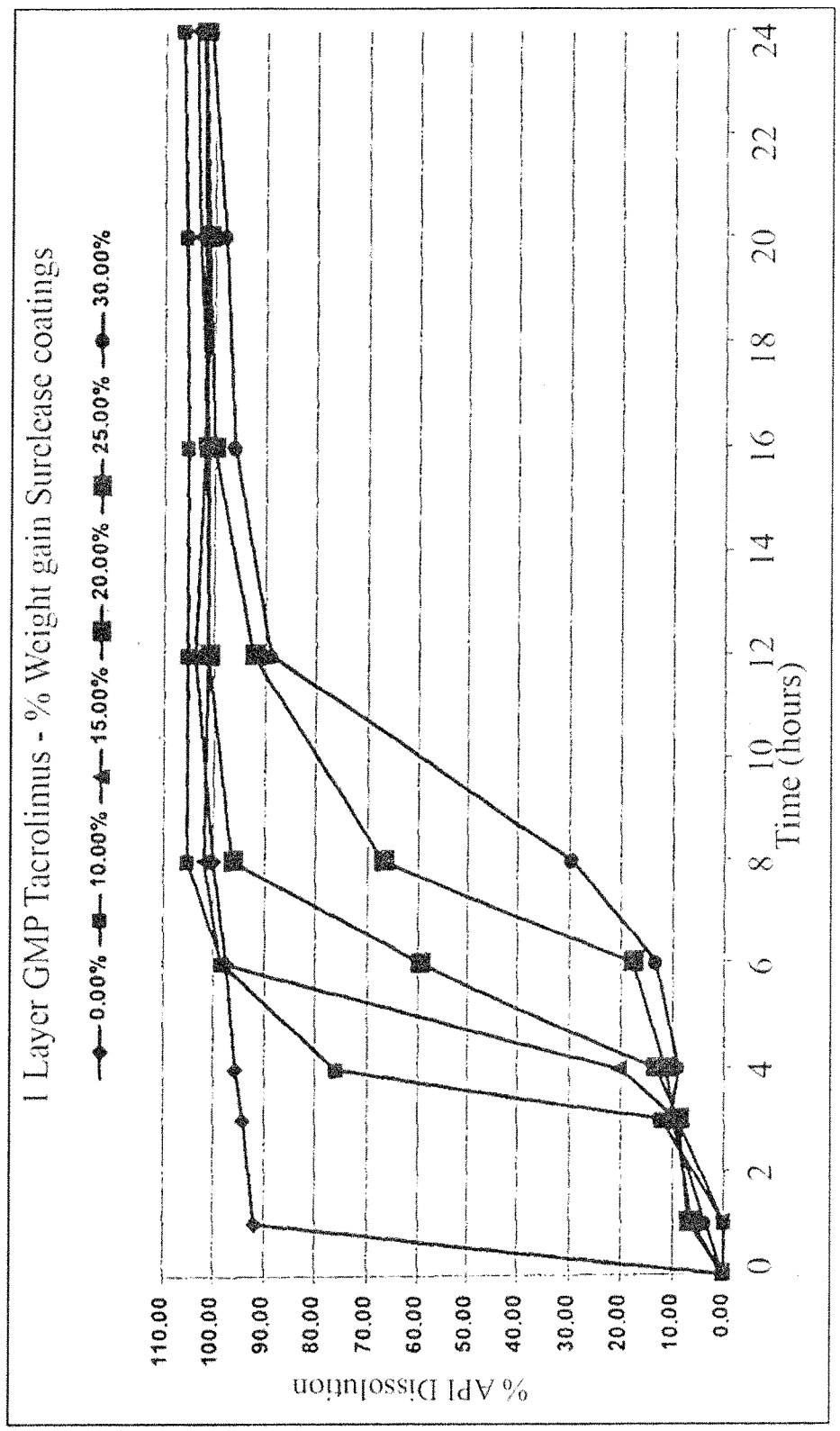
FIG. 19 is a graph showing the dissolution profile of micronized tacrolimus from minicapsules coated with a range (0-30%) of Surelease® weight gains (Format 3)

Tacrolimus release from minicapsules, prepared as per Example 12, coated with a range of Surelease® weight gains (0-30% weight gain): Dissolution profiles in FIG. 19 demonstrate the variable release of tacolimus from minicapsules expressed as a percentage of the total minicapsule content.

Example 20

As per FIG. 3 above, Example 20 is an example of an extruded emulsion drug suspension, in this case hydralazine and is representative of Format 4. Gelatine is mixed with water, heated to 65 degree C. and stirred until dissolved. Hydralazine is added to the heated gelatine solution and the mixture until an homogenous solution (Solution 1). Squalene, Gelucire 44/14 and Labrifil MS 1944 CS is heated and mixed until in an homogenous solution (Solution 2). Solution 1 and Solution 2 are then blended and homogenized to give an emulsified suspension. The emulsified suspension is then, using a single nozzle minicapsule processor or extruder to which a vibration force is applied, extruded and cooled either in a cooling bath or in the air.

TABLE 5

Extruded Hydralazine emulsion suspension

| Ingredients | Wt (g) |
|---|---|
| Core Composition | |
| Hydralazine | 0.1 |
| Gelatine | 10 |
| Water | 40 |
| Squalene | 0.16 |
| Gelucire 44/14 | 0.16 |
| Labrafil MS 1944 CS | 0.8 |

The resulting spherical extruded beads had a content assay of 36 mg/g and a processing yield of over 90% efficiency. The beads are readily dissolved and may be coated to provide any desired release profile,

Example 21

Colitis was induced in mice using DSS 2.5% in drinking water. DMOG mini-capsules of example 20 with two different coating were used, namely DSS-bead (0.25 mg—immediate release), and DSS-COAT-bead (DSS-COAT beads coated with 22% Surelease®—DMOG: 0.25 mg/day) and were compared to non-treated DSS-induced colitis mice and mice treated with 8 mg DMOG IP every second day. The minicapsules were prepared using the method described in Example 20 above.

Figure 20:
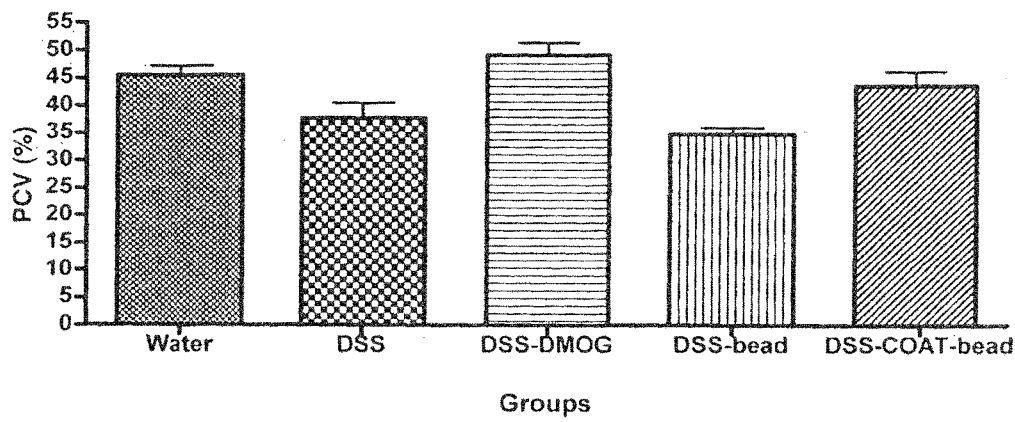
FIG. 20 is a graph representing the packed cell volume (% PCV) of DSS-induced colitis mice treated with DMOG IP (8 mg every second day) and orally in immediate release beads (DSS-beads coated with 12.5% Surelease®—DMOG: 0.25 mg/day) or colon-specific coated beads (DSS-COAT beads coated with 22% Surelease®—DMOG: 0.25 mg/day) for 7 days, with 6 mice in each group (Format 4)

As DMOG is known to increase the production of erythropoietin it is expected that in the presence of systemic DMOG that the packed cell volume would be increased. The packed cell volume (PCV) is a measurement of the proportion of blood that is made up of cells. The value is expressed as a percentage or fraction of cells in blood. The PCV rises when the number of red blood cells increases. FIG. 20 demonstrates that, on Day 7, when administered IP that DMOG increases the PCV, despite the fact that these mice exhibited a high DAI and that the DSS alone reduced the PCV. It is noteworthy that neither the non-coated DSS DMOG beads or the colon-specific coated DMOG beads did not increase the PCV, despite the fact that the colon-specific coated DMOG beads improved the health of the DSS treated mice and that these mice demonstrated improved DAI. Thus, it could be concluded that when administered within the intestinal or colonic lumen that it acts locally at low dose and negligible concentrations are systemically available.

Example 22

Figure 21:
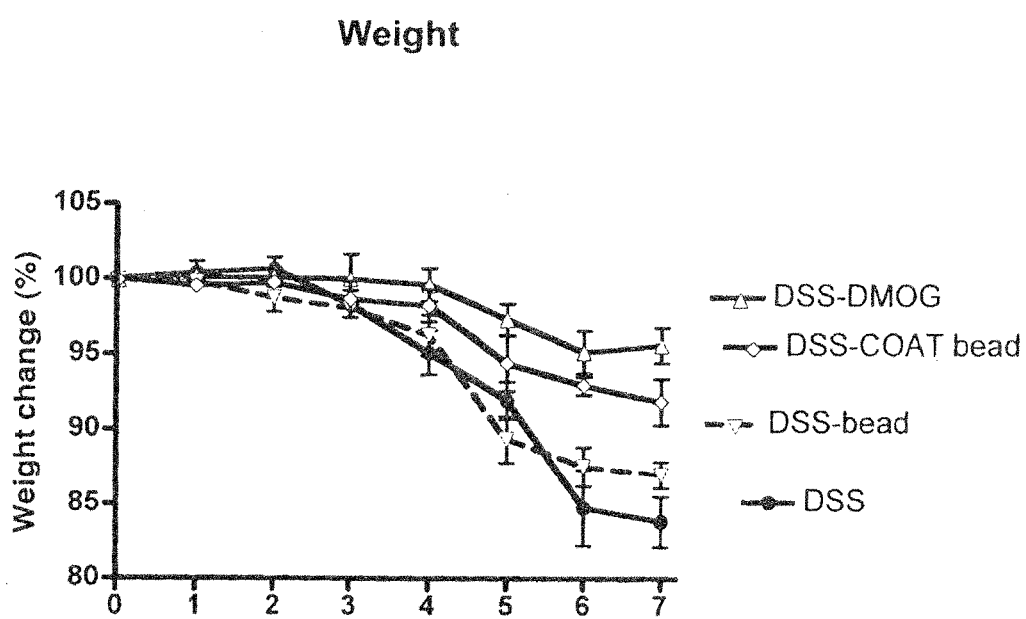
FIG. 21 is a graph showing the Disease Activity Index (DAI) of DSS-induced colitis mice treated with DMOG IP (8 mg DMOG every second day) and orally in immediate release beads (DSS-beads coated with 12.5% Surelease®—DMOG: 0.25 mg/day) or colon-specific coated beads (DSS-COAT beads coated with 22% Surelease®—DMOG: 0.25 mg/day) for 7 days, with 6 mice in each group (Format 4)

Referring to FIG. 21, the disease activity index (DAI) is calculated as the sum of scores of weight loss, stool consistency and blood in feces. Normal stool=formed pellets; loose stool=pasty and semi-formed stool which do not stick to the anus; diarrhoea=liquid stools that stick to the anus. This composite scoring system clearly demonstrates that daily administration of DMOG specifically to the colon (DSS-COAT beads coated with 22% Surelease®—DMOG: 0.25 mg/day) 0.25 mg DMOG produces a pronounced protective effect against the induction of colitis in DSS treated mice. The minicapsules were prepared using the method described in Example 20 above.

Example 23

Figure 22:
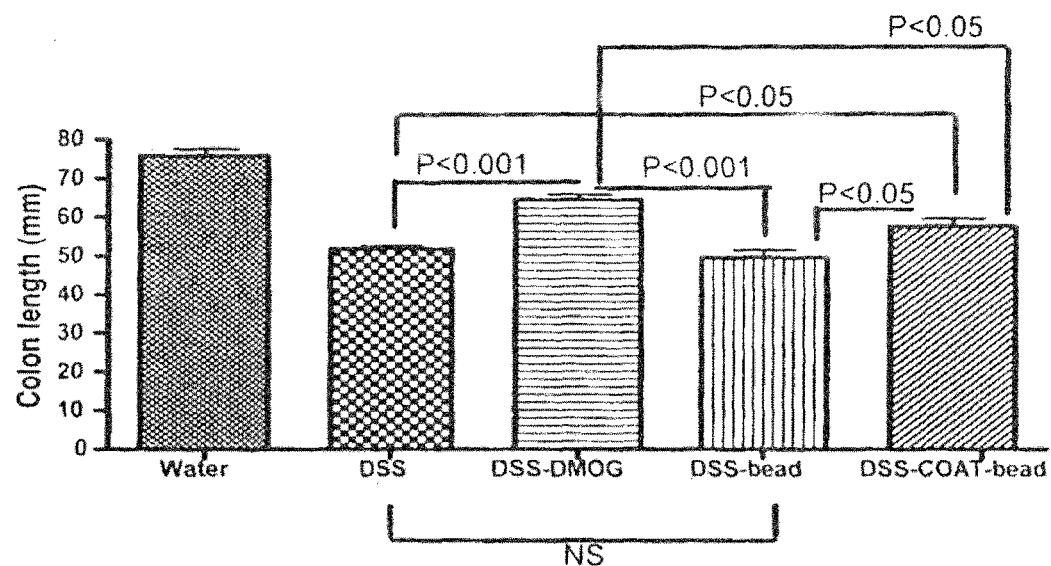
FIG. 22 is a graph showing the average colon length of DSS-induced colitis mice treated with DMOG IP (8 mg DMOG every second day) and orally in immediate release beads (DSS-beads coated with 12.5% Surelease®—DMOG: 0.25 mg/day) or colon-specific coated beads (DSS-COAT beads coated with 22% Surelease®—DMOG: 0.25 mg/day) for 7 days, with 6 mice in each group (Format 4).

Referring to FIG. 22, following removal of the colon from mice on Day 7, it is observed that while the DSS still exerted a shortening affect on the colon length, the administration of DMOG IP (8 mg DMOG every second day) and colon-specific coated DMOG beads (DSS-COAT beads coated with 22% Surelease®—DMOG: 0.25 mg/day) significantly reduced colon shortening, thereby suggesting that DMOG is exerting a protective effect against DSS-induced colitis. A major symptom of DSS-induced colitis is weight loss. From FIG. 21 it is evident that when administered IP (DSS-DMOG) every second day, 8 mg DMOG has a significant protective effect compared with the non-treated mice (DSS). Likewise, when 0.25 mg DMOG is administered daily as colon-specific beads (DSS-COAT beads coated with 22% Surelease®—DMOG: 0.25 mg/day), the protective effect is pronounced. The 0.25 mg DMOG, administered daily in an immediate release format (DSS-bead) had a slight protective effect. This data set suggests that when administered specifically to the colon daily at low concentration; DMOG has a pronounced protective effect on DSS-induced colitis. The minicapsules were prepared using the method described in Example 20 above.

The invention is not limited to the embodiments hereinbefore described which may be varied in detail.

The invention claimed is:

1. A method for treating Celiac disease, wherein the method is selected from A or B:
A. a method comprising administering to a patient in need thereof a composition comprising minicapsules, wherein the minicapsules comprise a steroid in a liquid, semi-solid or solid core, the minicapsules having release profiles to release the steroid in an active form at one or more sites along the gastrointestinal tract, the one or more sites comprising the proximal small intestine beginning at the duodenum and ending at the ileum; and
B. a method comprising administering budesonide to a patient in need thereof in a solubilised drug delivery format.

2. The method of claim 1 wherein the method comprises method A.

3. The method of claim 1 wherein the method comprises method B.

4. The method of claim 2 wherein the minicapsules have one layer and is solid throughout.

5. The method of claim 2 wherein the minicapsules comprise a core of a solution or suspension, the core being encapsulated by a gel forming agent, wherein the minicapsules have the characteristics of minicapsules that are obtained by the utilisation of surface tension of different solutions which are ejected through a nozzle having a single orifice and form into a spherical form and fall into a cooling air flow or into a cooling or hardening solution, wherein the outer shell solution is gelled or solidified.

6. The method of claim 5 wherein the gel forming agent is gelatine based.

7. The method of claim 5 wherein the encapsulating gel-forming agent layer of the minicapsules are modified to enable modified release of the steroid.

8. The method of claim 5 wherein the outer layer of the minicapsules is coated with a modified release coating to enable modified release of the steroid.

9. The method of claim 8 wherein the modified release is controlled release.

10. The method of claim 8 wherein the modified release coating is a polymeric material that is sensitive to one or more of pH, time, thickness, erosion, and bacterial breakdown.

11. The method of claim 10 wherein the modified release coating comprises: any combination of acrylic-, methacrylic and ethylcellulose based polymers and HPMC and derivatives.

12. The method of claim 2, wherein the minicapsules comprise a shell/core mixed suspension, the core being a solution or suspension, wherein the minicapsules have the characteristics of minicapsules that are obtained by ejecting a shell/core mixed suspension, which is formed through the utilisation of surface tension of different solutions, through a nozzle having a single orifice, the shell/core mixed suspension forming into a spherical form and falling into a cooling air flow or into a cooling or hardening solution and the outer shell solution is gelled or solidified.

13. The method of claim 12, wherein the outer shell solution is any gel forming agent.

14. The method of claim 13, wherein the gel forming agent is gelatine based.

15. The method of claim 12 wherein the minicapsules are modified to enable modified release of the steroid, the modification being chosen from:
modifying the shell of the minicapsule to achieve modified release; or
coating the outer shell layer of the minicapsule with a modified release coating.

16. The method of claim 15 wherein the modified release coating is a polymeric material that is sensitive to one or more of pH, time, thickness, erosion, and bacterial breakdown.

17. The method of claim 16 wherein the modified release coating comprises: any combination of acrylic-, methacrylic and ethylcellulose based polymers, and HPMC and derivatives.

18. The method of claim 2 wherein the minicapsules comprise an emulsion comprising a gelling agent which emulsion is in extruded, gelled and dried form.

19. The composition of claim 18 wherein the steroid is solubilised in a solution and the minicapsules comprise gelatin as a gelling agent.

20. The method of claim 19 wherein the steroid is budesonide.

21. The method of claim 20 wherein the outer layers of the minicapsules are coated with a modified release coating to enable modified release of the steroid.

22. The method of claim 2 wherein the steroid is solubilised or readily soluble in liquid or hydrolysable semi-solids or solids and is encapsulated into the minicapsule core by a gelling agent wherein the encapsulating shell includes or is coated with intestinal controlled release polymers.

23. The method of claim 2 wherein the minicapsules are coated with a coating, wherein the coating comprises a controlled release coating.

24. The method of claim 23 wherein the coating is an enteric or pH dependent polymer.

25. The method of claim 2 wherein the steroid is budesonide.

26. The method of claim 3 wherein the budesonide is formulated into a modified release composition to deliver the budesonide in the proximal small intestine, beginning at the duodenum and ending at the ileum.

27. The method of claim 26 wherein the composition delivers the budesonide to the proximal small intestine beginning at the duodenum or the jejunum.

28. The method of claim 3, wherein the budesonide is formulated into a composition comprising minicapsules, wherein the minicapsules comprise an emulsion comprising a gelling agent which emulsion is in extruded, gelled and dried form.

29. The method of claim 28 wherein the composition further comprises a fatty acid ester.

30. The method of claim 28 wherein the budesonide is solubilised in a solution and the minicapsules comprise gelatin as a gelling agent.

31. The method of claim 28 wherein the minicapsules are modified to enable modified release of the steroid, the modification being chosen from:
    modifying the shell of the minicapsules to achieve modified release; or
    coating the outer shell layer of the minicapsules with a modified release coating.

32. The method of claim 31 wherein the modified release coating comprises: any combination of acrylic-, methacrylic and ethylcellulose based polymers, and HPMC and derivatives.

* * * * *